(12) United States Patent
Ju et al.

(10) Patent No.: US 10,648,026 B2
(45) Date of Patent: May 12, 2020

(54) RAMAN CLUSTER TAGGED MOLECULES FOR BIOLOGICAL IMAGING

(71) Applicants: Jingyue Ju, Englewood Cliffs, NJ (US); Shiv Kumar, Belle Mead, NJ (US); Mirkó Palla, Newton, MA (US); James J. Russo, New York, NY (US)

(72) Inventors: Jingyue Ju, Englewood Cliffs, NJ (US); Shiv Kumar, Belle Mead, NJ (US); Mirkó Palla, Newton, MA (US); James J. Russo, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 880 days.

(21) Appl. No.: 14/775,451

(22) PCT Filed: Mar. 14, 2014

(86) PCT No.: PCT/US2014/029477
§ 371 (c)(1),
(2) Date: Sep. 11, 2015

(87) PCT Pub. No.: WO2014/144883
PCT Pub. Date: Sep. 18, 2014

(65) Prior Publication Data
US 2016/0024570 A1    Jan. 28, 2016

Related U.S. Application Data

(60) Provisional application No. 61/799,082, filed on Mar. 15, 2013.

(51) Int. Cl.
*C12Q 1/68*    (2018.01)
*C12Q 1/6869*    (2018.01)
(Continued)

(52) U.S. Cl.
CPC ........ *C12Q 1/6869* (2013.01); *C12Q 1/6874* (2013.01); *G01N 21/65* (2013.01); *G01N 21/658* (2013.01)

(58) Field of Classification Search
CPC .................................................. C12Q 1/6869
(Continued)

(56) References Cited

U.S. PATENT DOCUMENTS 4,711,955 A    12/1987    Ward et al.
4,772,691 A    9/1988    Herman
(Continued)

FOREIGN PATENT DOCUMENTS

WO    WO 1989/009282    10/1989
WO    WO 1989/011548    11/1989
(Continued)

OTHER PUBLICATIONS

Notification of Transmittal of the International Search Report and the Written Opinion of the International Searching Authority, or the Declaration, including an International Search Report Written Opinion of the International Searching Authority, dated Aug. 11, 2014 in connection with PCT International Application No. PCT/US2014/029477, filed Mar. 14, 2014.

(Continued)

*Primary Examiner* — Jezia Riley
(74) *Attorney, Agent, or Firm* — John P. White; Gary J. Gershik; Cooper & Dunham LLP

(57) ABSTRACT

This invention provides nucleoside polyphosphate analogs each of which comprises a tag comprising a plurality of Raman-scattering moieties; compounds comprising said nucleoside polyphosphate analogs; and methods for determining the sequence of a single-stranded DNA or RNA using said nucleoside polyphosphate analogs. This invention also provides methods for detecting the interaction of a (Continued)

plurality of predetermined compounds, at least one of which having attached thereto a tag comprising a plurality of Raman-scattering moieties.

20 Claims, 12 Drawing Sheets

(51) Int. Cl.
*C12Q 1/6874* (2018.01)
*G01N 21/65* (2006.01)

(58) Field of Classification Search
USPC .......................................... 435/6.12; 536/4.1
See application file for complete search history.

(56) References Cited

U.S. PATENT DOCUMENTS

| | | | |
|---|---|---|---|
| 4,804,748 A | 2/1989 | Seela | |
| 4,824,775 A | 4/1989 | Dattagupta et al. | |
| 4,863,849 A | 9/1989 | Melamede | |
| 5,043,272 A | 8/1991 | Hartley | |
| 5,047,519 A | 9/1991 | Hobbs, Jr. et al. | |
| 5,118,605 A | 6/1992 | Urdea | |
| 5,174,962 A | 12/1992 | Brennan | |
| 5,175,269 A | 12/1992 | Stavrianopoulos | |
| 5,242,796 A | 9/1993 | Prober et al. | |
| 5,302,509 A | 4/1994 | Cheeseman | |
| 5,308,990 A | 5/1994 | Takahashi et al. | |
| 5,328,824 A | 7/1994 | Ward et al. | |
| 5,332,666 A | 7/1994 | Prober et al. | |
| 5,436,143 A | 7/1995 | Hyman | |
| 5,437,975 A | 8/1995 | McClelland et al. | |
| 5,449,767 A | 9/1995 | Ward et al. | |
| 5,476,928 A | 12/1995 | Ward et al. | |
| 5,516,664 A | 5/1996 | Hyman | |
| 5,534,424 A | 7/1996 | Uhlen et al. | |
| 5,547,839 A | 8/1996 | Dower et al. | |
| 5,547,859 A | 8/1996 | Goodman et al. | |
| 5,556,748 A | 9/1996 | Douglas | |
| 5,599,675 A | 2/1997 | Brenner | |
| 5,602,000 A | 2/1997 | Hyman | |
| 5,637,469 A | 6/1997 | Wilding et al. | |
| 5,654,419 A | 8/1997 | Mathies et al. | |
| 5,658,736 A | 8/1997 | Wong | |
| 5,709,999 A | 1/1998 | Shattuck-Eidens et al. | |
| 5,714,330 A | 2/1998 | Brenner et al. | |
| 5,728,528 A | 3/1998 | Mathies et al. | |
| 5,763,594 A | 6/1998 | Hiatt et al. | |
| 5,770,365 A | 6/1998 | Lane et al. | |
| 5,770,367 A | 6/1998 | Southern et al. | |
| 5,789,167 A | 8/1998 | Konrad | |
| 5,798,210 A | 8/1998 | Canard et al. | |
| 5,804,386 A | 9/1998 | Ju | |
| 5,808,045 A | 9/1998 | Hiatt et al. | |
| 5,814,454 A | 9/1998 | Ju | |
| 5,821,356 A | 10/1998 | Khan et al. | |
| 5,834,203 A | 11/1998 | Katzir et al. | |
| 5,844,106 A | 12/1998 | Seela et al. | |
| 5,849,542 A | 12/1998 | Reeve et al. | |
| 5,853,992 A | 12/1998 | Glazer et al. | |
| 5,856,104 A | 1/1999 | Chee et al. | |
| 5,869,255 A | 2/1999 | Mathies et al. | |
| 5,872,244 A | 2/1999 | Hiatt et al. | |
| 5,876,936 A | 3/1999 | Ju | |
| 5,885,775 A | 3/1999 | Haff et al. | |
| 5,908,755 A | 6/1999 | Kumar et al. | |
| 5,945,283 A | 8/1999 | Kwok et al. | |
| 5,952,180 A | 9/1999 | Ju | |
| 5,962,228 A | 10/1999 | Brenner | |
| 6,001,566 A | 12/1999 | Canard et al. | |
| 6,001,611 A | 12/1999 | Will | |
| 6,008,379 A | 12/1999 | Benson et al. | |
| 6,028,190 A | 2/2000 | Mathies et al. | |
| 6,046,005 A | 4/2000 | Ju et al. | |
| 6,074,823 A | 6/2000 | Koster | |
| 6,087,095 A | 7/2000 | Rosenthal et al. | |
| 6,136,543 A | 10/2000 | Anazawa et al. | |
| 6,175,107 B1 | 1/2001 | Juvinall | |
| 6,197,557 B1 | 3/2001 | Makarov et al. | |
| 6,207,831 B1 | 3/2001 | Auer et al. | |
| 6,210,891 B1 | 4/2001 | Nyren et al. | |
| 6,214,987 B1 | 4/2001 | Hiatt et al. | |
| 6,218,118 B1 | 4/2001 | Sampson et al. | |
| 6,218,530 B1 | 4/2001 | Rothschild et al. | |
| 6,221,592 B1 | 4/2001 | Schwartz et al. | |
| 6,232,465 B1 | 5/2001 | Hiatt et al. | |
| 6,242,193 B1 | 6/2001 | Anazawa et al. | |
| 6,245,507 B1 | 6/2001 | Bogdanov | |
| 6,255,083 B1 | 7/2001 | Williams | |
| 6,255,475 B1 | 7/2001 | Kwiatkowski | |
| 6,274,320 B1 | 8/2001 | Rothberg et al. | |
| 6,277,607 B1 | 8/2001 | Tyagi et al. | |
| 6,287,821 B1 | 9/2001 | Shi et al. | |
| 6,294,324 B1 | 9/2001 | Bensimon et al. | |
| 6,309,829 B1 | 10/2001 | Livak et al. | |
| 6,309,836 B1 | 10/2001 | Kwiatkowski | |
| 6,312,893 B1 | 11/2001 | Van Ness et al. | |
| 6,316,230 B1 | 11/2001 | Egholm et al. | |
| 6,335,155 B1 | 1/2002 | Wells et al. | |
| 6,361,940 B1 | 3/2002 | Van Ness et al. | |
| 6,380,378 B1 | 4/2002 | Kitamura et al. | |
| 6,495,680 B1 | 12/2002 | Gong | |
| 6,524,829 B1 | 2/2003 | Seeger | |
| 6,555,349 B1 | 4/2003 | O'Donnell | |
| 6,613,508 B1 | 9/2003 | Ness et al. | |
| 6,613,513 B1 | 9/2003 | Parce et al. | |
| 6,627,748 B1 | 9/2003 | Ju et al. | |
| 6,632,655 B1 | 10/2003 | Mehta et al. | |
| 6,639,088 B2 | 10/2003 | Kwiatkowski | |
| 6,664,079 B2 | 12/2003 | Ju et al. | |
| 6,664,399 B1 | 12/2003 | Sabesan | |
| 6,713,255 B1 | 3/2004 | Makino et al. | |
| 6,780,591 B2 | 8/2004 | Williams et al. | |
| 6,787,308 B2 | 9/2004 | Balasubramanian et al. | |
| 6,818,395 B1 | 11/2004 | Quake et al. | |
| 6,833,246 B2 | 12/2004 | Balasubramanian | |
| 6,858,393 B1 | 2/2005 | Anderson et al. | |
| 6,864,052 B1 | 3/2005 | Drmanac et al. | |
| 6,911,345 B2 | 6/2005 | Quake et al. | |
| 6,934,636 B1 | 8/2005 | Skierczynski et al. | |
| 6,982,146 B1 | 1/2006 | Schneider et al. | |
| 7,037,687 B2 | 5/2006 | Williams et al. | |
| 7,056,661 B2 | 6/2006 | Korlach et al. | |
| 7,056,666 B2 | 6/2006 | Dower et al. | |
| 7,057,026 B2 | 6/2006 | Barnes et al. | |
| 7,057,031 B2 | 6/2006 | Olejnik et al. | |
| 7,074,597 B2 | 7/2006 | Ju | |
| 7,078,499 B2 | 7/2006 | Odedra et al. | |
| 7,105,300 B2 | 9/2006 | Parce et al. | |
| 7,270,951 B1 | 9/2007 | Stemple et al. | |
| 7,329,496 B2 | 2/2008 | Dower et al. | |
| 7,345,159 B2 | 3/2008 | Ju et al. | |
| 7,414,116 B2 | 8/2008 | Milton et al. | |
| 7,427,673 B2 | 9/2008 | Balasubramanian et al. | |
| 7,459,275 B2 | 12/2008 | Dower et al. | |
| 7,566,537 B2 | 7/2009 | Balasubramanian et al. | |
| 7,622,279 B2 | 11/2009 | Ju | |
| 7,635,578 B2 | 12/2009 | Ju et al. | |
| 7,713,698 B2 | 5/2010 | Ju et al. | |
| 7,790,869 B2 | 9/2010 | Ju et al. | |
| 7,883,869 B2 | 2/2011 | Ju et al. | |
| 7,982,029 B2 | 7/2011 | Ju et al. | |
| 8,088,575 B2 | 1/2012 | Ju et al. | |
| 8,298,792 B2 | 10/2012 | Ju et al. | |
| 8,796,432 B2 | 8/2014 | Ju et al. | |
| 8,889,348 B2 | 11/2014 | Ju | |
| 9,115,163 B2 | 8/2015 | Ju et al. | |
| 9,133,511 B2 | 9/2015 | Ju et al. | |
| 9,159,610 B2 | 10/2015 | Zhang et al. | |
| 9,175,342 B2 | 11/2015 | Ju et al. | |
| 9,255,292 B2 | 2/2016 | Ju et al. | |
| 9,297,042 B2 | 3/2016 | Ju et al. | |
| 2002/0012966 A1 | 1/2002 | Shi et al. | |

(56) References Cited

U.S. PATENT DOCUMENTS

| | | |
|---|---|---|
| 2002/0168642 A1 | 11/2002 | Drukier |
| 2003/0008285 A1 | 1/2003 | Fischer |
| 2003/0022225 A1 | 1/2003 | Monforte et al. |
| 2003/0027140 A1 | 2/2003 | Ju et al. |
| 2003/0044871 A1 | 3/2003 | Cutsforth et al. |
| 2003/0054360 A1 | 3/2003 | Gold et al. |
| 2003/0099972 A1 | 5/2003 | Olejnik et al. |
| 2003/0166282 A1 | 9/2003 | Brown et al. |
| 2003/0186256 A1 | 10/2003 | Fischer |
| 2003/0190680 A1 | 10/2003 | Rothschild et al. |
| 2003/0198982 A1 | 10/2003 | Seela et al. |
| 2004/0014096 A1 | 1/2004 | Anderson et al. |
| 2004/0096825 A1 | 5/2004 | Chenna et al. |
| 2005/0032081 A1 | 2/2005 | Ju et al. |
| 2005/0170367 A1 | 8/2005 | Quake et al. |
| 2005/0239134 A1 | 10/2005 | Gorenstein et al. |
| 2006/0003352 A1 | 1/2006 | Lipkin et al. |
| 2006/0057565 A1 | 3/2006 | Ju et al. |
| 2006/0105461 A1 | 5/2006 | Tom-Moy et al. |
| 2006/0160081 A1 | 7/2006 | Milton et al. |
| 2006/0160113 A1 | 7/2006 | Korlach et al. |
| 2006/0240439 A1 | 10/2006 | Smith et al. |
| 2006/0252038 A1 | 11/2006 | Ju |
| 2007/0166705 A1 | 7/2007 | Milton et al. |
| 2008/0241866 A1* | 10/2008 | Korlach ............ G01N 21/6452 435/8 |
| 2009/0088332 A1 | 4/2009 | Ju et al. |
| 2009/0240030 A1 | 9/2009 | Ju et al. |
| 2011/0014611 A1 | 1/2011 | Ju et al. |
| 2012/0052489 A1 | 3/2012 | Gordon et al. |
| 2012/0142006 A1 | 6/2012 | Ju et al. |
| 2013/0264207 A1 | 10/2013 | Ju et al. |
| 2014/0093869 A1 | 4/2014 | Ju et al. |
| 2014/0315191 A1 | 10/2014 | Ju et al. |
| 2015/0037788 A1 | 2/2015 | Ju |
| 2015/0080232 A1 | 3/2015 | Ju et al. |
| 2015/0111759 A1 | 4/2015 | Ju et al. |
| 2015/0119259 A1 | 4/2015 | Ju et al. |
| 2015/0368710 A1 | 12/2015 | Fuller et al. |
| 2016/0041179 A1 | 2/2016 | Ju et al. |
| 2016/0090621 A1 | 3/2016 | Ju et al. |

FOREIGN PATENT DOCUMENTS

| | | |
|---|---|---|
| WO | WO 1990/013666 | 11/1990 |
| WO | WO 1991/006678 | 5/1991 |
| WO | WO 1992/010587 | 6/1992 |
| WO | WO 1993/005183 | 3/1993 |
| WO | WO 1993/021340 | 10/1993 |
| WO | WO 1994/014972 | 7/1994 |
| WO | WO 1996/007669 | 3/1996 |
| WO | WO 1996/023807 | 8/1996 |
| WO | WO 1996/027025 | 9/1996 |
| WO | WO 1997/032999 | 9/1997 |
| WO | WO 1997/046704 | 12/1997 |
| WO | WO 2000/002895 | 1/2000 |
| WO | WO 2000/006770 | 2/2000 |
| WO | WO 2000/015844 | 3/2000 |
| WO | WO 2000/018956 | 4/2000 |
| WO | WO 2000/021974 | 4/2000 |
| WO | WO 2000/050172 | 8/2000 |
| WO | WO 2000/050642 | 8/2000 |
| WO | WO 2000/053805 | 9/2000 |
| WO | WO 2000/053812 | 9/2000 |
| WO | WO 2000/070073 | 11/2000 |
| WO | WO 2001/016375 | 3/2001 |
| WO | WO 2001/023610 | 4/2001 |
| WO | WO 2001/025247 | 4/2001 |
| WO | WO 2001/027625 | 4/2001 |
| WO | WO 2001/032930 | 5/2001 |
| WO | WO 2001/048235 | 7/2001 |
| WO | WO 2001/057248 | 8/2001 |
| WO | WO 2001/057249 | 8/2001 |
| WO | WO 2001/092284 | 12/2001 |
| WO | WO 2001/094609 | 12/2001 |
| WO | WO 2002/002813 | 1/2002 |
| WO | WO 02/22883 | 3/2002 |
| WO | WO 02/29003 | 4/2002 |
| WO | WO 2002/072892 | 9/2002 |
| WO | WO 02/079519 | 10/2002 |
| WO | WO 2002/088381 | 11/2002 |
| WO | WO 2002/088382 | 11/2002 |
| WO | WO 2003/002767 | 1/2003 |
| WO | WO 2003/020734 | 3/2003 |
| WO | WO 2003/020968 | 3/2003 |
| WO | WO 2003/048178 | 6/2003 |
| WO | WO 2003/048387 | 6/2003 |
| WO | WO 2003/085135 | 10/2003 |
| WO | WO 2004/018493 | 3/2004 |
| WO | WO 2004/018497 | 3/2004 |
| WO | WO 04/055160 | 7/2004 |
| WO | WO 2004/071155 | 8/2004 |
| WO | WO 2004/072238 | 8/2004 |
| WO | WO 05/084367 | 11/2005 |
| WO | WO 04/07773 | 1/2006 |
| WO | WO 2006/073436 | 7/2006 |
| WO | WO 2006/097320 | 9/2006 |
| WO | WO 07/002204 | 1/2007 |
| WO | WO 07/053702 | 5/2007 |
| WO | WO 07/053719 | 5/2007 |
| WO | WO 2007/062105 | 5/2007 |
| WO | WO 2007/127327 | 11/2007 |
| WO | WO 2008/034602 | 3/2008 |
| WO | WO 08/69973 | 6/2008 |
| WO | WO 2008/102120 | 8/2008 |
| WO | WO 2008/124107 | 10/2008 |
| WO | WO 2009/007743 | 1/2009 |
| WO | WO 2009/020682 | 2/2009 |
| WO | WO 09/51807 | 4/2009 |
| WO | WO 2010/109197 | 9/2010 |
| WO | WO 2011/038241 | 3/2011 |
| WO | WO 2011/106459 | 9/2011 |
| WO | WO 2012/009578 | 1/2012 |
| WO | 2012/083249 | 6/2012 |
| WO | WO 2012/083249 A2 | 6/2012 |
| WO | WO 2012/162429 | 11/2012 |
| WO | WO 2012/162429 A2 | 11/2012 |
| WO | WO 2013/016486 | 1/2013 |
| WO | WO 2013/123450 | 8/2013 |
| WO | WO 2013/154999 | 10/2013 |
| WO | WO 2013/188841 | 12/2013 |
| WO | WO 2013/191793 | 12/2013 |
| WO | WO 2014/144883 | 9/2014 |
| WO | WO 2014/144898 | 9/2014 |
| WO | WO 2015/123430 | 8/2015 |
| WO | WO 2015/148402 | 10/2015 |
| WO | WO 2015/179284 | 11/2015 |

OTHER PUBLICATIONS

Office Action dated Feb. 18, 2010 in connection with U.S. Appl. No. 12/312,903.

Jul. 16, 2010 Amendment in response to Office Action dated Feb. 18, 2010 in connection with U.S. Appl. No. 12/312,903.

Notice of Allowance dated Sep. 27, 2010 in connection with U.S. Appl. No. 12/312,903.

Office Action dated Nov. 9, 2011 in connection with U.S. Appl. No. 13/023,283.

May 9, 2012 Response to Office Action dated Nov. 9, 2011 in connection with U.S. Appl. No. 13/023,283.

Notice of Allowance dated Jun. 6, 2012 in connection with U.S. Appl. No. 13/023,283.

Office Action dated Oct. 1, 2013 in connection with U.S. Appl. No. 13/665,588.

Notice of Abandonment dated Apr. 10, 2014 in connection with U.S. Appl. No. 13/665,588.

Office Action dated Jun. 16, 2015 in connection with U.S. Appl. No. 14/242,487.

Response to Office Action, filed Sep. 16, 2015 in connection with U.S. Appl. No. 14/242,487.

(56) References Cited

OTHER PUBLICATIONS

Final Office Action, dated Dec. 2, 2015 in connection with U.S. Appl. No. 14/242,487.
Response to Office Action, filed May 25, 2016 in connection with U.S. Appl. No. 14/242,487 Ju et al.
Notification of Transmittal of International Search Report and Written Opinion, dated Aug. 12, 2008 in connection with International Application No. PCT/US07/24646.
Notification Concerning Transmittal of International Preliminary Report on Patentability, dated Jun. 11, 2009 in connection with International Application No. PCT/US07/24646.
Sep. 28, 2010 Communication issued in connection with UK Patent Application No. 0909600.9.
Mar. 29, 2011 Response to Sep. 28, 2010 Communication issued in connection with UK Patent Application No. 0909600.9.
Dec. 8, 2014 Office Action issued in connection with German Patent Application No. 11 2007 002 932.3.
Mar. 11, 2015 Response to Dec. 8, 2014 Office Action issued in connection with German Patent Application No. 11 2007 002 932.3.
Office Action dated Oct. 3, 2012 in connection with U.S. Appl. No. 12/734,229.
Apr. 3, 2013 Response to Office Action dated Oct. 3, 2012 in connection with U.S. Appl. No. 12/734,229.
Office Action dated Oct. 1, 2013 in connection with U.S. Appl. No. 12/734,229.
Apr. 1, 2014 Response to Office Action dated Oct. 1, 2013 in connection with U.S. Appl. No. 12/734,229.
Office Action dated May 27, 2014 in connection with U.S. Appl. No. 12/734,229.
Oct. 27, 2014 Pre-Appeal Brief Request for Review in connection with U.S. Appl. No. 12/734,229.
Office Action dated Dec. 10, 2014 in connection with U.S. Appl. No. 12/734,229.
Mar. 10, 2015 Amendment in Response to Office Action dated Dec. 10, 2014 in connection with U.S. Appl. No. 12/734,229.
Apr. 6, 2015 Notice of Allowance in connection with U.S. Appl. No. 12/734,229.
International Search Report issued by the International Searching Authority (ISA/US) dated Jan. 30, 2009 in connection with International Application No. PCT/US2008/011913.
Written Opinion of the International Searching Authority issued by the International Searching Authority (ISA/US) dated Apr. 20, 2010 in connection with International Application No. PCT/US2008/011913.
Extended European Search Report and Search Opinion dated Jul. 24, 2012 in connection with European Patent Application No. 08841439.6.
Feb. 20, 2013 Response to Communication under Rule 70(2) and 70a(2) EPC issued Aug. 10, 2012 in connection with European Patent Application No. 08841439.6.
Apr. 1, 2014 Communication transmitting Extended European Search Report and European Search Opinion in connection with European Patent Application No. 13188731.7.
Oct. 28, 2014 Response to Apr. 1, 2014 Communication transmitting Extended European Search Report and European Search Opinion in connection with European Patent Application No. 13188731.7.
Communication Pursuant to Article 94(3) EPC, dated Jun. 24, 2016 by the EPO in connection with EP 13188731.7.
Office Action dated Sep. 18, 2012 in connection with U.S. Appl. No. 12/734,227.
Amendment filed Mar. 18, 2013 in response to Office Action dated Sep. 18, 2012 in connection with U.S. Appl. No. 12/734,227.
Notice of Allowance dated Apr. 26, 2013 in connection with U.S. Appl. No. 12/734,227.
Notice of Abandonment dated Sep. 30, 2013 in connection with U.S. Appl. No. 12/734,227.
Office Action dated Jan. 28, 2015 in connection with U.S. Appl. No. 13/951,269.
Amendment filed Apr. 28, 2015 in response to Office Action dated Jan. 28, 2015 in connection with U.S. Appl. No. 13/951,269.
Jun. 15, 2015 Notice of Allowance in connection with U.S. Appl. No. 13/951,269.
Dec. 7, 2015 Preliminary Amendment in connection with U.S. Appl. No. 14/859,853, Ju et al.
Mar. 23, 2016 Office Action issued in connection with U.S. Appl. No. 14/859,853, Ju et al.
Written Opinion of the International Searching Authority issued by the International Searching Authority (ISA/US) dated Feb. 10, 2009 in connection with International Application No. PCT/US2008/011891.
International Preliminary Report on Patentability, dated Apr. 20, 2010 by the International Bureau of WIPO in connection with PCT International Application No. PCT/US2008/011891.
Supplementary European Search Report and European Search Opinion dated Dec. 17, 2013 in connection with European Patent Application No. 08839081.0.
Amendment filed Jul. 15, 2014 in response to Jan. 9, 2014 Communication Pursuant to Rules 70(2) and 70a(2) in connection with European Patent Application No. 08839081.0.
Communication under Rule 71(3) EPC dated Nov. 17, 2014 in connection with European Patent Application No. 08839081.0.
Supplementary European Search Report and European Search Opinion dated Jul. 21, 2015 in connection with European Patent Application No. 15165262.5.
Communication Pursuant to Rule 69 EPC and Invitation Pursuant to Rule 70(a)1 EPC, issued by the European Patent Office dated Sep. 11, 2015 in connection with EP 15165262.5.
May 4, 2016 Response to Sep. 11, 2015 Communication Pursuant to Rule 69 EPC and Invitation Pursuant to Rule 70(a)1 EPC, issued by the EPO in connection with EP 15165262.5.
May 11, 2016 Restriction Requirement issued in connection with U.S. U.S. Appl. No. 14/119846, Ju et al.
Notification of Transmittal of the International Search Report and the Written Opinion of the International Searching Authority, or the Declaration, including an International Search Report and Written Opinion of the International Searching Authority, dated Sep. 13, 2012 in connection with PCT International Application No. PCT/US2012/039198, filed May 23, 2012.
International Preliminary Report on Patentability, dated Mar. 25, 2014 by the International Bureau of WIPO in connection with PCT International Application No. PCT/US2012/039198.
Notification of Transmittal of the International Search Report and the Written Opinion of the International Searching Authority, or the Declaration, including an International Search Report and Written Opinion of the International Searching Authority, dated Aug. 19, 2015 in connection with PCT International Application No. PCT/US2015/031358, filed May 18, 2015.
Oct. 22, 2014 Amendment in response to May 22, 2014 Notice of Missing Requirements in connection with U.S. Appl. No. 13/994,431.
Preliminary Amendment filed Feb. 17, 2015 in connection with U.S. Appl. No. 13/994,431.
Office Action dated Sep. 21, 2007 in connection with U.S. Appl. No. 10/380,256.
Office Action dated Dec. 20, 2006 in connection with U.S. Appl. No. 10/702,203.
Amendment filed May 21, 2007 in response to Office Action dated Dec. 20, 2006 in connection with U.S. Appl. No. 10/702,203.
Issue Notification dated Mar. 18, 2008 in connection with U.S. Appl. No. 10/702,203.
Office Action dated Jul. 10, 2009 in connection with U.S. Appl. No. 11/810,509.
Jan. 11, 2010 Amendment in response to Office Action dated Jul. 10, 2009 in connection with U.S. Appl. No. 11/810,509.
Jan. 26, 2010 Supplemental Amendment in connection with U.S. Appl. No. 11/810,509.
Notice of Allowance and Fee(s) Due dated Apr. 2, 2010 in connection with U.S. Appl. No. 11/810,509.
Office Action dated Jun. 24, 2008 in connection with U.S. Appl. No. 11/894,690.
Amendment filed Oct. 16, 2008 in response to Office Action dated Jun. 24, 2008 in connection with U.S. Appl. No. 11/894,690.

(56) References Cited

OTHER PUBLICATIONS

Supplemental Amendment filed Jan. 16, 2009 in connection with U.S. Appl. No. 11/894,690.
Notice of Allowance dated Feb. 24, 2009 in connection with U.S. Appl. No. 11/894,690.
Office Action dated Jun. 5, 2009 in connection with U.S. Appl. No. 11/894,690.
Nov. 5, 2009 Amendment in response to Office Action dated Jun. 5, 2009 in connection with U.S. Appl. No. 11/894,690.
Office Action dated Sep. 3, 2008 in connection with U.S. Appl. No. 11/894,808.
Dec. 19, 2008 Amendment in response to Office Action dated Sep. 3, 2008 in connection with U.S. Appl. No. 11/894,808.
Notice of Allowance dated Mar. 23, 2009 in connection with U.S. Appl. No. 11/894,808.
Amendment after Notice of Allowance filed Jun. 23, 2009 in connection with U.S. Appl. No. 11/894,808.
Office Action dated Oct. 28, 2010 in connection with U.S. Appl. No. 12/804,284.
Office Action dated Feb. 4, 2011 in connection with U.S. Appl. No. 12/804,284.
Aug. 4, 2011 Amendment in response to Office Action dated Feb. 4, 2011 in connection with U.S. Appl. No. 12/804,284.
Notice of Allowance dated Sep. 1, 2011 in connection with U.S. Appl. No. 12/804,284.
Office Action dated May 8, 2012 in connection with U.S. Appl. No. 13/339,089.
Notice of Abandonment dated Nov. 14, 2012 in connection with U.S. Appl. No. 13/339,089.
Notice of Abandonment dated Sep. 13, 2013 in connection with U.S. Appl. No. 13/672,437.
Office Action dated Dec. 1, 2014 in connection with U.S. Appl. No. 13/959,660.
Amendment filed Feb. 27, 2015 in connection with U.S. Appl. No. 13/959,660.
Notice of Allowance dated May 3, 2015 in connection with U.S. Appl. No. 13/959,660.
Official Action dated Mar. 17, 2009 in connection with Canadian Patent Application No. CA 2425112 OA.
Sep. 17, 2009 Response to Official Action dated Mar. 17, 2009 in connection with Canadian Patent Application No. CA 2425112 OA.
Official Action dated Mar. 16, 2010 in connection with Canadian Patent Application No. CA 2425112 OA.
Sep. 16, 2010 Response to Official Action dated Mar. 16, 2010 in connection with Canadian Patent Application No. CA 2425112 OA.
Supplementary European Search Report dated Feb. 16, 2004 in connection with European Patent Application No. 01977533.
Communication Pursuant to Article 94(3) EPC dated Mar. 30, 2005 in connection with European Patent Application No. 01977533.7.
Oct. 10, 2005 Response to Communication Pursuant to Article 94(3) EPC issued Mar. 30, 2005 in connection with European Patent Application No. 01977533.7.
Communication Pursuant to Article 94(3) EPC dated Nov. 16, 2005 in connection with European Patent Application No. 01977533.7.
Mar. 22, 2006 Response to Communication Pursuant to Article 94(3) EPC dated Nov. 16, 2005 in connection with European Patent Application No. 01977533.7.
Sep. 24, 2008 Response to Official Action dated Mar. 14, 2008 in connection with European Patent Application No. 07004522.4.
Nov. 10, 2009 Response to Communication Pursuant to Article 94(3) EPC dated Apr. 30, 2009 in connection with European Patent Application No. 07004522.4.
Communication Pursuant to Article 94(3) EPC dated Jun. 10, 2010 in connection with European Patent Application No. 07004522.4.
Oct. 20, 2010 Response to Communication Pursuant to Article 94(3) EPC dated Jun. 10, 2012 in connection with European Patent Application No. 07004522.4.
Communication Pursuant to Article 94(3) EPC dated Apr. 1, 2011 in connection with European Patent Application No. 07004522.4.
Oct. 11, 2011 Response to Communication Pursuant to Article 94(3) EPC dated Apr. 1, 2011 in connection with European Patent Application No. 07004522.4.
Communication Pursuant to Article 94(3) EPC dated May 24, 2012 in connection with European Patent Application No. 07004522.4.
Nov. 30, 2012 Response to Communication Pursuant to Article 94(3) EPC dated May 24, 2012 in connection with European Patent Application No. 07004522.4.
Communication Pursuant to Article 94(3) EPC dated Jun. 12, 2013 in connection with European Patent Application No. 07004522.4.
Dec. 31, 2013 Response to Communication Pursuant to Article 94(3) EPC dated Jun. 12, 2013 in connection with European Patent Application No. 07004522.4.
Jul. 9, 2014 Communication accompanying Summons to Attend Oral Proceedings in connection with European Patent Application No. 07004522.4.
Jan. 2, 2015 Written Submission in connection with European Patent Application No. 07004522.4.
Jan. 15, 2015 Communication in connection with European Patent Application No. 07004522.4.
Jan. 29, 2015 Written Submission in connection with European Patent Application No. 07004522.4.
Feb. 5, 2015 Communication in connection with European Patent Application No. 07004522.4.
Mar. 23, 2015 Decision of Refusal in connection with European Patent Application No. 07004522.4.
Jun. 1, 2015 Notice of Appeal in connection with European Patent Application No. 07004522.4.
Aug. 3, 2015 Statement of Grounds of Appeal in connection with European Patent Application No. 07004522.4.
European Search Report dated May 18, 2016 in connection with EP 15195765.1.
May 24, 2016 Communication Pursuant to Article 94(3) EPC issued by the EPO in connection with EP 15195765.1.
International Search Report dated Jan. 23, 2002 in connection with PCT/US01/28967.
International Preliminary Examination Report dated Feb. 25, 2003 in connection with PCT/US01/28967.
International Search Report dated May 13, 2002 in connection with PCT/US01/31243.
International Preliminary Examination Report dated Jun. 13, 2003 in connection with PCT/US01/31243.
Akeson, M., Branton, D., Kasianowicz, J. J., Brandin, E., and Deamer, D.W. (1999) "Microsecond time-scale discrimination between polycytidylic acid and polyadenylic acid segments wtihin single RNA molecules" Biophys. J. 77:3227-3233.
Aksimentiev, A. et al. (2004) "Microscopic Kinetics of DNA Translocation through Synthetic Nanopores" Biophysical Jouranl 87:2086-2097.
Anderson, Sequencing and the single channel. Biophys J. Dec. 1999; 77(6):2899-901.
Arbo et al. (1993) "Solid Phase Synthesis of Protected Peptides Using New Cobalt (III) Amine Linkers," Int. J. Peptide Protein Res. 42:138-154.
Ashkenasy et al. Recognizing a single base in an individual DNA strand: a step toward DNA sequencing in nanopores. Angew Chem Int Ed Engl. Feb. 18, 2005; 44(9):1401-4.
Atanasnov et al. Membrane on a chip: a functional tethered lipid bilayer membrane on silicon oxide surfaces. Biophys J. Sep. 2005; 89(3):1780-8.
Axelrod V.D. et al. (1978) "Specific termination of RNA polymerase synthesis as a method of RNA and DNA sequencing," Nucleic Acids Res. 5(10):3549-3563.
Baaken et al. Planar microelectrode-cavity array for high-resolution and parallel electrical recording of membrane ionic currents. Lab Chip. Jun. 2008; 8(6):938-44. Epub Apr. 16, 2008.
Badman, E. R. et al. (2000) "A Parallel Miniature Cylindrical Ion Trap Array," Anal. Chem (2000) 72:3291-3297.
Badman, E. R. et al. (2000) "Cylindrical Ion Trap Array with Mass Selection by Variation in Trap Dimensions," Anal. Chem. 72:5079-5086.

(56) References Cited

OTHER PUBLICATIONS

Bai et al. (2003) "Photocleavage of a 2-nitrobenzyl Linker Bridging a Fluorophore to the 5' end of DNA," PNAS, vol. 100, No. 2, pp. 409-413.

Bai, X., Kim, S., Li Z., Turro, N.J. and Ju, J. (2004) "Design and Synthesis of a Photocleavable Biotinylated Nucleotide for DNA Analysis by Mass Spectrometry," Nucleic Acids Research, 32(2):534-541.

Benner, et al. Sequence-specific detection of individual DNA polymerase complexes in real time using a nanopore. Nat Nanotechnol. Nov. 2007; 2(11):718-24. Epub Oct. 28, 2007.

Benson, S.C. et al., (1993) "Heterodimeric DNA-binding dyes designed for energy transfer: stability and applications of the DNA complexes," Nucleic Acids Res. 21:5720-5726.

Bergmann et al. (1995) "Allyl as Internucleotide Protecting Group in DNA Synthesis to be Cleaved Off by Ammonia," Tetrahedron, 51:6971-6976.

Bergseid M., Baytan A.R., Wiley J.P., Ankener W.M., Stolowitz, Hughs K.A., and Chestnut J.D. (2000) "Small-molecule base chemical affinity system for the purification of proteins," BioTechniques 29:1126-1133.

Bezrukov, S.M., and Kasianowicz, J.J. (2001) "Neutral Polymers in the nanopores of alamethicin and alpha-hemolysin." Biologicheskie Membrany 18:451-455.

Bi, L., Kim D.H., and Ju, J. (2006) "Design and Synthesis of a Chemically Cleavable Fluorescent Nucleotide, 3"-O- Allyl-dGTP-allyl-Bodipy-FL-510, as a Reversible Terminator for DNA Sequencing by Synthesis" J. Am. Chem. Soc., 128:2542-2543.

Boireau et al. Unique supramolecular assembly of a redox protein with nucleic acids onto hybrid bilayer: towards a dynamic DNA chip. Biosens Bioelectron. Feb. 15, 2005; 20(8):1631-7.

Bokhari, S.H. et al. (2005) "A Parallel Graph Decomposition Algorithm for DNA Sequencing with Nanopores" Bioinformatics 21(7):889-896.

Braslavsky I.; Hebert, B.; Kartalov, E.; et al. (2003) "Sequence information can be obtained from single DNA molecules." Proc. Natl. Acad. Sci. 100(7):3960-3964.

Brunckova, J. et al. (1994) "Intramolecular Hydrogen Atom Abstrction in Carbohydrates and Nucleosides: Inversion of an α- to β-Mannopyranoside and Generation of Thymidine C-4' Radicals." Tetrahedron Letters, vol. 35, pp. 6619-6622.

Buchmann, M. B. (2004) "Electrochemical release from gold-thiolate electrodes for controlled insertion of ion channels into bilayer membranes," Bioorganic & Med Chem 12 (2004) 1315-1324.

Buck, G.A. et al. (1999) "Design Strategies and Performance of Custom DNA Sequencing Primers," BioTechniques 27(3):528-536.

Burgess, K. et al. (1997) "Photolytic Mass Laddering for Fast Characterization of Oligomers on Single Resin Beads," J. Org. Chem. 62:5662-5663.

Buschmann et al. (1999) "The Complex Formation of alpha,omega-Dicarboxylic Acids and alpha,omega—Diols with Cucurbituril and alpha-Cyclodextrin," Acta Chim. Slov. 46(3):405-411.

Buschmann et al. (2003) "Spectroscopic Study and Evaluation of Red-Absorbing Fluorescent Dyes," Bioconjugate Chem., 14:195-204.

Butler, et al. Determination of RNA orientation during translocation through a biological nanopore. Biophys J. Jan. 1, 2006; 90(1):190-9. Epub Oct. 7, 2005.

Butler, et al. Ionic current blockades from DNA and RNA molecules in the alpha-hemolysin nanopore. Biophys J. Nov. 1, 2007; 93(9):3229-40. Epub Aug. 3, 2007.

Caetano-Anolies (1994) "DNA Amplification Fingerprinting Using Arbitrary Mini-hairpin Oligonucleotide Primers." Nature Biotechnology, 12:619-623.

Canard B. et al. (1994) "DNA polymerase fluorescent substrates with reversible 3'-tags," Gene, 148:1-6.

Canard B. et al. (1995) "Catalytic editing properties of DNA polymerases," Proc. Natl. Acad. Sci. USA 92:10859-10863.

Caruthers, M.H. (1985) "Gene synthesis machines: DNA chemistry and its uses," Science 230:281-285.

Chandler, E.L et al. (2004) "Membrane Surface Dynamics of DNA-Threaded Nanopores Revealed by Simultaneous Single-Molecule Optical and Ensemble Electrical Recording." Langmuir 20:898-905.

Chee, M. et al. (1996) "Accessing genetic information with high density DNA arrays," Science 274:610-614.

Chen X. and Kwok, P.-Y. (1997) "Template-directed dye-terminator incorporation (TDI) assay: a homogeneous DNA diagnostic method based on fluorescence resonance energy transfer," Nucleic Acids Res. 25:347-353.

Chen et al. (2010) "Reconstructed evolutionary adaptive paths give polymerases accepting reversible terminators for sequencing and SNP detection" Proc. Natl. Acad. Sci. U.S.A., 107:1948-53.

Chiu, N.H., Tang, K., Yip, P., Braun, A., Koster, H., and Cantor, C.R. (2000) "Mass spectrometry of single-stranded restriction fragments captured by an undigested complementary sequence," Nucleic Acids Res. 28:E31.

Clarke, et al. "Continuous base identification for single-molecule nanopore DNA sequencing" Nat Nanotechnol. Apr. 2009; 4(4):265-70. Epub Feb. 22, 2009.

Cockroft, et al. A single-molecule nanopore device detects DNA polymerase activity with single-nucleotide resolution. J Am Chem Soc. Jan. 23, 2008; 130(3):818-20. Epub Jan. 1, 2008.

Collins, F.S. et al. (2003) "A vision for the future of genomics research." Nature. 422(6934):835-47.

Collins, F. S.; Morgan, M.; Patrinos, A. (2003) "The Human Genome Project: Lessons from Large-Scale Biology." Science, 300, pp. 286-290.

Crespo-Hernandez et al., (2000) "Part 1. Photochemical and Photophysical Studies of Guanine Derivatives: Intermediates Contributing to its Photodestruction Mechanism in Aqueous Solution and the Participation of the Electron Adduct," Photochemistry and Photobiology, 71(5):534-543.

Danleon, et al. Cell membranes suspended across nanoaperture arrays. Langmuir. Jan. 3, 2006; 22(1):22-5.

Deamer, D.W. et al (2002) "Characterization of nucleic acids by nanopore analysis." Acc. Chem. Res. 35(10):817-825.

Eid et al. (2008) "Real-time DNA sequencing from single polymerase molecule" Science 323:133-138.

Elango, N. et al. (1983) "Amino Acid Sequence of Human Respiratory Syncytial Virus Nucleocapsid Protein," Nucleic Acids Research 11(17):5941-5951.

Ervin, et al. Simultaneous alternating and direct current readout of protein ion channel blocking events using glass nanopore membranes. Anal Chem. Mar. 15, 2008; 80(6):2069-76 Epub Feb. 23, 2008.

Fallahpour, R.A. (2000) "Photochemical and Thermal reactions of Azido-Oligopyridines: Diazepinones, a New Class of Metal-Complex Ligands," Helvetica Chimica Acta. 83:384-393.

Fei, Z. et al. (1998) "MALDI-TOF mass spectrometric typing of single nucleotide polymorphisms with mass-tagged ddNTPs," Nucleic Acids Research 26(11) :2827-2828.

Finzi, L. et al. (1995) "Measurement of Lactose Repressor-Mediated Loop Formation and Breakdown in Single DNA Molecules." Science, 267:378-380.

Flusberg, et al. Direct detection of DNA methylation during single-molecule, real-time sequencing. Nat Methods. Jun. 2010; 7(6):461-5. Epub May 9, 2010.

Fologea, D. et al. (2005) "Slowing DNA Translocation in a Solid State Nanopore" Nano Letters 5(9), 1734-1737.

Fologea, D. et al. (2005) "Detecting Single Stranded DNA with a Solid State Nanopore" Nano Letters 5(10):1905-1909.

Fuller et al. (2009) "The challenges of sequencing by synthesis" Nat Biotechnol 27:1013-1023.

Gibson, K.J. et al. (1987) "Synthesis and Application of Derivatizable Oligonucleotides," Nucleic Acids Research, 15(16): 6455-6467.

Godovikova, T.S. et al. (1999) "5-[3-(E)-(4-Azido-2,3,5,6,-tetrafluorobenzamido)propenyl-1 ]-2'deoxyuridine-5'- triphosphate Substitutes for Thymidine-5 ' triphosphate in the Polymerase Chain Reaction," Bioconjugate Chem., 10:529-537.

(56) References Cited

OTHER PUBLICATIONS

Green, T.W. et al. and Wuts, P.G.M. "Protective Groups in Organic Synthesis" 3rd ed. New York: John Wiley & Sons, Inc., 1999. 96-99, 190-191, 260-261, 542-543, and 750-751.

Griffin, T.J. et al. (1999) "Direct Genetic Analysis by Matrix-Assisted Laser Desorption/Ionization Mass Spectrometry," Proc. Nat. Acad. Sci. USA 96:6301-6306.

Guibé (1997) "Allylic Protecting Groups and Their Use in a Complex Environment Part I: Allylic Protection of Alcohols," Tetrahedron, 53:13509-13556.

Guibé (1998) "Allylic Protecting Groups and Their Use in a Complex Environment Part II: Allylic Protecting Groups and their Removal through Catalytic Palladium II-Allyl Methodology," Tetrahedron, 54:2967-3042.

Guo et al. (2008) "Four-Color DNA Sequencing With 3'-O-modified Nucletide Reversible Terminators and Chemically Cleavable Fluorescent Dideoxynucleotides", PNAS, 105:9145-9150.

Guo et al., (2010) "An Integrated System for DNA Sequencing by Synthesis Using Novel Nucleotide Analogues", Accounts of Chem. Res., 43:551-563.

Guranowski et al., (2000) "Selective Degradation of 2'-Adenlyated Diadenosine Tri- and Tetraphosphates, Ap3A and Ap4A, by Two Specific Human Dinucleoside Polyphosphate Hydrolases", Archives of Biochemistry and Biophysics, 373 (1) :218-224.

Hacia J.G., Edgemon K., Sun B., Stern D., Fodor S.A., and Collins F.S. (1998) "Two Color Hybridization Analysis Using High Density Oligonucleotide Arrays and Energy Transfer Dyes," Nucleic Acids Res. 26:3865-6.

Sep. 16, 2012 Petition for Inter Partes Review of U.S. Pat. No. 7,713,698, dated May 11, 2010.

Sep. 16, 2012 Motion to Waive Page Limit and Proposed Petition in connection with Petition for Inter Partes Review of U.S. Pat. No. 7,713,698, dated May 11, 2010.

Dec. 20, 2012 Preliminary Response under 37 C.F.R. 42.107 in connection with IPR2012-00006.

Mar. 12, 2013 Decision on Petition for Inter Partes Review in connection with IPR2012-00006.

Mar. 26, 2013 Request for Reconsideration in connection with IPR2012-00006.

Apr. 26, 2013 Opposition to Request for Reconsideration (Rehearing) Under 37 C.F.R. 42.71. (C) in connection with IPR2012-00006.

May 10, 2013 Decision on Request for Rehearing in connection with IPR2012-00006.

Aug. 30, 2013 Substitute Patent Owner Response Under 37 C.F.R. 42.120 in connection with IPR2012-00006.

Aug. 30, 2013 Substitute Patent Owner Motion to Amend Under 37 C.F.R. 42.121 in connection with IPR2012-00006.

Sep. 27, 2013 Petitioner Opposition to Motion to Amend in connection with IPR2012-00006.

Sep. 27, 2013 Petitioner Reply to Response to Petition in connection with IPR2012-00006.

Nov. 18, 2013 Substitute Patent Owner Reply on Motion to Amend in connection with IPR2012-00006.

Exhibit 1001, filed Sep. 16, 2012 in connection with IPR2012-00006: U.S. Pat. No. 7,713,698, issued May 11, 2010 to Ju et al.

Exhibit 1002, filed Sep. 16, 2012 in connection with IPR2012-00006: PCT International Application No. PCT/US90/06678 filed Oct. 26, 1990, published on May 16, 1991 as Publication No. WO 91/06678 to SRI International.

Exhibit 1003, filed Sep. 16, 2012 in connection with IPR2012-00006: Prober et al. (1987), "A System for Rapid DNA Sequencing with Fluorescent Chain-Terminating Dideoxynucleotides", *Science* vol. 238, Oct. 16, 1987, pp. 336-341.

Exhibit 1004, filed Sep. 16, 2012 in connection with IPR2012-00006: U.S. Pat. No. 5,242,796 issued Sep. 7, 1993 to Prober et al.

Exhibit 1005, filed Sep. 16, 2012 in connection with IPR2012-00006: U.S. Pat. No. 5,547,839 issued Aug. 20, 1996 to Dower et al.

Exhibit 1006, filed Sep. 16, 2012 in connection with IPR2012-00006: PCT International Application No. PCT/US96/02342 filed Feb. 21, 1996, published on Sep. 6, 1996 as Publication No. WO 96/27025 to Ely Rabani.

Exhibit 1007, filed Sep. 16, 2012 in connection with IPR2012-00006: PCT International Application No. PCT/GB00/00873 filed Mar. 10, 2000, published on Sep. 14, 2000 as Publication No. WO 00/53805 to ASM Scientific, Inc.

Exhibit 1008, filed Sep. 16, 2012 in connection with IPR2012-00006: U.S. Pat. No. 7,270,951 issued Sep. 18, 2007 to Stemple et al.

Exhibit 1009, filed Sep. 16, 2012 in connection with IPR2012-00006: U.S. Application for a Method for Direct Nucleic Acid Sequencing; U.S. Appl. No. 09/266,187, filed Mar. 10, 1999.

Exhibits 1010-1012, filed Sep. 16, 2012 in connection with IPR2012-00006: PCT International Application No. PCT/JP97/00239, filed Jan. 31, 1997, published on Aug. 6, 1998 as Publication No. WO 98/33939 to Hitachi, Ltd. with certified English translation, and Translation Affidavit.

Exhibit 1013, filed Sep. 16, 2012 in connection with IPR2012-00006: U.S. Pat. No. 5,047,519 issued Sep. 10, 1991 to Hobbs, Jr. et al.

Exhibit 1014, filed Sep. 16, 2012 in connection with IPR2012-00006: U.S. Pat. No. 4,804,748 issued Feb. 14, 1989 to Seela.

Exhibit 1015, filed Sep. 16, 2012 in connection with IPR2012-00006: U.S. Pat. No. 5,844,106 issued Dec. 1, 1998 to Seela et al.

Exhibit 1016, filed Sep. 16, 2012 in connection with IPR2012-00006: PCT International Application No. PCT/US89/02170, filed May 18, 1989, published on Nov. 30, 1989 as Publication No. WO 89/11548 to Cetus Corporation.

Exhibit 1017, filed Sep. 16, 2012 in connection with IPR2012-00006: U.S. Pat. No. 7,037,687 issued May 2, 2006 to Williams et al.

Exhibit 1018, filed Sep. 16, 2012 in connection with IPR2012-00006: U.S. Pat. No. 6,255,083 issued Jul. 3, 2001 to Williams.

Exhibit 1019, filed Sep. 16, 2012 in connection with IPR2012-00006: U.S. Pat. No. 6,001,566 issued Dec. 14, 1999 to Canard et al.

Exhibit 1020, filed Sep. 16, 2012 in connection with IPR2012-00006: PCT International Application No. PCT/GB93/00848, filed Apr. 22, 1993, published on Oct. 28, 1993 as Publication No. WO 93/21340 to Medical Research Council.

Exhibit 1021, filed Sep. 16, 2012 in connection with IPR2012-00006: Sep. 15, 2012 Declaration of George Weinstock Under Rule 37 C.F.R. §1.132.

Exhibit 1022, filed Sep. 16, 2012 in connection with IPR2012-00006: Excerpts of File History of U.S. Pat. No. 7,713,698.

Exhibit 1025, filed Apr. 30, 2013 in connection with IPR2012-00006: Columbia's Amended Complaint from *The Trustees of Columbia University in the City of New York v. Illumina, Inc.*, D. Del C.A. No. 12-376 (GMS), filed Apr. 11, 2012.

Exhibit 1026, filed Apr. 30, 2013 in connection with IPR2012-00006: Illumina's Answer to Amended Complaint from *The Trustees of Columbia University in the City of New York v. Illumina, Inc.*, D. Del C.A. No. 12-376 (GMS), filed Dec. 21, 2012.

Exhibit 1029, filed Jun. 18, 2013 in connection with IPR2012-00006: U.S. Pat. No. 4,772,691, issued Sep. 20, 1988 to Herman.

Exhibit 1030, filed Jun. 18, 2013 in connection with IPR2012-00006: Rosenblum et al., "New Dye-Labeled Terminators for Improved DNA Sequencing Patterns," Nucleic Acid Research, 1997, vol. 25, No. 22, pp. 4500-4504.

Exhibit 1031, filed Jun. 18, 2013 in connection with IPR2012-00006: PCT International Publication No. WO 99/49082, published Sep. 30, 1999 to Invitrogen Corporation.

Exhibit 1032, filed Jun. 18, 2013 in connection with IPR2012-00006: U.S. Pat. No. 5,449,767, issued Sep. 12, 1995 to Ward et al.

Exhibit 1033, filed Jun. 18, 2013 in connection with IPR2012-00006: U.S. Pat. No. 5,948,648, issued Sep. 7, 1999 to Khan et al.

Exhibit 1034, filed Jun. 18, 2013 in connection with IPR2012-00006: Jun. 8, 2013 Videotaped Deposition Transcript of George M. Weinstock, Ph.D.

(56) References Cited

OTHER PUBLICATIONS

Exhibit 1036, filed Sep. 27, 2013 in connection with IPR2012-00006: "Next Generation Genomics: World Map of High- throughput Sequencers," Sep. 1, 2013.
Exhibit 1037, filed Sep. 27, 2013 in connection with IPR2012-00006: GB Application No. 2001 0029012, filed Dec. 4, 2001 by Balasubramanian et al.
Exhibit 1039, filed Sep. 27, 2013 in connection with IPR2012-00006: Videotaped Deposition Transcript of Dr. Xiaohai Liu, Mar. 20, 2013.
Exhibit 1040, filed Sep. 27, 2013 in connection with IPR2012-00006: Excerpt from videotaped Deposition Transcript of George M. Weinstock, Ph.D., Jun. 8, 2013.
Exhibit 1041, filed Sep. 27, 2013 in connection with IPR2012-00006: Seela et al., "Oligonucleotide Duplex Stability Controlled by the 7-Substituents of 7-Deazaguanine Bases," Bioorganic & Medical Chemistry Letters, vol. 5, No. 24, pp. 3049-3052, 1995.
Exhibit 1042, filed Sep. 27, 2013 in connection with IPR2012-00006: Ramzaeva et al., "123. 7-Deazaguanine DNA: Oligonucleotides with Hydrophobic or Cationic Side Chains," Helvetica Chimica Acta, vol. 80, pp. 1809-1822, 1997.
Exhibit 1043, filed Sep. 27, 2013 in connection with IPR2012-00006: Ramzaeva et al., "88. 7-Substituted 7-Deaza-2'-deoxyguanosines: Regioselective Halogenation of Pyrrolo[2,3-d]pyrimidine Nucleosides," Helvetica Chimica Acta, vol. 78, pp. 1083-1090, 1995.
Exhibit 1044, filed Sep. 27, 2013 in connection with IPR2012-00006: Seela et al., "Duplex Stability of Oligonucleotides Containing 7-Substituted 7-Deaza- and 8-Aza-7-Deazapurine Nucleosides," Nucleosides & Nucleotides, 16(7- 9), pp. 963-966, 1997.
Exhibit 1045, filed Sep. 27, 2013 in connection with IPR2012-00006: Burgess et al., "Syntheses of Nucleosides Designed for Combinatorial DNA Sequencing," Chemistry—A European Journal, vol. 5, No. 3, pp. 951-960, 1999.
Exhibit 1046, filed Sep. 27, 2013 in connection with IPR2012-00006: U.S. Pat. No. 5,151,507, issued Sep. 29, 1992 to Hobbs, Jr. et al.
Exhibit 1047, filed Sep. 27, 2013 in connection with IPR2012-00006: U.S. Pat. No. 7,078,499, issued Jul. 18, 2006 to Odedra et al.
Exhibit 1048, filed Sep. 27, 2013 in connection with IPR2012-00006: GB Application No. 2000 0013276, filed Jun. 1, 2000 by Odedra et al.
Exhibit 1049, filed Sep. 27, 2013 in connection with IPR2012-00006: Jan. 28, 2013 Declaration of Dr. Bruce P. Branchaud in Support of Petition for Inter Partes Review of U.S. Pat. No. 7,057,026.
Exhibit 1050, filed Sep. 27, 2013 in connection with IPR2012-00006: Lee et al., "DNA sequencing with dye-labeled terminators and T7 DNA polymerase: effect of dyes and dNTPs on incorporation of dye-terminators and probability analysis of termination fragments," Nucleic Acids Research, vol. 20, No. 10, pp. 2471-2483, 1992.
Exhibit 1051, filed Sep. 27, 2013 in connection with IPR2012-00006: http://www.answers.com/topic/incubate, Accessed Sep. 27, 2013.
Exhibit 1052, filed Sep. 27, 2013 in connection with IPR2012-00006: http://en.wikipedia.org/wiki/Fluorenylmethyloxycarbonyl_chloride, Accessed Sep. 27, 2013.
Exhibit 1053, filed Sep. 27, 2013 in connection with IPR2012-00006: Sep. 27, 2013 Declaration of Kevin Burgess.
Exhibit 1054, filed Sep. 27, 2013 in connection with IPR2012-00006 : Fuji, et al., "An Improved Method for Methoxymethylation of Alcohols under Mild Acidic Conditions," Synthesis—The Journal of Synthetic Organic Chemistry, pp. 276-277, Apr. 1975.
Exhibit 2001, filed Dec. 20, 2012 in connection with IPR2012-00006: U.S. Pat. No. 5,383,858, issued Jan. 24, 1995 to Reilly et al.
Exhibit 2006, filed Apr. 26, 2013 in connection with IPR2012-00006: Dower patent with highlights.

International Search Report and the Written Opinion of the International Searching Authority, or the Declaration, including an International Search Report and Written Opinion of the International Searching Authority, dated Feb. 4, 2013 in connection with PCT International Application No. PCT/US2011/065640, filed Dec. 16, 2011.
Apr. 16, 2014 Communication transmitting Supplementary European Search Report and European Search Opinion in connection with European Patent Application No. EP 11848220.
Nov. 14, 2014 Response to Apr. 16, 2014 Communication transmitting Supplementary European Search Report and European Search Opinion in connection with European Patent Application No. EP 11848220.7.
Dec. 23, 2014 Communication pursuant to Article 94(3) EPC in connection with European Patent Application No. EP 11848220.7.
May 4, 2015 Amendment in response to Dec. 23, 2014 Communication pursuant to Article 94(3) EPC in connection with European Patent Application No. EP 11848220.7.
Jul. 15, 2015 Communication pursuant to Article 94(3) EPC in connection with European Patent Application No. EP 11848220.7.
Jan. 15, 2016 Communication Pursuant to Article 94(3) EPC in connection with European Patent Application No. EP 11848220.7.
May 12, 2016 Amendment in Response to Communication Pursuant to Article 94(3) in connection with European Patent Application No. EP 11848220.7, Ju et al.
Mar. 27, 2014 Office Action in connection with Chinese Patent Application No. 201180063978.7 (with English translation).
Aug. 11, 2014 Response to Mar. 27, 2014 Office Action in connection with Chinese Patent Application No. 201180063978.7 (with English translation of cover page only).
Dec. 22, 2014 Second Office Action in connection with Chinese Patent Application No. 201180063978.7 (with English translation of cover page only).
Mar. 6, 2015 Response to Dec. 22, 2014 Second Office Action in connection with Chinese Patent Application No. 201180063978.7.
Jul. 13, 2015 Third Office Action in connection with Chinese Patent Application No. 201180063978.7 (with English translation of cover page only).
Sep. 28, 2015 Response to Jul. 13, 2015 Office Action issued in connection with Chinese Patent Application No. 200780028545.1.
Jan. 29, 2016 Office Action issued in connection with Chinese Patent Application No. 200780028545.1.
Mar. 31, 2016 Response to Jan. 29, 2016 Office Action, issued in connection with Chinese Application No. 200780028545.1, Ju et al.
International Search Report and Written Opinion of the International Searching Authority dated Oct. 25, 2013 in connection with PCT International Application No. PCT/US2013/035635.
Invitation to Pay Additional Fees mailed by the International Searching Authority dated Aug. 19, 2013 connection with PCT International Application No. PCT/US2013/035635.
Office Action dated Jul. 15, 2015 by the Chinese State Intellectual Property Office in connection with Chinese Patent Application No. 201380025837.5.
Response to the Jul. 15, 2015 Office Action, filed Jan. 29, 2016 in connection with Chinese Patent Application No. 201380025837.5.
May 4, 2016 Office Action issued by the Chinese State Intellectual Property Office in connection with Chinese Patent Application No. 201380025837.5.
Communication pursuant to Rule 164(1) EPC dated Dec. 7, 2015 by the EPO in connection with EP 13775787.8.
Extended European Search Report dated Mar. 11, 2016 by the EPO in connection with EP 13775787.8.
Mar. 16, 2016 Restriction Requirement Issued by the USPTO in connection with U.S. Appl. No. 14/391,337, Ju et al.
International Search Report and Written Opinion of the International Searching Authority dated Sep. 24, 2013 in connection with PCT International Application No. PCT/US2013/035630.
Communication pursuant to Rule 164(1) EPC dated by Dec. 2, 2015 by the EPO in connection with EP 13807639.3.
Extended European Search Report dated Mar. 11, 2016 by the EPO in connection with EP 13807639.3.
Amendment to Notice of Insufficiency, filed Dec. 31, 2015 in connection with U.S. Appl. No. 14/776,461.

(56) References Cited

OTHER PUBLICATIONS

International Search Report and Written Opinion of the International Searching Authority dated Jul. 30, 2014 in connection with PCT International Application No. PCT/US2014/029495.
Voluntary Amendment filed Mar. 17, 2016 in connection with Chinese Patent Application No. CN 2014800159374.
Voluntary Amendment filed May 12, 2016 in connection with European Patent Application No. EP14764268.0, Ju et al.
Aug. 5, 2015 Applicant Statement in connection with U.S. Appl. No. 14/666,124 regarding Amendments to p. 40 Regarding Tagged Nucleotides.
International Search Report and Written Opinion of the International Searching Authority dated Jun. 29, 2015 in connection with PCT International Application No. PCT/US2015/022063.
International Search Report and Written Opinion of the International Searching Authority dated Aug. 25, 2015 in connection with PCT International Application No. PCT/US2015/015647.
Sep. 16, 2012 Petition for Inter Partes Review of U.S. U.S. Pat. No. 7,790,869.
Sep. 17, 2012 Motion to Waive Page Limit and Proposed Petition in connection with Petition for Inter Partes Review of U.S. Pat. No. 7,790,869.
Dec. 21, 2012 Preliminary Response under 37 C.F.R. 42.107 in connection with IPR2012-00007.
Mar. 12, 2013 Decision on Petition for Inter Partes Review in connection with IPR2012-00007.
Mar. 26, 2013 Request for Reconsideration in connection with IPR2012-00007.
Mar. 26, 2013 Request for Rehearing under 37 C.F.R. 42.71 of Decision to Institute Inter Partes Review in connection with IPR2012-00007.
Apr. 26, 2013 Opposition to Request for Reconsideration (Rehearing) Under 37 C.F.R. 42.71. (C) in connection with IPR2012-00007.
May 10, 2013 Decision on Request for Rehearing in connection with IPR2012-00007.
Aug. 30, 2013 Substitute Patent Owner Response Under 37 C.F.R. 42.120 in connection with IPR2012-00007.
Aug. 30, 2013 Substitute Patent Owner Motion to Amend Under 37 C.F.R. 42.121 in connection with IPR2012-00007.
Sep. 27, 2013 Petitioner Opposition to Motion to Amend in connection with IPR2012-00007.
Sep. 27, 2013 Petitioner Reply to Response to Petition in connection with IPR2012-00007.
Nov. 18, 2013 Substitute Patent Owner Reply on Motion to Amend in connection with IPR2012-00007.
Exhibit 1001, filed Sep. 16, 2012 in connection with IPR2012-00007: U.S. Pat. No. 7,790,869 issued Sep. 7, 2010 to Ju et al.
Exhibit 1022, filed Sep. 16, 2012 in connection with IPR2012-00007: Excerpts of File History of U.S. Pat. No. 7,790,869.
Exhibit 1053, filed Sep. 27, 2013 in connection with IPR2012-00007: Sep. 27, 2013 Declaration of Kevin Burgess.
Exhibit 2001, filed Dec. 21, 2012 in connection with IPR2012-00007: Composition of a Nucleotide.
Exhibit 2033, filed Aug. 30, 2013 in connection with IPR2012-00007: Jun. 25, 2013 Substitute Declaration of Dr. George L. Trainor [redacted].
Nov. 12, 2013 Petitioner Motion to Exclude Evidence in connection with IPR2012-00007.
Nov. 12, 2013 Patent Owner Motion for Observations on the Cross-Examination Testimony of Kevin Burgess, Ph.D. in connection with IPR2012-00007.
Nov. 12, 2013 Patent Owner Motion to Exclude Evidence in connection with IPR2012-00007.
Nov. 26, 2013 Petitioner's Response to Motion for Observations in connection with IPR2012-00007.
Nov. 26, 2013 Patent Owner's Opposition to Petitioner's Motion to Exclude in connection with IPR2012-00007.
Nov. 26, 2013 Petitioner's Opposition to Motion to Exclude in connection with IPR2012-00007.
Dec. 3, 2013 Petitioner Reply to Patent Owner's Opposition to Motion to Exclude in connection with IPR2012-00007.
Dec. 3, 2013 Patent Owner Reply on Motion to Exclude in connection with IPR2012-00007.
Mar. 6, 2014 Final Written Decision in connection with IPR2012-00007.
Oct. 3, 2012 Petition for Inter Partes Review of U.S. Pat. No. 8,088,575.
Oct. 3, 2012 Motion to Waive Page Limit and Proposed Petition in connection with Petition for Inter Partes Review of U.S. Pat. No. 8,088,575.
Jan. 7, 2013 Preliminary Response under 37 C.F.R. 42.107 in connection with IPR2013-00011.
Mar. 12, 2013 Decision on Petition for Inter Partes Review in connection with IPR2013-00011.
Mar. 26, 2013 Request for Reconsideration in connection with IPR2013-00011.
Mar. 26, 2013 Request for Rehearing under 37 C.F.R. 42.71 of Decision to Institute Inter Partes Review in connection with IPR2013-00011.
Apr. 26, 2013 Opposition to Request for Reconsideration (Rehearing) Under 37 C.F.R. 42.71. (C) in connection with IPR2013-00011.
May 10, 2013 Decision on Request for Rehearing in connection with IPR2013-00011.
Jun. 25, 2013 Motion to Amend Under 37 C.F.R. 42.121 in connection with IPR2013-00011.
Aug. 30, 2013 Substitute Patent Owner Response Under 37 C.F.R. 42.120 in connection with IPR2013-00011.
Sep. 27, 2013 Petitioner Opposition to Motion to Amend in connection with IPR2013-00011.
Sep. 27, 2013 Petitioner Reply to Response to Petition in connection with IPR2013-00011.
Nov. 18, 2013 Substitute Patent Owner Reply on Motion to Amend in connection with IPR2013-00011.
Exhibit 1001, filed Oct. 3, 2012 in connection with IPR2013-00011: U.S. Pat. No. 8,088,575 issued Jan. 3, 2012 to Ju et al.
Exhibit 1021, filed Oct. 3, 2012 in connection with IPR2013-00011: Oct. 2, 2012 Declaration of George Weinstock Under Rule 37 C.F.R. §1.132.
Exhibit 1022, filed Oct. 3, 2012 in connection with IPR2013-00011: Excerpts of File History of U.S. Pat. No. 8,088,575.
Exhibit 1053, filed Sep. 27, 2013 in connection with IPR2013-00011: Sep. 27, 2013 Declaration of Kevin Burgess.
Exhibit 2033, filed Aug. 30, 2013 in connection with IPR2013-00011: Jun. 25, 2013 Substitute Declaration of Dr. George L. Trainor [redacted].
Nov. 12, 2013 Petitioner Motion to Exclude Evidence in connection with IPR2013-00011.
Nov. 12, 2013 Patent Owner Motion for Observations on the Cross-Examination Testimony of Kevin Burgess, Ph.D. in connection with IPR2013-00011.
Nov. 12, 2013 Patent Owner Motion to Exclude Evidence in connection with IPR2013-00011.
Nov. 26, 2013 Petitioner's Response to Motion for Observations in connection with IPR2013-00011.
Nov. 26, 2013 Patent Owner's Opposition to Petitioner's Motion to Exclude in connection with IPR2013-00011.
Nov. 26, 2013 Petitioner's Opposition to Motion to Exclude in connection with IPR2013-00011.
Dec. 3, 2013 Petitioner Reply to Patent Owner's Opposition to Motion to Exclude in connection with IPR2013-00011.
Dec. 3, 2013 Patent Owner Reply on Motion to Exclude in connection with IPR2013-00011.
Mar. 6, 2014 Final Written Decision in connection with IPR2013-00011.
*Trustees of Columbia University in the City of New York v. Illumina, Inc.*, Nos. 2014-1547, 2014-1548, and 2014-1550 (Fed. Cir. Jul. 17, 2015).
Exhibit 2010, filed Jun. 24, 2013 in connection with IPR2012-00006: U.S. Pat. No. 8,088,575 (filed Jul. 19, 2010, issued Jan. 3, 2012) (Exhibit 1001 in IPR2013-00011).

(56) References Cited

OTHER PUBLICATIONS

Exhibit 2011, filed Jun. 24, 2013 in connection with IPR2012-00006: U.S. Pat. No. 7,713,698 (filed Aug. 20, 2007, issued May 11, 2010) (Exhibit 1001 in IPR2012-00006).
Exhibit 2012, filed Jun. 24, 2013 in connection with IPR2012-00006: U.S. Pat. No. 7,790,869 (filed Jun. 5, 2007, issued Sep. 7, 2010) (Exhibit 1001 in IPR2012-00007).
Exhibit 2013, filed Jun. 24, 2013 in connection with IPR2012-00006: Oct. 2, 2012 Declaration of George Weinstock Under 37 CFR 1.132 (Exhibit 1021 in IPR2013-00011).
Exhibit 2014, filed Jun. 24, 2013 in connection with IPR2012-00006: Petition for Inter Partes Review of U.S. Pat. No. 8,088,575 (Paper 4 in IPR2013-00011).
Exhibit 2015, filed Jun. 24, 2013 in connection with IPR2012-00006: Metzker et al. (1994) Termination of DNA synthesis by novel 3'-modified-deoxyribonucleoside 5'-triphosphates. Nucleic Acids Res. 22:4259-4267.
Exhibit 2016, filed Jun. 24, 2013 in connection with IPR2012-00006: Wu et al. (2007) Termination of DNA synthesis by N6-alkylated, not 3'-O-alkylated, photocleavable 2'-deoxyadenosine triphosphates. Nucleic Acids Res. 35:6339-6349.
Exhibit 2017, filed Jun. 24, 2013 in connection with IPR2012-00006: Sep. 15, 2012 Declaration of George Weinstock Under 37 CFR 1.132 (Exhibit 1021 in IPR2012-00007).
Exhibit 2018, filed Jun. 24, 2013 in connection with IPR2012-00006: Sep. 15, 2012 Declaration of George Weinstock Under 37 CFR 1.132 (Exhibit 1021 in IPR2012-00006).
Exhibit 2019, filed Jun. 24, 2013 in connection with IPR2012-00006: Definition of "DNA microarray." http://en/wikipedia.org/wiki/DNA_microarray.
Exhibit 2020, filed Jun. 24, 2013 in connection with IPR2012-00006: Brettin et al. (2005) Expression capable library for studies of Neisseria gonorrhoeae, version 1.0 BMC Microbiology. 5:50.
Exhibit 2021, filed Jun. 24, 2013 in connection with IPR2012-00006: George M. Weinstock, Handbook of Molecular Microbial Ecology, vol. 1—Chapter 18: The Impact of Next-Generation Sequencing Technologies on Metagenomics 141-147 Frans J. de Bruijn ed., John Wiley & Sons, Inc. (2011).
Exhibit 2022, filed Jun. 24, 2013 in connection with IPR2012-00006: Sep. 16, 2012 Petition for Inter Partes Review of U.S. Pat. No. 7,713,698 (Paper 3 in IPR2012-00006).
Exhibit 2023, filed Jun. 24, 2013 in connection with IPR2012-00006: Sep. 16, 2012 Petition for Inter Partes Review of U.S. Pat. No. 7,790,869 (Paper 5 in IPR2012-00007).
Exhibit 2024, filed Jun. 24, 2013 in connection with IPR2012-00006: Maxam and Gilbert (1977) A new method for sequencing DNA, Proc. Natl. Acad. Sci. USA. 74:560-564..
Exhibit 2025, filed Jun. 24, 2013 in connection with IPR2012-00006: Sanger et al. (1977) DNA sequencing with chain-terminating inhibitors, Proc. Natl. Acad. Sci. USA. 74:5463-5467.
Exhibit 2026, filed Jun. 24, 2013 in connection with IPR2012-00006: Pennisi (2000) DOE Team Sequences Three Chromosomes, Science. 288:417-419.
Exhibit 2027, filed Jun. 24, 2013 in connection with IPR2012-00006: Welch and Burgess (1999) Synthesis of Fluorescent, Photolabile 3'-O-Protected nucleoside Triphosphates for the Base Addition Sequencing Scheme, nucleosides & Nucleotides. 18:197-201.
Exhibit 2028, filed Jun. 24, 2013 in connection with IPR2012-00006: Hyman (1998) A New Method of Sequencing DNA, Analytical Biochemistry 174:423-436.
Exhibit 2029, filed Jun. 24, 2013 in connection with IPR2012-00006: U.S. Pat. No. 5,302,509 (filed Feb. 27, 1991, issued Apr. 12, 1994).
Exhibit 2030, filed Jun. 24, 2013 in connection with IPR2012-00006: Canard and Sarfati (1994) DNA polymerase fluorescent substrates with reversible 3'-tags, Gene. 148:1-6.
Exhibit 2031, filed Jun. 24, 2013 in connection with IPR2012-00006: U.S. Pat. No. 8,399,188 (filed Sep. 4, 2007, issued Mar. 19, 2013).
Exhibit 2032, filed Jun. 24, 2013 in connection with IPR2012-00006: Sarfati et al. (1987) Synthesis of Fluorescent or Biotinylated Nucleoside Compounds, Tetrahedron Letters. 43:3491-3497.
Exhibit 2033, filed Aug. 30, 2013 in connection with IPR2012-00006: Jun. 25, 2013 Substitute Declaration of Dr. George L. Trainor [redacted].
Exhibit 2034, filed Jun. 25, 2013 in connection with IPR2012-00006: Jingyue Ju et. al. (2006) Four-color DNA sequencing by synthesis using cleavable fluorescent nucleotide reversible terminators, Proceedings of the National Academy of Sciences. 103: 19635-19640.
Exhibit 2035, filed Jun. 25, 2013 in connection with IPR2012-00006: Batista et al. (2008) PRG-1 and 21U-RNAs Interact to Form the piRNA Complex Required for Fertility in C. elegans. Molecular Cell 31:1-12.
Exhibit 2036, filed Jun. 25, 2013 in connection with IPR2012-00006: Form 7 Review Context and Analysis, Biomedical Engineering and Research to Aid Persons with Disabilities Programs Dec. 19-20, 2000 Panel Review, Fluorescence Imaging Chip System for Massive Parallel DNA Sequencing. Proposal No. BES-0097793.
Exhibit 2037, filed Jun. 25, 2013 in connection with IPR2012-00006: Oct. 1, 2006 Request for opinion on manuscript by J. Ju et. al., Proceedings of National Academy of Sciences, U.S.A.
Exhibit 2038, filed Jun. 25, 2013 in connection with IPR2012-00006: Correspondence between George Rupp, Chancellor, Columbia University and Richard T. Schlossberg, President, The David and Lucile Packard Foundation (2001).
Exhibit 2039, filed Jun. 25, 2013 in connection with IPR2012-00006: The David and Lucile Packard Foundation, Packard Fellowships for Science and Engineering, http://www.packard.org/whatwefund/conservation-and-science/packard-fellowships-for-science-andengineering/ (last visited Jun. 25, 2013).
Exhibit 2040, filed Jun. 25, 2013 in connection with IPR2012-00006: "Chemistry for Next-Generation Sequencing." http://www.illumina.com/technology/sequencing_technology.ilmn.
Exhibit 2041, filed Jun. 25, 2013 in connection with IPR2012-00006: Chiang et al. (2010) Mammalian microRNAs: experimental evaluation of novel and previously annotated genes, Genes & Dev. 24:992, 993.
Exhibit 2042, filed Jun. 25, 2013 in connection with IPR2012-00006: Seo et al. (2004) Photocleavable fluorescent nucleotides for DNA sequencing on a chip constructed by site-specific coupling chemistry, Proc. Natl Acad. Sci. 101(15):5488-5493.
Exhibit 2043, filed Jun. 25, 2013 in connection with IPR2012-00006: Curriculum vitae of Mr. Raymond S. Sims.
Exhibit 2044, filed Jun. 25, 2013 in connection with IPR2012-00006: Prior Testimony of Mr. Raymond S. Sims.
Exhibit 2045, filed Jun. 25, 2013 in connection with IPR2012-00006: Documents reviewed by Mr. Raymond S. Sims in this Proceeding.
Exhibit 2052, filed Jun. 25, 2013 in connection with IPR2012-00006: Gary Schroth Proof of Chiang Paper.
Exhibit 2074, filed Jun. 25, 2013 in connection with IPR2012-00006: Information about Dr. Ju's intellectual property sent to Illumina.
Exhibit 2090, filed Jun. 26, 2013 in connection with IPR2012-00006: IPR Default Protective Order.
Exhibit 2091, filed Jun. 26, 2013 in connection with IPR2012-00006: Declaration of Raymond S. Sims.
Exhibit 2092, filed Oct. 10, 2013 in connection with IPR2012-00006: Rough Transcript of the Sep. 4, 2013 deposition of Dr. George L. Trainor.
Exhibit 2093, filed Oct. 1, 2013 in connection with IPR2012-00006: Excerpt from Protective Groups in Organic Synthesis, 3rd Ed. (Theodora W. Greene and Peter G.M. Wuts ed., John Wiley & Sons, Inc. 1999).
Exhibit 2094, filed Oct. 1, 2013 in connection with IPR2012-00006: Final transcript of the Sep. 4-6, 2013 deposition of Dr. George L. Trainor.
Exhibit 2095, filed Oct. 1, 2013 in connection with IPR2012-00006: Final transcript of the Sep. 3, 2013 deposition of Raymond S. Sims.
Nov. 12, 2013 Petitioner Motion to Exclude Evidence in connection with IPR2012-00006.

(56) References Cited

OTHER PUBLICATIONS

Exhibit 1056, filed Nov. 19, 2013 in connection with IPR2012-00006: Videotaped Deposition Transcript of Kevin Burgess, Ph.D., Oct. 28, 2013, signed with errata.
Nov. 12, 2013 Patent Owner Motion for Observations on the Cross-Examination Testimony of Kevin Burgess, Ph.D. in connection with IPR2012-00006.
Nov. 12, 2013 Patent Owner Motion to Exclude Evidence in connection with IPR2012-00006.
Exhibit 2099, filed Nov. 12, 2013 in connection with IPR2012-00006: Welch, M., et al (2005) Corrigenda to Syntheses of Nucleosides Designed for Combinatorial DNA Sequencing Chem. Eur.J., 1999, 951-960. Published in Chem. Eur. J, 2005, 11, 7136-7145.
Exhibit 2100, filed Nov. 12, 2013 in connection with IPR2012-00006: Welch, M (1999) "Base Additions Sequencing Scheme (BASS) and Studies Toward New Sequencing Methodologies." PhD. Dissertation, Texas A&M University.
Exhibit 2101, filed Nov. 12, 2013 in connection with IPR2012-00006: Lu and Burgess (2006) "A Diversity Oriented Synthesis of 3'-O-modified nucleoside triphosphates for DNA 'Sequencing by Synthesis'." Bioorganic & Medicinal Chemistry Letters, 16, 3902-3905.
Exhibit 2102, filed Nov. 12, 2013 in connection with IPR2012-00006: Advanced Sequencing Technology Awards 2004. http://www.genome.gov/12513162 (accessed Oct. 14, 2013).
Exhibit 2103, filed Nov. 12, 2013 in connection with IPR2012-00006: Welch and Burgess (2006) Erratum to Synthesis of Fluorescent, Photolabile 3'-O-Protected Nucleoside Triphosphates for the Base Addition Sequencing Scheme, Nucleosides & Nucleotides,18:197-201. Published in Nucleosides, Nucleotides and Nucleic Acids, 25:1, 119.
Nov. 26, 2013 Petitioner Response to Motion for Observations in connection with IPR2012-00006.
Nov. 26, 2013 Patent Owner Opposition to Petitioner's Motion to Exclude in connection with IPR2012-00006.
Nov. 26, 2013 Petitioner Opposition to Motion to Exclude in connection with IPR2012-00006.
Dec. 3, 2013 Petitioner Reply to Patent Owner's Opposition to Motion to Exclude in connection with IPR2012-00006.
Dec. 3, 2013 Patent Owner Reply on Motion to Exclude in connection with IPR2012-00006.
Exhibit 2105, filed Dec. 15, 2013 in connection with IPR2012-00006: Columbia's Demonstratives Under 42.70(b) for Dec. 17, 2013 Oral Hearing in connection with IPR2012-00006, IPR2012-00007, and IPR2013-00011.
Exhibit 1057, filed Dec. 16, 2013 in connection with IPR2012-00006: Illumina's Invalidity Demonstratives for Final Hearing Dec. 17, 2013 in connection with IPR2012-00006, IPR2012-00007, and IPR2013-00011.
Feb. 10, 2014 Record of Dec. 17, 2013 Oral Hearing in connection with IPR2012-00006, IPR2012-00007, and IPR2013-00011.
Mar. 6, 2014 Final Written Decision in connection with IPR2012-00006.
Margulies, M.; Egholm, M.; Altman, W. E. (2005) "Genome Sequencing in Microfabricated High-Density Picolitre Reactors . " Nature, 437:376-380.
Markiewicz et al. (1997) "A new method of synthesis of fluorescently labeled oligonucleotides and their application in DNA sequencing," Nucleic Acids Research, 25:3672-3690.
Marquez et al. (2003) "Selective Fluorescence Quenching of 2,3-Diazabicyclo [2.2.2]oct-2-ene by Nucleotides," Organic Letters, 5:3911-3914.
Mathe, J. et al. (2004) "Nanopore Unzipping of Individual Hairpin Molecules" Biophysical Journal 87:3205-3212.
Mathews C.K. et al. (1985) "Chemical Synthesis of Oligonucleotides," Biochemistry, 2nd Edition, pp. 127-128.
Mauer et al. Reconstitution of ion channels in agarose-supported silicon orifices. Biosens Bioelectron. May 15, 2007; 22 (11) :2577-84 . Epub Nov. 13, 2006.

Mcnally et al. Optical recognition of converted DNA nucleotides for single-molecule DNA sequencing using nanopore arrays. Nano Lett. Jun. 9, 2010; 10(6):2237-44.
Meller, A. et al. (2000) "Rapid nanopore discrimination between single polynucleotide molecules." Proc. Natl. Acad. Sci. USA 97:1079-1084.
Meller, A. et al. (2002) "Single Molecule Measurements of DNA Transport Through a Nanopore" Electrophoresis 23:2583-2591.
Meng et al. (2006) "Design and Synthesis of a Photocleavable Fluorescent Nucleotide 3'-O-Allyl-dGTP-PC-Biodipy-FL-510 as a Reversible Terminator for Dna Sequencing by Synthesis," J. Org. Chem 71:3248-3252.
Metzker, M.L. et al. (1994) "Termination of DNA synthesis by novel 3' modified deoxyribonucleoside 5' triphosphates," Nucleic Acids Res. 22: 4259-4267.
Metzker M.L. (2005) "Emerging Technologies in DNA Sequencing." Genome Res., 15:1767-1776.
Metzker, M.L. et al., "Sequencing Technologies—the Next Generation," Nat. Rev. Genet. 11, 31-46 (2010).
Mitra, R. D.; Shendure J.; Olejnik, J.; et al. (2003) "Fluorescent in situ sequencing on polymerase colonies." Anal. Biochem. 320:55-65.
Mohammad et al. Controlling a single protein in a nanopore through electrostatic traps. J Am Chem Soc. Mar. 26, 2008; 130(12):4081-8. Epub Mar. 6, 2008.
Monforte, J.A. and Becker, C.H. (1997) "High-throughput DNA analysis by time-of-flight mass spectrometry," Nat. Med. 3 (3) :360-362.
Morozova, O. et al. (2009) "Applications of new sequencing technologies for transcriptome analysis" Annu Rev Genomics Hum Genet 10:135-51.
Mulder et al. (2005) "Nucleotide modification at the γ-phosphate leads to the improved fidelity of HIV-1 reverse transcriptase", Nucleic Acids Research, 33(15):4865-4873.
Nakane et al. A Nanosensor for Transmembrane Capture and Identification of Single Nucleic Acid Molecules, Biophysical Journal, vol. 87, Issue 1, Jul. 2004, pp. 615-621, ISSN 0006-3495.
Nazarenko et al. (2002) "Effect of primary and secondary structure of oligodeoxyribonucleotides on the fluorescent properties of conjugated dyes," Nucleic Acids Research, 30:2089-2095.
Nickel et al. (1992) "Interactions of Azidothymidine triphosphate with the Cellular DNA polymerases alpha, delta, and episilon and with DNA Primase," J. Biol. Chem. 267 (2):848-854.
Nie, S. et al., "Probing Single Molecules and Single Nanoparticles by Surface-Enhanced Raman Scattering," Sciencee 275, 1102-6 (1997).
Nishino et al. (1991) "Efficient Deanilidation of Phosphoranilidates by the Use of Nitrites and Acetic Anhydride." Heteroatom Chemistry, vol. 2, pp. 187-196.
Olejnik, J. et al. (1995) "Photocleavable biotin derivatives: a versatile approach for the isolation of biomolecules," Proc. Natl. Acad. Sci. USA. 92:7590-7594.
Olejnik, J. et al. (1999) "Photocleavable peptide DNA conjugates: synthesis and applications to DNA analysis using MALDI MS," Nucleic Acids Res. 27:4626-4631.
Ornelas, C., "Construction of Well-Defined Multifunctional Dendrimers Using a Trifunctional Core," Chem. Comm., 5710-5712 (2009).
Ozsolak, F. & Milos, P.M. "RNA Sequencing: Advances, Challenges, and Opportunities," Nat. Rev. Genet. 12, 87-98 (2011).
Park, J., (2009) "DNA Hybridization Sensors Based on Electrochemical Impedance Spectroscopy as a Detection Tool", Sensors vol. 9, 9513-9532; doi:10.3390/s91209513.
Park, P.J. (2009) "ChIP-seq: advantages and challenges of a maturing technology" Nat Rev Genet 10:669-680.
Pastinen et al. (1997) "Minisequencing: A Specific Tool for DNA Analysis and Diagnostics on Oligonucleotide Arrays," Genomic Res., 7:606-614.
Perkins, T.T. et al. (1994) "Relaxation of a single DNA molecule observed by optical microscopy" Science 264:822-826.
Pernodet et al (1997) "Pore size of agarose gels by atomic force microscopy" Electrophoresis 18:55-58.
Pillai (1980), "Photoremovable Protecting Groups in Organic Synthesis", Synthesis, Georg Thieme Verlag, Stuttgart, DE, vol. 1, No.

(56) References Cited

OTHER PUBLICATIONS

1 ISSN: 0039-7881, DOI: 10.1055/2-1980-28908 Pleasants, J.C. et al. (1989) "A comparative study of the kinetics of selenol/diselenide and thio/disulfide exchange reactions." JACS 111(17):6553-6558.

Pleasants, J.C. et al. (1989) "A comparative study of the kinetics of selenol/diselenide and thio/disulfide exchange reactions." JACS 111(17):6553-6558.

Pourmand N. et al. (2002) "Multiplex Pyrosequencing" Nucleic Acids Research 30(7):1-5.

Prober, J.M. et al.(1987) "A system for rapid DNA sequencing with fluorescent chain-terminating dideoxynucleotides," Science 238:336-341.

Purnell et al. Discrimination of single base substitutions in a DNA strand immobilized in a biological nanopore. ACS Nano. Sep. 22, 2009; 3(9):2533-8.

Quaedflieg et al. (1992) "An Alternative Approach Toward the Synthesis of (3'->5') Methylene Acetal Linked Dinucleosides." Tetrahedron Letters, vol. 33, pp. 3081-3084.

Rao et al. (2001) "Four Color FRET Dye Nucleotide Terminators for DNA Sequencing," Nucleosides, Nucleotides and Nucleic Acids, 20:673-676.

Rasolonjatovo et al. (1998) "6-N-(N-Methylanthranylamido)-4-Oxo-Hexanoic Acid: A New Fluorescent Protecting Group Applicable to a New DNA Sequencing Method," Nucleosides and Nucleotides, 17:2021-2025.

Reynolds et al. (2008) "Synthesis and Stability of Novel Terminal Phosphate-labeled Nucleotides", Nucleosides, Nucleotides, and Nucleic Acids, 27(1):18-30.

Rief M. (1999) "Sequence-dependent mechanics of single DNA molecules" Mat. Struct. Biol. 6:346-349.

Robertson et al., (2007) "Single-Molecule Mass Spectrometry in Solution Using a Solitary Nanopore" PNAS, 104(20):8207-8211.

Ronaghi, (1998) "PCR-Introduced Loop Structure as Primer in DNA Sequencing." BioTechniques, 25:876.

Ronaghi, M., Uhlen, M., and Nyren, P. (1998) "A Sequencing Method Based on Real-time Pyrophosphate," Science 281:364-365.

Ronaghi, M. (2001) "Pyrosequencing sheds light on DNA sequencing" Genome Res., 11:3-11.

Rosenblum, B.B. et al. (1997) "New dye-labeled terminators for improved DNA sequencing patterns," Nucleic Acids Res. 25:4500-4504.

Roskey, M.T., Juhasz, P., Smirnov, I.P., Takach, E.J., Martin, S.A., and Haff, L.A. (1996) "DNA sequencing by delayed extraction-matrix-assisted laser desorption/ionization time of flight mass spectrometry," Proc. Natl. Acad. Sci. USA. 93:4724-4729.

Ross, P.L. et al. (1997) "Discrimination of Single-Nucleotide Polymorphisms in Human DNA Using Peptide Nucleic Acid Probes Detected by MALDI-TOF Mass Spectrometry," Anal. Chem. 69:4197-4202.

Ross, P. et al. (1998) High Level Multiplex Genotyping by MALDI-TOF Mass Spectrometry. Nat. Biotech 16:1347-1351.

Rostovstev, V.V. et al. (2002) "A stepwise huisgen cycloaddition process: copper(I)-catalyzed regioselective "ligation" of azides and terminal alkynes." Angew. Chem. Int. Ed. 41(14):2596-2599.

Rotem et al., Temperature Measurement in the Intel Core Duo Processor, 2007.

Rothberg, J.M. et al. (2011) "An integrated semiconductor device enabling non-optical genome sequencing" Nature 475:348-352.

Ruparel et al. (2005) "Design and Synthesis of a 3'-O-Allyl Photocleavable Fluorescent Nucleotide as a Reversible Terminator for DNA Sequencing by Synthesis," PNAS 102(17):5932-5937.

Sanchez-Magraner, et al. Membrane insertion of *Escherichia coli* alpha-hemolysin is independent from membrane lysis. J Biol Chem. Mar. 3, 2006; 281(9):5461-7. Epub Dec. 22, 2005.

Sarfati et al., (1995) "Synthesis of fluorescent derivatives of 3'-0-(6-aminohexanoyl)-pyrimidine nucleosides 5'-triphosphates that act as DNA polymerase substrates reversibly tagged at C-3'," JCS Perkin Trans, 1163-1171.

Sauer-Budge, A.F. et al. (2003) "Unzipping Kinetics of Double Stranded DNA in a Nanopore" Physical Review Letters 90(23):238101-1-238101-4.

Saxon, E. and Bertozzi, C.R. (2000) "Cell surface engineering by a modified Staudinger reaction," Science 287:2007-2010.

Schena, M., Shalon, D. and Davis, R. Brown P.O. (1995) "Quantitative monitoring of gene expression patterns with a cDNA microarray," Science 270: 467-470.

Seeger (1998) "Single Molecule Fluorescence: High-Performance Molecular Diagnosis and Screening," Bioforum, Git Verlag, Darmstadt, DE vol. 21, (German text).

Seo et al. (2003) "Click Chemistry to Construct Fluorescent Oligonucleotides for DNA Sequencing," J. Org. Chem. 68:609-612.

Seo et al. (2004) "Photocleavable Fluorescent Nucleotides for DNA Sequencing on a Chip Constructed by Site-Specific Coupling Chemistry," PNAS 101(15):5488-5493.

Seo et al. (2005) "Four-Color DNA Sequencing by Synthesis on a Chip Using Photocleavable Fluorescent Nucleotides," PNAS 102 (17):5926-5931.

Shendure, J.; Porreca, G. J.; Reppas, N.B.; et al. (2005) "Accurate Multiplex Polony Sequencing of an Evolved Bacterial Genome." Science 309:1728-1732.

Shim et al., Encapsulating a single G-quadruplex aptamer in a protein nanocavity. J Phys Chem B. Jul. 17, 2008; 112(28):8354-60. Epub Jun. 19, 2008.

Simon et al., Formation and stability of a suspended biomimetic lipid bilayer on silicon submicrometer-sized pores. J Colloid Interface Sci. Apr. 15, 2007; 308(2):337-43. Epub Jan. 31, 2007.

Singer et al. Nanopore Based Sequence Specific Detection of Duplex DNA for Genomic Profiling, Jan. 8, 2010, published Jan. 20, 2010, pp. 738-742.

Singh et al. (2001) "Synthesis of natural flutimide and analogous fully substituted pyrazine-2,6-diones, endonuclease inhibitors of influenza virus" J. Org. Chem. 66(16):5504-5516.

Smith, L.M., Sanders, J.Z., Kaiser, R.J., et al. (1986) "Fluorescence Detection in Automated DNA Sequence Analysis," Nature 321:674-679.

Smith, S.B. et al. (1996) "Overstretching B-DNA: the elastic response of individual double-stranded and single-stranded DNA molecules." Science 271:795-799.

Haff L.A. , et al. (1997) "Multiplex Genotyping of PCR Products with Mass Tag-Labeled Primers," Nucleic Acids Res. 25 (18) :3749-3750.

Hanshaw et al. (2004) "An Indicator Displacement System for Fluorescent Detection of Phosphate Oxyanions Under Physiological Conditions," Tetrahedron Letters, vol. 45, pp. 8721-8724.

Harlepp, et al. Probing complex RNA structures by mechanical force. Eur Phys J E Soft Matter. Dec. 2003; 12 (4) :605-15.

Harris et al. (2008) "Single-molecule DNA sequencing of a viral genome" Science, 320:106-109.

Hawkins et al. (2010) "Next-generation genomics: an integrative approach" Nat. Rev. Genet. 11:476-486.

Hayawaka et al. (1993) "O-Allyl Protection of Guanine and Thymine Residues in Oligodeoxyribonucleotides," J. Org. Chem., 58:5551-5555.

Heng, J.B. et al. (2005) "Stretching DNA Using the Electric Field in a Synthetic Nanopore" Nano Letters 5(9):1734-1737.

Heng, J.B. et al. (2006) "The Electromechanics of DNA in a synthetic nanopore" Biophysical Journal 90:1098-1106.

Henner, W.D. et al. (1983) "Enzyme Action at 3' Termini of Ionizing Radiation-Induced DNA Strand Breaks," J. Biol. Chem. 258 (24) :15198-15205.

Henrickson, S.E. et al (2000) "Driven DNA Transport into an Asymmetric Nanometer-scale Pore" Physical Review Letters 85:3057-3060.

Holden, et al. Direct introduction of single protein channels and pores into lipid bilayers. J Am Chem Soc. May 11, 2005; 127 (18) :6502-3.

Holden, et al. Direct transfer of membrane proteins from bacteria to planar bilayers for rapid screening by single-channel recording. Nat Chem Biol. Jun. 2006; 2(6):314-8. Epub May 7, 2006.

(56) References Cited

OTHER PUBLICATIONS

Hovinen et al. (1994) "Synthesis of 3'-O-(ω-Aminoalkoxymethyl) thymidine 5'-Triphosphates, Terminators of DNA Synthesis that Enable 3'-Labelling," J. Chem. Soc. Perkin Trans., 1:211-217.

Hromada, et al. Single molecule measurements within individual membrane-bound ion channels using a polymer-based bilayer lipid membrane chip. Lab Chip. Apr. 2008; 8(4):602-8. Epub Feb. 29, 2008.

Hsio, W.H., et al. "Surface-Enhanced Raman Scattering Imaging of a Single Molecule on Urchin-like Silver Nanowires." ACS Appl. Mater Interfaces 3, 3280-3284 (2011).

Hu et al. (1999) "Optical Mapping of DNA Polymerase I Action and Products," BBRC, 254:466-473.

Huang, B.G. et al. "Synthesis and in vitro Antitumor Activity of Some Amino-deoxy 3-hexofuranosylpyrrolo[2,3-d]pyrimidines." Carbohydrate Research, 1998, 308(3-4):319-328.

Huber et al. (1999) "Monitoring Solid Phase Synthesis by Infrared Spectroscopic Techniques." Analytica Chimica Acta, 393:213.

Hultman et al. (1989) "Direct Solid Phase Sequencing of Genomic and Plasmid DNA Using Magnetic Beads as Solid Support," Nucleic Acids Research 17 (3) :4937-4946.

Ikeda, K. et al. (1995) "A Non-Radioactive DNA Sequencing Method Using Biotinylated Dideoxynucleoside Triphosphates and Delta TTH DNA Polymerase," DNA Research 2(31):225-227.

Ireland, R.E. and Varney, M.D. (1986) "Approach to the total synthesis of chlorothricolide: synthesis of (±)-19.20-dihydro-24-O-methylchlorothricolide, methyl ester, ethyl carbonate," J. Org. Chem. 51:635-648.

Jacobsen, M.A. (2002) "Generation of 1-azapentadienyl anion from N-(tert-butyldimethylsilyl)-3-buten-1-amine." J. Org. Chem. 67(11):3915-8.

Jensen et al. (2010) "DMSO and Betaine Greatly Improve Amplification of GC-Rich Constructs in De Novo Synthesis", PLOS ONE vol. 5, No. 6.

Jiang-Baucom, P. et al. (1997) "DNA Typing of Human Leukocyte Antigen Sequence Polymorphisms by Peptide Nucleic Acid Probes and MALDI-TOF Mass Spectrometry," Anal. Chem. 69:4894-4896.

Ju, J., Ruan C., Fuller, C.W., Glazer, A.N., and Mathies R.A. (1995) "Fluorescence energy transfer dye-labeled primers for DNA sequencing and analysis," Proc. Natl. Acad. Sci. USA 92:4347-4351.

Ju, J. et al. (1996) "Cassette Labeling for Facile Construction of Energy Transfer Fluorescent Primers," Nuc. Acids Res. 24(6):1144-1148.

Ju, J., Glazer, A.N., and Mathies, R.A. (1996) "Energy Transfer Primers: A new Fluorescence Labeling Paradigm for DNA Sequencing and Analysis," Nature Medicine 2:246-249.

Ju, J. et al. (2006) "Four-color DNA Sequencing by Synthesis Using Cleavable Fluorescent Nucleotide Reversible Terminators," Proc. Natl. Acad. Sci. USA, 103(52):19635-40. Epub Dec. 14, 2006.

Jurinke, C., van de Boom, D., Collazo, V., Luchow, A., Jacob, A., and Koster H. (1997) "Recovery of nucleic acids from immobilized biotin-streptavidin complexes using ammonium hydroxide and application in MALDI-TOF mass spectrometry," Anal. Chem. 69:904-910.

Kamal, A., Laxman, E., and Rao, N.V. (1999) "A mild and rapid regeneration of alcohols from their allylic ethers by chlorotrimethylsilane/sodium iodide," Tetrahedron Lett 40:371-372.

Kan, C.W.; Doherty, E. A. S.; Barron, A. E. (2003) "A novel thermogelling matrix for microchannel DNA sequencing based on poly-N-alkoxyalkylacrylamide copolymers," Electrophoresis, 24, pp. 4161-4169.

Kang et al. A storable encapsulated bilayer chip containing a single protein nanopore. J Am Chem Soc. Apr. 18, 2007; 129(15):4701-5. Epub Mar. 22, 2007.

Kasianowicz J.J., Brandin, B., Branton, D. and Deamer, D.W. (1996) "Characterization of Individual Polynucleotide Molecules Using a Membrane Channel," Proc. Natl. Acad. Sci. USA 93:13770-13773.

Kasianowicz, J.J. (2003) "Nanonmeter-scale pores: potential applications for DNA characterization and analyte detection." Disease Markers 18:185-191.

Kasianowicz J.J. (2004) "Nanopore. Flossing with DNA" Nature Materials 3:355-356.

Kawano et al. Controlling the translocation of single-stranded DNA through alpha-hemolysin ion channels using viscosity. Langmuir. Jan. 20, 2009; 25(2):1233-7.

Sobin et al. (2002) "Solid Phase Capturable Dideoxynucleotides for Multiplex Genotyping Using Mass Spectrometry," Nucleic Acids Research 30(16):e85.1-e85-6.

Kim, S. et al. (2003) "Multiplex Genotyping of the Human Beta2-adrenergic Receptor Gene Using Solid-phase Capturable Dideoxynucleotides and Mass Spectrometry," Analytical Biochemistry 316:251-258.

Kimzey A.L. et al. (1998) "Specific Regions of Contact Between Human T-cell Leukemia Virus Type I Tax Protein and DNA Identified by Photocross-linking," Journal of Biological Chemistry, 273(22): 13768-13775.

Kitamura et al. (2002) "(P(C6H5)3)CpRu+Catalyzed Deprotection of Allyl Carboxylic Esters," J. Org. Chem., 67:4975-4977.

Kleinman, S.L. et al, Single-molecule Surface-Enhanced Raman Spectroscopy of Crystal Violet Isotopologues: Theory and Experiment, J. Am Chem Soc, 133, 4115-22 (2011).

Kloosterman et al. (1985) "The relative stability of allyl ether, allyloxycarbonyl ester and prop-2 enylidene acetal, protective groups toward Iridium, Rhodium and Palladium catalysts," Tetrahedron Letters, 26:5045-5048.

Kokoris, M. et al. (2000) "High-throughput SNP Genotyping With the Masscode System," Molecular Diagnosis 5(4):329-340.

Kolb et al. (2001) "Click Chemistry: Diverse Chemical Function From a Few Good Reactions," Angew. Chem. Int. Ed. 40:2004-2021.

Korlach, J. et al., "Processive Enzymatic DNA Synthesis Using 100% Dye-Labeled Terminal Phosphate-Linked Nucleotides," Nucleosides Nucleotides Nucleic Acids, 27, 1072-83 (2008).

Korlach, J. et al, "Real-Time DNA Sequencing from Single Polymerase Molecules," Methods Enzymol , 472, 431-55 (2010).

Kraevskii, A.A. et al. (1987) "Substrate Inhibitors of DNA Biosynthesis," Molecular Biology 21:25-29.

Krečmerová (1990) "Synthesis of 5'-O-Phosphonomethyl Derivatives of Pyrimidine 2'-Deoxynucleosides." Coll. Czech. Chem. Commun., 55:2521-2536.

Kumar, S. et al. "Terminal Phosphate Labeled Nucleotides: Synthesis, Applications, and Linker Effect on Incorporation by DNA Polymerases," Nucleosides Nucleotides Nucleic Acids, 24, 401-8 (2005).

Kumar et al. PEG-labeled nucleotides and nanopore detection for single molecule DNA sequencing by synthesis. Sci Rep. 2012; 2:684. Epub Sep. 21, 2012.

Kurata et al. (2001) "Fluorescent quenching-based quantitative detection of specific DNA/RNA using BODIPY® FL-labeled probe of primer," Nucleic Acids Research, vol. 29, No. 6, p. e34.

Kutik et al. Dissecting membrane insertion of mitochondrial beta-barrel proteins. Cell. Mar. 21, 2008; 132(6):1011-24.

Kvam et al., (1994) "Characterization of singlet oxygen-induced guanine residue damage after photochemical treatment of free nucleosides and DNA," Biochemica et Biophysica Acta., 1217:9-15.

Lee, L.G., et al. (1992) "DNA sequencing with dye labeled terminators and T7 DNA polymerase effect of dyes and dNTPs on incorporation of dye terminators and probability analysis of termination fragments," Nucleic Acids Res. 20:2471-2483.

Lee L.G. et al, (1997) "New energy transfer dyes for DNA sequencing," Nucleic Acids Res. 25:2816-2822.

Lee, S.E. et al. (2001) "Enhancing the catalytic repertoire of nucleic acids: a systematic study of linker length and rigidity." Nucleic Acids Research 29(7):1565-1573.

Leroy, E.M. et al. (2000) "Diagnosis of Ebola Haemorrhagic Fever by RT-PCR in an Epidemic Setting," Journal of Medical Virology 60:463-467.

(56) References Cited

OTHER PUBLICATIONS

Lewis et al. (2002) "Click Chemistry in Situ: Acetylcholinesterase as a Reaction Vessel for the Selective Assembly of a Femtomolar Inhibitor from an Array of Building Blocks," Angew. Chem. Int. Ed. 41(6):1053-1057.
Li, J. (1999) "Single Oligonucleotide Polymorphism Determination Using Primer Extension and Time-of-Flight Mass Spectrometry," Electrophoresis 20:1258-1265.
Li. L. et al. (2001) "Ion-beam sculpting at nanometre length scales" Nature 412:166-169.
Li, W.D. et al., "Three-Dimensional Cavity Nanoantenna Coupled Plasmonic Nanodots for Ultrahigh and Uniform Surface-Enhanced Raman Scattering Over Large Area," Opt. Express 19, 3925-36 (2011).
Li, Z. et al. (2003) "A photocleavable Fluorescent Nucleotide for DNA Sequencing and Analysis," PNAS 100(2):414-419.
Lieberman et al. "Processive Replication of Single DNA Molecules in a Nanopore Catalyzed by phi29 DNA Polymerase", Jol. ACS, vol. 132, No. 50, Dec. 22, 2010, pp. 17961-17972.
Liu, H. et al. (2000) "Development of Multichannel Devices with an Array of Electrospray Tips for High-Throughput Mass Spectrometry," Anal. Chem. 72:3303-3310.
Loubinoux, B. et al. "Protection Des Phenols Par Le Groupement Azidomethylene Application A La Synthese De Phenols Instables," Tetrahedron, 1998, 44(19): 6055 (English Abstract Only).
Lu, G. and Burgess, K. (2006) "A Diversity Oriented Synthesis of 3'-O-Modified Nucleoside Triphosphates for DNA 'Sequencing by Synthesis'" Bioorg. Med. Chem. Lett., 16:3902-3905.
Lundquist, J.T. et al (2002) "A New Tri-Orthogonal Strategy for Peptide Cyclization" Org. Lett. 4(19):3219-3221.
Lyamichev, V. et al. (1999) "Polymorphism Identification and Quantitative Detection of Genomic DNA by Invasive Cleavage of Oligonucleotide Probes," Nat. Biotech 17:292-296.
Madampage, et al. Nanopore detection of antibody prion interactions. Anal Biochem. Jan. 1, 2010; 396(1):36-41. Epub Aug. 21, 2009.
Maier et al. (1995) "Synthesis and Properties of New Fluorescein-Labeled Oligonucleotides," Nucleosides and Nucleotides, 14:961-965.
Soli, E.D. et al (1999) Azide and Cyanide Displacements via Hypervalent Silicate Intermediates. J. Org. Chem. 64(9):3171-3177.
Sood, A., "Terminal Phosphate-Labeled Nucleotides With Improved Substrate Properties for Homogenous Nucleic Acid Assays," J Am Chem Soc 127, 2394-5 (2005).
Speicher, M.R., Ballard, S.G., and Ward, D.C. (1996) "Karyotyping human chromosomes by combinatorial multi-fluor FISH," Nature Genetics 12: 368-375.
Sterfureac et al. Transport of alpha-helical peptides through alpha-hemolysin and aerolysin pores. Biochemistry. Aug. 1, 2006; 45(30):9172-9.
Stefureac et al. Nanopore analysis of the interaction of metal ions with prion proteins and peptides. Biochem Cell Biol. Apr. 2010; 88(2):347-58.
Stoddart et al. Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Stoddart et al. Nucleobase recognition in ssDNA at the central constriction of the alpha-hemolysin pore. Nano Lett. Sep. 8, 2010; 10(9):3633-7.
Stoerker, J. et al. (2000) "Rapid Genotyping by MALDI-monitored nuclease selection from probe Libraries," Nat. Biotech 18:1213-1216.
Streater M et al., (Novel 3-hydroxy-2 (IH)-pyridinones. Synthesis, iron (III)-chelating properties, and biological activity. J. Medicinal Chem. (1990) 33(6):1749-1755.
Studer et al., Formation of individual protein channels in lipid bilayers suspended in nanopores. Colloids Surf B Biointerfaces., Oct. 15, 2009; 73(2):325-31. Epub Jun. 10, 2009.
Suzuki et el., Highly reproducible method of planar lipid bilayer reconstitution in polymethyl methacrylate microfluidic chip. , Feb. 2006, Langmuir. 22(4):1937-42.
Tang, K., Fu, D.J., Julien, D., Braun, A., Cantor, C.R., and Koster, H. (1999) "Chip-based genotyping by mass spectrometry," Proc. Natl. Acad. Sci. USA. 96:10016-10020.
Thomson et al., Preliminary nanopore cheminformatics analysis of aptamer-target binding strength, Nov. 2007, BMC Bioinformatics. 1; 8 Suppl 7:S11.
Tong, X. and Smith, L.M. (1992) "Solid-Phase Method for the Purification of DNA Sequencing Reactions," Anal. Chem. 64:2672-2677.
Torimura et al. (2001) "Fluorescence-Quenching Phenomenon by Photoinduced Electron Transfer between a Fluorescent Dye and Nucleotide Base," Analytical Sciences, 17:155-160.
Tuncel et al. (1999) "Catalytically Self-Threading Polyrotaxanes," Chem. Comm. 1509-1510.
Turcatti et al. (2008) "A new class of cleavable fluorescent nucleotides: synthesis and optimization as reversible terminators for DNA sequencing by synthesis" Nucleic Acids Res., 36:e25.
Varley, K.E. et al., "Bisufite Patch PCR Enables Multiplexed Sequencing of Promoter Methylation Across Cancer Samples," Genome Res. 20, 1279-87 (2010).
Veeneman et al. (1991) "An Efficient Approach to the Synthesis of Thymidine Derivatives Containing Phosphate-Isoteric Methylene Acetyl Linkages," Tetrahedron, 47:1547-1562.
Vercoutere W. et al., "Rapid discrimination among individual DNA hairpin molecules at single-nucleotide resolution using an ion channel.", 2001, Nat. Biotech 19:248-252.
Vercoutere W. et al. (2003), "Discrimination among individual Watson-Crick base pairs at the termini of single DNA hairpin molecules", Nucleic Acid Res., vol. 31, No. 4, 1311-1319; DOI: 10.1093/nar/gkg218.
Viasnoff et al., Probing DNA base pairing energy profiles using a nanopore. Eur Biophys J., Feb. 2009, 38(2):263-9. Epub Oct. 3, 2008.
Wada et al. (2001) "2-(Azidomethyl)benzoyl as a new protecting group in nucleosides," Tetrahedron Letters, 42:1069-1072.
Wang H. et al., (2004) "DNA heterogeneity and Phosphorylation unveiled by Single-Molecule Electrophoresis" Proc. Natl. Acad. Sci. USA 101(37):13472-13477.
Wanunu et al., DNA profiling using solid-state nanopores: detection of DNA-binding molecules. Nano Lett. Oct. 2009; 9(10):3498-502.
Wei et al.,"Stochastic sensing of proteins with receptor-modified solid-state nanopores" Nature Nanotechnology, 7(4):257-263 (2012).
Weiss (1999) "Fluorescent Spectroscopy of Single Biomolecules." Science, 283:1676.
Welch et al. (1999) "Synthesis of Nucleosides Designed for Combinatorial DNA Sequencing," Chemistry, European Journal, 5:951-960.
Wendy, Jen, et al. (2000) "New Strategies for Organic Catalysis: The First Enantioselective Orgacnocatalytic 1,3-Dipolar Cycloaddition," J. Am. Chem. Soc. 122:9874-9875.
Weng et al., Fluid biomembranes supported on nanoporous aerogel/xerogel substrates. Langmuir. Aug. 17, 2004; 20(17):7232-9.
Wilson et al., Feedback control of a DNA molecule tethered in a nanopore to repeatedly probe DNA-binding enzymes. Conf Proc IEEE Eng Med Biol Soc. 2008; 2008:5745-8.
Wilson et al., Electronic control of DNA polymerase binding and unbinding to single DNA molecules. ACS Nano. Apr. 28, 2009; 3(4):995-1003.
Winters-Hilt et al., Nanopore-based kinetics analysis of individual antibody-channel and antibody-antigen interactions. BMC Bioinformatics. Nov. 1, 2007; 8 Suppl 7:S20.
Woodside et al., Nanomechanical measurements of the sequence-dependent folding landscapes of single nucleic acid hairpins. Proc Natl Acad Sci U S A. Apr. 18, 2006; 103(16):6190-5. Epub Apr. 10, 2006.
Woodside et al., Direct measurement of the full, sequence-dependent folding landscape of a nucleic acid. Science. Nov. 10, 2006; 314(5801):1001-4.
Woolley, A. T. et al. (1997) "High-Speed DNA Genotyping Using Microfabricated Capillary Array Electrophoresis Chips," Anal. Chem. 69:2181-2186.

(56) References Cited

OTHER PUBLICATIONS

Wu et al. (2007) 3'-O-modified Nucleotides as Reversible Terminators for Pyrosequencing. Proc Natl Acad Sci USA. 104:16462-16467.
Wu et al. (2007) "Termination of DNA synthesis by N6-alkylated, not 3'-O-alkylated, photocleavable 2'-deoxyadenosine triphosphates" Nucleic Acids Res. 35:6339-49.
Wu et al., Single-molecule detection of nitrogen mustards by covalent reaction within a protein nanopore. J Am Chem Soc. May 28, 2008; 130(21):6813-9. Epub Apr. 30, 2008.
Yamashita et al. (1987) "Studies on Antitumor Agents VII. Antitumor Activities of O-Alkoxyalkyl Derivatives of 2'-Deoxy-5-trifluoromethyluridine." Chem Pharm. Bull., vol. 35, pp. 2373-2381.
Zavgorodny, S. et al. (1991) "1-Alkylthioalkylation of Nucleoside Hydroxyl Functions and Its Synthetic Applications: A New Versatile Method in Nucleoside Chemistry," Tetrahedron Letters, 32(51): 7593-7596.
Zavgorodny et al. (2000) "S,X-Acetals in Nucleoside Chemistry. III. Synthesis of 2'- and 3'-O-Azidomethyl Derivatives of Ribonucleosides" Nucleosides, Nucleotides and Nucleic Acids, 19(10-12):1977-1991.
Zeineldin et al., Using bicellar mixtures to form supported and suspended lipid bilayers on silicon chips. Langmuir. Sep. 12, 2006; 22 (19) :8163-8.
Zhang et al. (2002) "Synthesis of Releasable Electrophore Tags for Applications in Mass Spectrometry," Bioconjugate Chem., vol. 13, pp. 1002-1012.
Zhu, Z., Chao, J., Yu, H, et al. (1994) "Directly Labeled DNA Probes Using Fluorescent Nucleotides with Different Length Linkers," Nucleic Acids Res., 22:3418-3422.
Zwolak, et al. Electronic signature of DNA nucleotides via transverse transport. Nano Lett. Mar. 2005; 5 (3) :421-4.
Office Action dated Feb. 12, 2010 in connection with U.S. Appl. No. 12/084,457.
Jun. 10, 2010 Response to Office Action dated Feb. 12, 2010 in connection with U.S. Appl. No. 12/084,457.
Office Action dated Aug. 2, 2010 in connection with U.S. Appl. No. 12/084,457.
Feb. 2, 2011 Amendment in response to Office Action dated Aug. 2, 2010 in connection with U.S. Appl. No. 12/084,457.
Final Office Action dated May 2, 2011 in connection with U.S. Appl. No. 12/084,457.
Nov. 2, 2011 Amendment in response to Final Office Action dated May 2, 2011 in connection with U.S. Appl. No. 12/084,457.
Ex Parte Quayle Action issued Feb. 12, 2013 in connection with U.S. Appl. No. 12/084,457.
Aug. 9, 2013 Response after Ex Parte Quayle Action issued Feb. 12, 2013 in connection with U.S. Appl. No. 12/084,457.
Notice of Allowance dated Aug. 29, 2013 in connection with U.S. Appl. No. 12/084,457.
Notice of Allowance dated Jan. 28, 2014 in connection with U.S. Appl. No. 12/084,457.
Office Action dated Oct. 21, 2014 in connection with U.S. Appl. No. 14/451,265.
Mar. 20, 2015 Amendment in response to Office Action dated Oct. 21, 2014 in connection with U.S. Appl. No. 14/451,265.
Final Office Action dated May 28, 2015 in connection with U.S. Appl. No. 14/451,265.
Response to Final Office Action, filed Oct. 26, 2015 in connection with U.S. Appl. No. 14/451,265.
Notice of Allowance, dated Nov. 18, 2015 in connection with U.S. Appl. No. 14/451,265.
Notification of Transmittal of International Search Report and Written Opinion, dated Feb. 6, 2008 in connection with International Application No. PCT/US06/42739.
International Search Report dated Feb. 6, 2008 in connection with International Application No. PCT/US06/42739.
Notification Concerning Transmittal of International Preliminary Report on Patentability dated Mar. 26, 2009 in connection with International Application No. PCT/US06/42739.
Examination Report Under Section 18(3) dated Jan. 28, 2010 in connection with United Kingdom Patent Application No. GB0808033.5.
Jul. 27, 2010 Response to Examination Report Under Section 18(3) dated Jan. 28, 2010 in connection with United Kingdom Patent Application No. GB0808033.5.
Examination Report Under Section 18(3) dated Oct. 4, 2010 in connection with United Kingdom Patent Application No. GB0808033.5.
Jan. 4, 2011 Response to Examination Report Under Section 18(3) dated Oct. 4, 2010 in connection with United Kingdom Patent Application No. GB0808033.5.
Examination Report Under Section 18(3) dated Jan. 7, 2011 in connection with United Kingdom Patent Application No. GB0808033.5.
Jan. 17, 2011 Response to Examination Report Under Section 18(3) dated Jan. 7, 2011 in connection with United Kingdom Patent Application No. GB0808033.5.
Office Action dated Oct. 14, 2010 in connection with U.S. Appl. No. 12/084,338.
Feb. 14, 2011 Amendment in response to Office Action dated Oct. 14, 2010 in connection with U.S. Appl. No. 12/084,338.
Notice of Allowance dated Mar. 1, 2011 in connection with U.S. Appl. No. 12/084,338.
Issue Notification dated Jun. 29, 2011 in connection with U.S. Appl. No. 12/084,338.
Office Action dated May 7, 2012 in connection with U.S. Appl. No. 13/186,353.
Nov. 7, 2012 Amendment in response to Office Action dated May 7, 2012 in connection with U.S. Appl. No. 13/186,353.
Final Office Action dated Jan. 11, 2013 in connection with U.S. Appl. No. 13/186,353.
Feb. 11, 2014 Amendment in response to Final Office Action dated Jan. 11, 2013 in connection with U.S. Appl. No. 13/186,353.
Office Action dated Mar. 5, 2014 in connection with U.S. Appl. No. 13/186,353.
Sep. 5, 2014 Response to Office Action dated Mar. 5, 2014 in connection with U.S. Appl. No. 13/186,353.
Sep. 24, 2014 Supplemental Amendment in connection with U.S. Appl. No. 13/186,353.
Office Action dated Nov. 14, 2014 in connection with U.S. Appl. No. 13/186,353.
Feb. 25, 2015 Response to Office Action dated Nov. 14, 2014 in connection with U.S. Appl. No. 13/186,353.
Office Action dated Apr. 27, 2015 in connection with U.S. Appl. No. 13/186,353.
Response to Final Office Action, filed Jul. 27, 2015 in connection with U.S. Appl. No. 13/186,353.
Notice of Allowance, dated Sep. 23, 2015 in connection with U.S. Appl. No. 13/186,353.
Notice to File Corrected Application Papers, dated Feb. 8, 2016 in connection with U.S. Appl. No. 14/992,784.
Response to Notice to File Corrected Application Papers issued in connection with U.S. Appl. No. 14/992,784.
Notification of Transmittal of International Search Report and Written Opinion, dated Nov. 23, 2007 in connection with International Application No. PCT/US06/42698.
Notification Concerning Transmittal of International Preliminary Report on Patentability (Including Written Opinion of the International Searching Authority) dated May 15, 2008 in connection with PCT/US2006/042698.
Examination Report Under Section 18(3) dated Jan. 28, 2010 in connection with United Kingdom Patent Application No. GB0808034.3.
Jul. 27, 2010 Response to Examination Report Under Section 18(3) dated Jan. 28, 2010 in connection with United Kingdom Patent Application No. GB0808034.3.
Examination Report Under Section 18(3) dated Oct. 4, 2010 in connection with United Kingdom Patent Application No. GB0808034.3.

(56) References Cited

OTHER PUBLICATIONS

Jan. 4, 2011 Response to Examination Report Under Section 18(3) dated Oct. 4, 2010 in connection with United Kingdom Patent Application No. GB0808034.3.
Examination Report Under Section 18(3) dated Jan. 7, 2011 in connection with United Kingdom Patent Application No. GB0808034.3.
Jan. 17, 2011 Response to Examination Report Under Section 18(3) dated Jan. 7, 2011 in connection with United Kingdom Patent Application No. GB0808034.3.
Jun. 23, 2011 Restriction Requirement issued in connection with U.S. Appl. No. 12/308,091.
Oct. 24, 2011 Response to Restriction Requirement dated Jun. 23, 2011 in connection with U.S. Appl. No. 12/308,091.
Office Action dated Nov. 29, 2011 in connection with U.S. Appl. No. 12/308,091.
Apr. 30, 2012 Amendment in Response to Office Action dated Nov. 29, 2011 in connection with U.S. Appl. No. 12/308,091.
Office Action dated Jun. 28, 2012 in connection with U.S. Appl. No. 12/308,091.
Dec. 28, 2012 Amendment in response to Office Action dated Jun. 28, 2012 in connection with U.S. Appl. No. 12/308,091.
Jul. 17, 2014 Notice of Allowance issued in connection with U.S. Appl. No. 12/308,091.
Mar. 4, 2016 Office Action in connection with U.S. Appl. No. 14/516,785, Ju et al.
International Search Report and Written Opinion of the International Searching Authority issued by the International Searching Authority (ISA/US) dated Oct. 29, 2007 in connection with International Application No. PCT/US2007/013559.
International Preliminary Report on Patentability, dated Dec. 10, 2008 in connection with International Application No. PCT/US07/13559.
Jun. 22, 2011 Office Action in connection with Chinese Patent Application No. 200780028545.1 (with English translation of cover page only).
Jan. 6, 2012 Response to First Office Action filed in connection with Chinese Patent Application No. 200780028545.1 (with English translation).
Jul. 2, 2012 Second Office Action in connection with Chinese Patent Application No. 200780028545.1 (with English translation) [76315-A-PCT-China].
Nov. 19, 2012 Response to Second Office Action filed in connection with Chinese Patent Application No. 200780028545.1 (with English translation).
Apr. 9, 2013 Third Office Action in connection with Chinese Patent Application No. 200780028545.1 (with English translation).
Jun. 21, 2013 Response to Third Office Action filed in connection with Chinese Patent Application No. 200780028545.1 (with English translation).
Oct. 12, 2013 Decision of Rejection issued in connection with Chinese Patent Application No. 200780028545.1 (with English translation).
Jan. 26, 2014 Request for Reexamination filed in connection with Chinese Patent Application No. 200780028545.1 (with English.
Mar. 24, 2015 Office Action issued in connection with Chinese Patent Application No. 200780028545.1.
Sep. 8, 2015 Response to Mar. 24, 2015 Office Action issued in connection with Chinese Patent Application No. 200780028545.1.
Nov. 13, 2015 Decision on Reexamination issued in conection with Chinese Patent Application No. 200780028545.1.
Feb. 3, 2016 Office Action issued in connection with Chinese Patent Application No. 200780028545.1.
Apr. 18, 2016 Response to Feb. 3, 2016 Office Action issued in connection with Chinese Patent Application No. 200780028545.1.
Jun. 29, 2016 Office Action issued in connection with Chinese Patent Application No. 200780028545.1.

\* cited by examiner n = 16, 20, 24 and 36

Coumarin-(PEG)$_n$-dG4P

R= $N_3$, CN, C≡CH, C≡C-R'
X= Reactive group to react with -SH or -$NH_2$ group in protein
n= 1-20

(A)

(B)

(A)

(B)

RAMAN CLUSTER TAGGED MOLECULES FOR BIOLOGICAL IMAGING

CROSS-REFERENCE TO RELATED APPLICATIONS

This application is a § 371 national stage of PCT International Application No. PCT/US2014/029477, filed Mar. 14, 2014, claiming the benefit of U.S. Provisional Application No. 61/799,082, filed Mar. 15, 2013, the contents of each of which are hereby incorporated by reference in their entirety.

Throughout this application, certain publications are referenced, the latter by authors and publication year. Full citations for these publications may be found immediately preceding the claims. The disclosures of these publications in their entireties are hereby incorporated by reference into this application in order to describe more fully the state of the art to which this invention relates.

BACKGROUND OF THE INVENTION

High throughput DNA sequencing is essential to a broad array of genomic studies, such as whole genome and metagenome sequencing, expression profiling of mRNAs and miRNAs, discovery of alternatively spliced and polyadenylated transcripts, histone and chromatin changes involved in epigenetic events, and identification of binding sites for transcription factors and RNA binding proteins. Sequencing of individual human genomes is especially appealing, with its potentially unlimited but as yet unachieved promise for personalized medicine.

Given the ever-growing importance of high throughput DNA sequencing for biological and anthropological research, agriculture and medicine, there is a need for sequencing technologies that are low-cost and rapid on the one hand, and have high sensitivity and accuracy on the other. Sequencing by Synthesis (SBS) has driven much of the "next generation" sequencing technology, allowing the field to approach the $100,000 Genome [Fuller et al. 2009, Hawkins et al. 2010, Morozova at al. 2009, and Park 2009]. With further improvements in nucleotide incorporation detection methods, SBS could be an engine that drives third-generation platforms leading to the reality of the "$1,000 Genome". At the same time, since non-fluorescent detection approaches are likely to decrease the cost of obtaining data by avoiding expensive cameras and imaging tools, SBS also offers the possibility of high sensitivity, leading to both longer reads and permitting single molecule sequencing, thereby removing one of the most time-consuming and biased steps—the generation and amplification of DNA templates.

Current commercial next-generation sequencing platforms have certainly made substantial inroads in this direction, with the current cost of sequencing a human genome at high draft coverage significantly below $10,000 [Fuller at al. 2009, Hawkins et al. 2010, Morozova et al. 2009, and Metzker 2010]. Expression studies (e.g. using RNA-Seq) and epigenetic studies (e.g. using Methyl-Seq, ChIP-Seq), among many others, have also benefited greatly from these platforms [Ozsolak et al. 2011, Varley et al. 2010, and Park 2009]. Nonetheless, these costs are still prohibitive for most laboratories and for clinical applications.

All of the current approaches have one or more additional limitations: biased coverage of GC-rich or AT-rich portions of genomes; inability to accurately sequence through homopolymer stretches; inability to directly sequence RNA; high reagent costs; difficulty in sequencing beyond 200 or so nucleotides resulting in difficulty in de novo assembly of previously unsequenced genomes; insufficient throughput due to ceiling on number of possible reads per run.

To overcome these obstacles, a number of third-generation sequencing platforms have appeared on the market, or are in development. All of these have issues with accuracy and most have limited throughput. For example, attempts to sequence DNA using Raman detection have been reported [Kneipp et al. 1998] but thus far have been unsuccessful.

In addition to high throughput DNA sequencing, detection of protein-protein interactions are essential for study of cell biology. Examples of protein-protein interactions include generation of protein assemblies for enzymatic reactions in metabolic pathways (e.g., fatty acid synthesis), ribosomes (protein synthesis), ubiquitin association with proteins destined to be degraded, for transport of ions (multi-subunit membrane channels and pumps), for enhancing or inhibiting transcription of genes (cooperating transcription factors), formation of cellular junctions and cell-cell interactions, and countless other examples. Mutations in these proteins affecting their assembly or interactions are crucial for a number of diseases, and particularly relevant to the development of tumors.

Numerous assays have been developed for detection of specific protein-protein interactions. Biochemical approaches include gel shift assays, cross-linking assays, immunoprecipitation, immunoblotting, etc. The yeast two-hybrid and three-hybrid systems are genetic approaches that have been developed to identify target proteins that can bind to a bait protein molecule. Several of these methods characterize the partners and the complexes by gel electrophoresis with at least one of the partners radiolabeled. Other assays including surface binding assays, for example protein arrays, may use fluorescent tags. Finally, it is possible to reveal the interacting proteins by mass spectrometry.

Recently, use of Raman spectroscopy for molecular detection has been considered. When combined with modified surfaces decorated with colloidal gold or other metals, that coat structures such as pillars or antennae, taking advantage of surface plasmonics, one can obtain extraordinarily enhanced Raman signals (as much as 15 orders of magnitude). However, despite its impressive potential for signal enhancement, a major problem with surface-enhanced Raman spectroscopy (SERS) is consistency, which is related in part to the disposition of the Raman scattering group relative to the gold particles or nanocrystals. Thus it is clear that transformative methods are needed.

SUMMARY OF THE INVENTION

This invention provides a nucleoside polyphosphate analog having the structure:

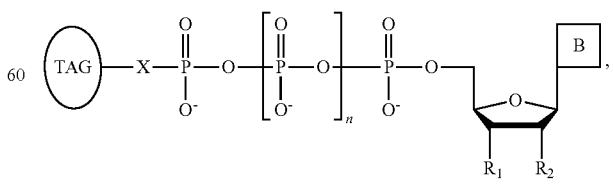

wherein B is a base and is adenine, guanine, cytosine, uracil, thymine, or a derivative thereof, wherein $R_1$ is OH, wherein $R_2$ is OH or H, wherein n is 1, 2, 3, or 4, wherein X is a linker, and wherein tag comprises a plurality of Raman-scattering moieties.

This invention also provides a composition comprising four deoxyribonucleoside polyphosphate (dNPP) analogs, each dNPP analog having the structure:

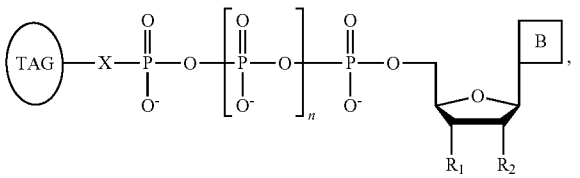

wherein B is a base and is adenine, guanine, cytosine, thymine, or a derivative thereof, wherein $R_1$ is OH, wherein $R_2$ is OH or H, wherein n is 1, 2, 3, or 4, wherein X is a linker, wherein tag comprises a plurality of Raman-scattering moieties, wherein (i) the Raman spectroscopy peak of the tag on each dNPP analog is distinguishable from the Raman spectroscopy peak of the tag on each of the remaining three dNPP analogs, and (ii) each dNPP analog comprises a base which is different from the base of each of the remaining three dNPP analogs.

This invention also provides a composition comprising four ribonucleoside polyphosphate (rNPP) analogs, each rNPP analog having the structure:

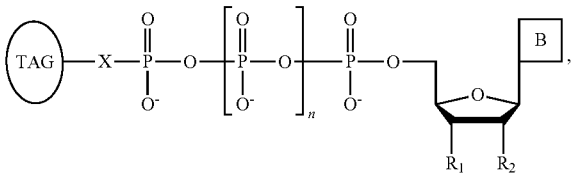

wherein B is a base and is adenine, guanine, cytosine, uracil, or a derivative thereof, wherein $R_1$ is OH, wherein $R_2$ is OH, wherein n is 1, 2, 3, or 4, wherein X is a linker, wherein tag comprises a plurality of Raman-scattering moieties, wherein (i) the Raman spectroscopy peak of the tag on each rNPP analog is distinguishable from the Raman spectroscopy peak of the tag on each of the remaining three rNPP analogs, and (ii) each rNPP analog comprises a base which is different from the base of each of the remaining three rNPP analogs.

This invention also provides a method for determining the sequence of a single-stranded DNA comprising:
(a) contacting the single-stranded DNA having a primer hybridized to a portion thereof with a DNA polymerase and four deoxyribonucleoside polyphosphate (dNPP) analogs under conditions permitting the DNA polymerase to catalyze incorporation onto the primer of a dNPP analog complementary to a nucleotide residue of the single-stranded DNA which is immediately 5' to a nucleotide residue of the single-stranded DNA hybridized to the 3' terminal nucleotide residue of the primer, so as to form a DNA extension product, wherein each dNPP analog has the structure:

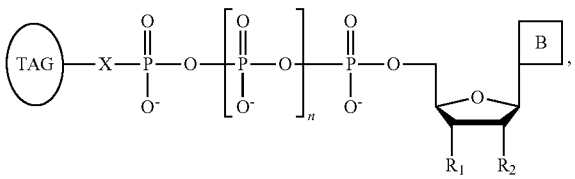

wherein B is a base and is adenine, guanine, cytosine, thymine, or a derivative thereof, wherein $R_1$ is OH, wherein $R_2$ is OH or H, wherein n is 1, 2, 3, or 4, wherein X is a linker, wherein tag comprises a plurality of Raman-scattering moieties,
wherein (i) the Raman spectroscopy peak of the tag on each dNPP analog is distinguishable from the Raman spectroscopy peak of the tag on each of the remaining three dNPP analogs, and (ii) each dNPP analog comprises a base which is different from the base of each of the remaining three dNPP analogs, and wherein the incorporation of the dNPP analog releases a tagged polyphosphate;
(b) determining the wavenumber of the Raman spectroscopy peak of the tagged polyphosphate released in step (a), so as to thereby determining the identity of the incorporated dNPP analog and the identity of the complementary nucleotide residue in the single-stranded DNA; and
(c) iteratively performing steps (a) and (b) for each nucleotide residue of the single-stranded DNA to be sequenced so as to thereby determining the sequence of the single-stranded DNA.

This invention further provides a method for determining the sequence of a single-stranded RNA comprising:
(a) contacting the single-stranded RNA having a primer hybridized to a portion thereof with an RNA polymerase and four ribonucleoside polyphosphate (rNPP) analogs under conditions permitting the RNA polymerase to catalyze incorporation onto the primer of an rNPP analog complementary to a nucleotide residue of the single-stranded RNA which is immediately 5' to a nucleotide residue of the single-stranded RNA hybridized to the 3' terminal nucleotide residue of the primer, so as to form an RNA extension product, wherein each rNPP analog has the structure:

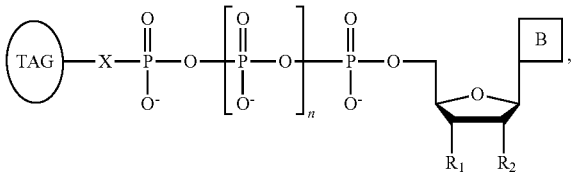

wherein H is a base and is adenine, guanine, cytosine, uracil, or a derivative thereof, wherein $R_1$ is OH, wherein $R_2$ is OH, wherein n is 1, 2, 3, or 4, wherein X is a linker, wherein tag comprises a plurality of Raman-scattering moieties,
wherein (i) the Raman spectroscopy peak of the tag on each rNPP analog is distinguishable from the Raman spectroscopy peak of the tag on each of the remaining three rNPP analogs, and (ii) each rNPP analog comprises a base which is different from the base of each of the remaining three rNPP analogs, and
wherein the incorporation of the rNPP analog releases a tagged polyphosphate;

(b) determining the wavenumber of the Raman spectroscopy peak of the tagged polyphosphate released in step (a), so as to thereby determining the identity of the incorporated rNPP analog and the identity of the complementary nucleotide residue in the single-stranded RNA; and (c) iteratively performing steps (a) and (b) for each nucleotide residue of the single-stranded RNA to be sequenced so as to thereby determining the sequence of the single-stranded RNA.

This invention even further provides a method for detecting interaction of a plurality of predetermined compounds comprising:

(a) contacting at least a first predetermined compound immobilized on a solid surface with a solution containing at least a second predetermined compound, wherein the second predetermined compound having attached thereto a tag comprises a plurality of Raman-scattering moieties, under conditions permitting binding of said at least first and second predetermined compounds such that only said second predetermined compound bound to said immobilized first predetermined compound is within the detection range of a detector; and (b) performing Raman spectroscopy, wherein detection of a Raman spectroscopy peak indicating presence of the tag and binding of said at least first and second predetermined compounds, so as to thereby detecting the interaction of the plurality of predetermined compounds.

DETAILED DESCRIPTION OF THE INVENTION

Figure 1:
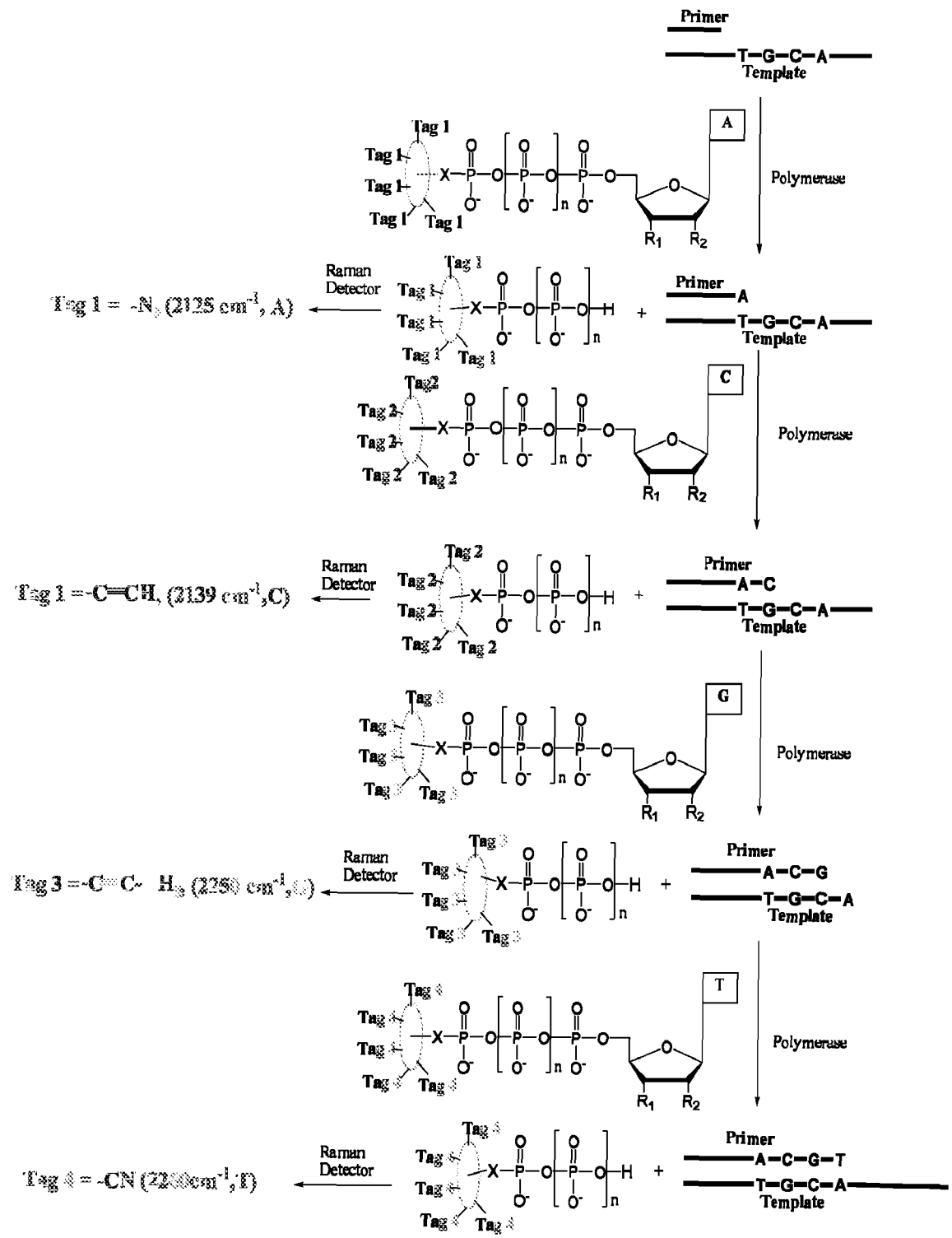
FIG. 1. Scheme for continuous nucleotide incorporation and testing by Raman microscopy.

This invention provides a nucleoside polyphosphate analog having the structure:

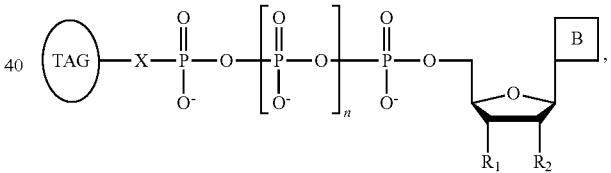

wherein B is a base and is adenine, guanine, cytosine, uracil, thymine, or a derivative thereof, wherein $R_1$ is OH, wherein $R_2$ is OH or H, wherein n is 1, 2, 3, or 4, wherein X is a linker, and wherein tag comprises a plurality of Raman-scattering moieties.

This invention also provides a composition comprising four deoxyribonucleoside polyphosphate (dNPP) analogs, each dNPP analog having the structure:

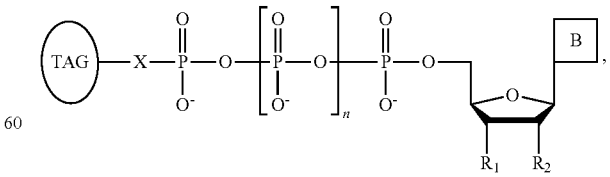

wherein B is a base and is adenine, guanine, cytosine, thymine, or a derivative thereof, wherein $R_1$ is OH, wherein $R_2$ is OH or H, wherein n is 1, 2, 3, or 4, wherein X is a linker, wherein tag comprises a plurality of Raman-scattering moieties, wherein (i) the Raman spectroscopy peak of the tag on each dNPP analog is distinguishable from the Raman spectroscopy peak of the tag on each of the remaining three dNPP analogs, and (ii) each dNPP analog comprises a base which is different from the base of each of the remaining three dNPP analogs.

This invention also provides a composition comprising four ribonucleoside polyphosphate (rNPP) analogs, each rNPP analog having the structure:

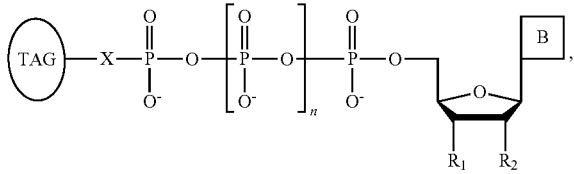

wherein B is a base and is adenine, guanine, cytosine, uracil, or a derivative thereof, wherein $R_1$ is OH, wherein $R_2$ is OH, wherein n is 1, 2, 3, or 4, wherein X is a linker, wherein tag comprises a plurality of Raman-scattering moieties, wherein (i) the Raman spectroscopy peak of the tag on each rNPP analog is distinguishable from the Raman spectroscopy peak of the tag on each of the remaining three rNPP analogs, and (ii) each rNPP analog comprises a base which is different from the base of each of the remaining three rNPP analogs.

This invention also provides a method for determining the sequence of a single-stranded DNA comprising:
(a) contacting the single-stranded DNA having a primer hybridized to a portion thereof with a DNA polymerase and four deoxyribonucleoside polyphosphate (dNPP) analogs under conditions permitting the DNA polymerase to catalyze incorporation onto the primer of a dNPP analog complementary to a nucleotide residue of the single-stranded DNA which is immediately 5' to a nucleotide residue of the single-stranded DNA hybridized to the 3' terminal nucleotide residue of the primer, so as to form a DNA extension product, wherein each dNPP analog has the structure:

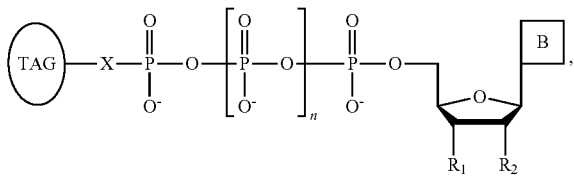

wherein B is a base and is adenine, guanine, cytosine, thymine, or a derivative thereof, wherein $R_1$ is OH, wherein $R_2$ is OH or H, wherein n is 1, 2, 3, or 4, wherein X is a linker, wherein tag comprises a plurality of Raman-scattering moieties,
wherein (i) the Raman spectroscopy peak of the tag on each dNPP analog is distinguishable from the Raman spectroscopy peak of the tag on each of the remaining three dNPP analogs, and (ii) each dNPP analog comprises a base which is different from the base of each of the remaining three dNPP analogs, and
wherein the incorporation of the dNPP analog releases a tagged polyphosphate;
(b) determining the wavenumber of the Raman spectroscopy peak of the tagged polyphosphate released in step (a), so as to thereby determining the identity of the incorporated dNPP analog and the identity of the complementary nucleotide residue in the single-stranded DNA; and
(c) iteratively performing steps (a) and (b) for each nucleotide residue of the single-stranded DNA to be sequenced so as to thereby determining the sequence of the single-stranded DNA.

This invention further provides a method for determining the sequence of a single-stranded RNA comprising:
(a) contacting the single-stranded RNA having a primer hybridized to a portion thereof with an RNA polymerase and four ribonucleoside polyphosphate (rNPP) analogs under conditions permitting the RNA polymerase to catalyze incorporation onto the primer of an rNPP analog complementary to a nucleotide residue of the single-stranded RNA which is immediately 5' to a nucleotide residue of the single-stranded RNA hybridized to the 3' terminal nucleotide residue of the primer, so as to form an RNA extension product, wherein each rNPP analog has the structure:

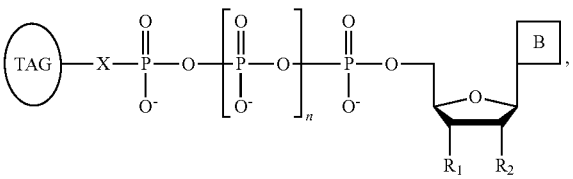

wherein B is a base and is adenine, guanine, cytosine, uracil, or a derivative thereof, wherein $R_1$ is OH, wherein $R_2$ is OH, wherein n is 1, 2, 3, or 4, wherein X is a linker, wherein tag comprises a plurality of Raman-scattering moieties,
wherein (i) the Raman spectroscopy peak of the tag on each rNPP analog is distinguishable from the Raman spectroscopy peak of the tag on each of the remaining three rNPP analogs, and (ii) each rNPP analog comprises a base which is different from the base of each of the remaining three rNPP analogs, and
wherein the incorporation of the rNPP analog releases a tagged polyphosphate;
(b) determining the wavenumber of the Raman spectroscopy peak of the tagged polyphosphate released in step (a), so as to thereby determining the identity of the incorporated rNPP analog and the identity of the complementary nucleotide residue in the single-stranded RNA; and
(c) iteratively performing steps (a) and (b) for each nucleotide residue of the single-stranded RNA to be sequenced so as to thereby determining the sequence of the single-stranded RNA.

In an embodiment of the invention, the Raman spectroscopy peak is determined using surface-enhanced Raman spectroscopy (SERS).

In an embodiment, the polymerase is immobilized on a solid surface. In a preferred embodiment, the polymerase is immobilized on a SERS substrate.

In an embodiment, the polymerase is immobilized such that only the tagged polyphosphate released in step (a) is within the detection range of the SERS detector. In another embodiment, the polymerase is immobilized such that the tagged polyphosphate released in step (a) is within a cavity on the SERS substrate.

This invention even further provides a method for detecting interaction of a plurality of predetermined compounds comprising:

(a) contacting at least a first predetermined compound immobilized on a solid surface with a solution containing at least a second predetermined compound, wherein the second predetermined compound having attached thereto a tag comprises a plurality of Raman-scattering moieties, under conditions permitting binding of said at least first and second predetermined compounds such that only said second predetermined compound bound to said immobilized first predetermined compound is within the detection range of a detector; and (b) performing Raman spectroscopy, wherein detection of a Raman spectroscopy peak indicating presence of the tag and binding of said at least first and second predetermined compounds, so as to thereby detecting the interaction of the plurality of predetermined compounds.

In an embodiment of the invention, the Raman spectroscopy peak is determined using surface-enhanced Raman spectroscopy (SERS).

In an embodiment, the solid surface is a SERS substrate.

In an embodiment, the predetermined compound is immobilized via covalent or ionic bonds.

In certain embodiments, at least one of the predetermined compounds is a protein. In a preferred embodiment, the protein is an antibody or an antigen.

In certain embodiments, at least one of the predetermined compounds is non-proteinaceous. In an embodiment, the non-proteinaceous compound is a single stranded or double-stranded DNA molecule, an RNA molecule, including microRNA (miRNA) or messenger (RNA), or an oligonucleotide.

In an embodiment of the invention, at least one of the predetermined compounds is an aptamer.

In an embodiment of the invention, the tag attaches to the predetermined compound via a cleavable linker. In a preferred embodiment, the cleavable linker is a photocleavable linker or a chemically cleavable linker.

In an embodiment, a plurality of identical predetermined compounds is immobilized on the solid surface. In another embodiment, a plurality of different predetermined compounds is immobilized on the solid surface.

In an embodiment of the invention, the solution comprises a plurality of different predetermined compounds, wherein the tag attached to each predetermined compound is distinguishable from any tag attached to any other predetermined compound present in the solution.

In an embodiment of the invention disclosed herein, each of the plurality of Raman-scattering moieties has a Raman spectroscopy peak with wave number from 2000 $cm^{-1}$ to 2300 $cm^{-1}$.

In certain embodiments, each of the plurality of Raman-scattering moieties is selected from the group consisting of —N=N=N, —C≡N, —C≡CH, and —C≡C—$CH_3$.

In certain embodiments of the invention, the tag comprising a plurality of identical Raman-scattering moieties. In other embodiments, the tag comprising a plurality of different Raman-scattering moieties.

In certain specific embodiments, the tag comprises 3, 9, or 27 Raman-scattering moieties.

In an embodiment, the plurality of Raman-scattering moieties forms a linear tag. In another embodiment, the plurality of Raman-scattering moieties forms a non-linear tag. In a preferred embodiment, the non-linear tag is a dendrimer tag.

In an embodiment, the tag has a Raman spectroscopy peak with wavenumber from 2125 $cm^{-1}$ to 2260 $cm^{-1}$.

In an embodiment of the invention, the linker is selected from the group consisting of O, NH, S, $CH_2$, amino acids, peptides, proteins, carbohydrates, polyethylene glycols of different length and molecular weights, aliphatic acids, aromatic acids, alcohols or thiol groups (substituted or unsubstituted), cyano groups, nitro groups, alkyl groups, alkenyl groups, alkynyl groups, and azido groups.

For the foregoing embodiments, each embodiment disclosed herein is contemplated as being applicable to each of the other disclosed embodiments. In addition, the elements recited in the compound embodiments can be used in the composition and method embodiments described herein and vice versa.

As used herein, and unless stated otherwise, each of the following terms shall have the definition set forth below.

| | |
|---|---|
| A | Adenine; |
| C | Cytosine; |
| G | Guanine; |
| T | Thymine; |
| U | Uracil; |
| DNA | Deoxyribonucleic acid; |
| RNA | Ribonucleic acid; |

"Nucleic acid" shall mean, unless otherwise specified, any nucleic acid molecule, including, without limitation, DNA, RNA and hybrids thereof. In an embodiment the nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Solid substrate" shall mean any suitable medium present in the solid phase to which a nucleic acid or an agent may be affixed. Non-limiting examples include chips, beads, nanopore structures and columns. In an embodiment the solid substrate can be present in a solution, including an aqueous solution, a gel, or a fluid.

"Hybridize" shall mean the annealing of one single-stranded nucleic acid to another nucleic acid based on the well-understood principle of sequence complementarity. In an embodiment the other nucleic acid is a single-stranded nucleic acid. The propensity for hybridization between nucleic acids depends on the temperature and ionic strength of their milieu, the length of the nucleic acids and the degree of complementarity. The effect of these parameters on hybridization is well known in the art (see Sambrook J, Fritsch E F, Maniatis T. 1989. Molecular cloning: a laboratory manual. Cold Spring Harbor Laboratory Press, New York.). As used herein, hybridization of a primer sequence, or of a DNA extension product, to another nucleic acid shall mean annealing sufficient such that the primer, or DNA extension product, respectively, is extendable by creation of a phosphodiester bond with an available nucleotide or nucleotide analog capable of forming a phosphodiester bond.

"Antibody" shall include, without limitation, (a) an immunoglobulin molecule comprising two heavy chains and two light chains and which recognizes an antigen; (b) a polyclonal or monoclonal immunoglobulin molecule; and (c) a monovalent or divalent fragment thereof. Immunoglobulin molecules may derive from any of the commonly known classes, including but not limited to IgA, secretory IgA, IgG, IgE and IgM. IgG subclasses are well known to those in the art and include, but are not limited to, human IgG1, IgG2, IgG3 and IgG4. Antibodies can be both naturally occurring and non-naturally occurring. Furthermore, antibodies include chimeric antibodies, wholly synthetic antibodies, single chain antibodies, and fragments thereof. Antibodies may be human or nonhuman. Antibody fragments include, without limitation, Fab fragments, Fv fragments and other antigen-binding fragments.

"Apatmer" shall mean single-stranded DNA or RNA, or peptide that can bind to pre-selected targets, including proteins and peptides, with high affinity and specificity. These molecules can assume a variety of shapes due to their propensity to form helices and single-stranded loops. Apatmers are used as sensors, and therapeutic tools, and to regulate cellular processes, as well as to guide drugs to their specific cellular targets. Apatmer's specificity and characteristics are not directly determined by their primary sequence, but instead by their tertiary structure.

As used herein, unless otherwise specified, a base which is "different from" another base or a recited list of bases shall mean that the base has a different structure from the other base or bases. For example, a base that is "different from" adenine, thymine, and cytosine would include a base that is guanine or a base that is uracil.

As used herein, unless otherwise specified, a tag moiety which is different from the tag moiety of a referenced molecule means that the tag moiety has a different chemical structure from the chemical structure of the other/referenced tag moiety.

In some embodiments of the invention, vibrational spectroscopy is used to detect the presence of incorporated nucleotide analogs. Vibrational spectroscopy is a spectrographic analysis where the sample is illuminated with incident radiation in order to excite molecular vibrations. Vibrational excitation, caused by molecules of the sample absorbing, reflecting or scattering a particular discrete amount of energy, is detected and can be measured. The two major types of vibrational spectroscopy are infrared (usually FTIR) and Raman. If FTIR is employed, then the IR spectra of the nucleotide analogs are measured. If Raman is employed, then the Raman spectra of the nucleotide analogs is measured (for example of the nucleotide analogs and in the methods described herein).

In certain embodiments, the polymerase, single-stranded DNA, RNA, primer, or probe is bound to the solid substrate via 1,3-dipolar azide-alkyne cycloaddition chemistry. In an embodiment the polymerase, DNA, RNA, primer, or probe is bound to the solid substrate via a polyethylene glycol molecule. In an embodiment the polymerase, DNA, RNA, primer, or probe is alkyne-labeled. In an embodiment the polymerase, DNA, RNA, primer, or probe is bound to the solid substrate via a polyethylene glycol molecule and the solid substrate is azide-functionalized. In an embodiment the polymerase, DNA, RNA, primer, or probe is immobilized on the solid substrate via an azido linkage, an alkynyl linkage, or biotin-streptavidin interaction. Immobilization of nucleic acids is described in Immobilization of DNA on Chips II, edited by Christine Wittmann (2005), Springer Verlag, Berlin, which is hereby incorporated by reference. In an embodiment the DNA is single-stranded DNA. In an embodiment the RNA is single-stranded RNA.

In other embodiments, the solid substrate is in the form of a chip, a bead, a well, a capillary tube, a slide, a wafer, a filter, a fiber, a porous media, a porous nanotube, or a column. This invention also provides the instant method, wherein the solid substrate is a metal, gold, silver, quartz, silica, a plastic, polypropylene, a glass, or diamond. This invention also provides the instant method, wherein the solid substrate is a porous non-metal substance to which is attached or impregnated a metal or combination of metals. The solid surface may be in different forms including the non-limiting examples of a chip, a bead, a tube, a matrix, a nanotube. The solid surface may be made from materials common for DNA microarrays, including the non-limiting examples of glass or nylon. The solid surface, for example beads/micro-beads, may be in turn immobilized to another solid surface such as a chip.

In one embodiment, the solid surface is a SERS-prepared surface designed specifically for detection of a label nucleotide. The surface may include one or more nanoplasmonic antenna, wherein the nanoplasmonic antenna may be a nanoplasmonic bowtie antenna. In one embodiment, the nanoplasmonic bowtie antenna comprises crossed-bowtie structure in which one pair of triangles couples to incident field, while another pair of triangles couples to Raman scattered field in an orthogonal polarization. It is also contemplated that the nanoplasmonic antenna may be an array of antennas. In addition, the nanoplasmonic antenna may include DNA functionalized sites, and may have a gap size range from 50 nm to 8 nm. In another embodiment, a DNA polymerase is immobilized within the gap.

In another embodiment, the surface comprises a DNA origami scaffold or an array of DNA origami scaffolds. It is also contemplated that the DNA origami scaffold further comprising a primer molecules positioned between Au and Ag nanoparticles and nanorods located at specified binding sites.

In a further embodiment, the surface comprises plasmonic crystals or an array of plasmonic structures. For example, the plasmonic structures may be periodic TiO—Au—TiO structures.

In various embodiments the polymerase, nucleic acid samples, DNA, RNA, primer, or probe are separated in discrete compartments, wells or depressions on a surface.

In this invention methods are provided wherein about 1000 or fewer copies of the polymerase, nucleic acid sample, DNA, RNA, primer, or probe, are bound to the substrate. This invention also provides the instant methods wherein $2 \times 10^7$, $1 \times 10^7$, $1 \times 10^6$ or $1 \times 10^4$ or fewer copies of the polymerase, nucleic acid sample, DNA, RNA, primer, or probe are bound to the substrate.

In some embodiments, the immobilized polymerase, nucleic acid sample, DNA, RNA, primer, or probe is immobilized at a high density. This invention also provides the instant methods wherein over or up to $1 \times 10^7$, $1 \times 10^8$, $1 \times 10^9$ copies of the polymerase, nucleic acid sample, DNA, RNA, primer, or probe, are bound to the solid substrate.

In other embodiments of the methods and/or compositions of this invention, the DNA is single-stranded. In an embodiment of the methods or of the compositions described herein, the RNA is single-stranded.

In certain embodiments, UV light is used to photochemically cleave the photochemically cleavable linkers and moieties. In an embodiment, the photocleavable linker is a 2-nitrobenzyl moiety. In an embodiment of the processes and methods described herein monochromatic light is used to irradiate Raman-label-containing nucleotide analogs (e.g. incorporated into a primer or DNA extension product) so as to elicit a signal measurable by Raman spectroscopy. In one such embodiment, the laser is a 532 nm, 633 nm, or 785 nm laser. In another such embodiment, near infra-red light is used to irradiate Raman-label-containing nucleotide analogs. In certain embodiments of the processes and methods of this invention near infra-red light is used to irradiate Raman-label-containing polynucleotide analogs.

A "nucleotide residue" is a single nucleotide in the state it exists after being incorporated into, and thereby becoming a monomer of, a polynucleotide. Thus, a nucleotide residue is a nucleotide monomer of a polynucleotide, e.g. DNA, which is bound to an adjacent nucleotide monomer of the polynucleotide through a phosphodiester bond at the 3' position of its sugar and is bound to a second adjacent nucleotide monomer through its phosphate group, with the exceptions that (i) a 3' terminal nucleotide residue is only bound to one adjacent nucleotide monomer of the polynucleotide by a phosphodiester bond from its phosphate group, and (ii) a 5' terminal nucleotide residue is only bound to one adjacent nucleotide monomer of the polynucleotide by a phosphodiester bond from the 3' position of its sugar.

Because of well-understood base-pairing rules, determining the wavenumber of the Raman spectroscopy peak of a dNTP analog incorporated into a primer or DNA extension product, and thereby the identity of the dNTP analog that was incorporated, permits identification of the complementary nucleotide residue in the single stranded polynucleotide that the primer or DNA extension product is hybridized to. Thus, if the dNTP analog that was incorporated has a unique wavenumber in the Raman spectroscopy peak identifying it as comprising an adenine, a thymine, a cytosine, or a guanine, then the complementary nucleotide residue in the single stranded DNA is identified as a thymine, an adenine, a guanine or a cytosine, respectively. The purine adenine (A) pairs with the pyrimidine thymine (T). The pyrimidine cytosine (C) pairs with the purine guanine (G). Similarly, with regard to RNA, if the dNTP analog that was incorporated comprises an adenine, a uracil, a cytosine, or a guanine, then the complementary nucleotide residue in the single stranded RNA is identified as a uracil, an adenine, a guanine or a cytosine, respectively.

Incorporation into an oligonucleotide or polynucleotide (such as a primer or DNA extension strand) of a dNTP analog means the formation of a phosphodiester bond between the 3' carbon atom of the 3' terminal nucleotide residue of the polynucleotide and the 5' carbon atom of the dNTP analog resulting in the loss of pyrophosphate from the dNTP analog.

As used herein, a deoxyribonucleoside polyphosphate (dNPP) analog, unless otherwise indicated, is a dNPP having connected via a linker to the terminal phosphate thereof, a chemical group which has Raman spectroscopy peak with wavenumber of from 2000 cm$^{-1}$ to 2300 cm$^{-1}$ and which does not prevent the dNPP analog from being incorporated into a polynucleotide, such as DNA, by formation of a phosphodiester bond. A deoxyribonucleotide analog residue is deoxyribonucleotide analog which has been incorporated into a polynucleotide and which still comprises its chemical group having a Raman spectroscopy peak with wavenumber of from 2000 cm$^{-1}$ to 2300 cm$^{-1}$. In an embodiment the chemical group has a Raman spectroscopy peak with wavenumber of from 2000 cm$^{-1}$ to 2300 cm$^{-1}$.

As used herein, a ribonucleoside polyphosphate (rNPP) analog, unless otherwise indicated, is an rNPP having connected via a linker to the terminal phosphate thereof, a chemical group which has a Raman spectroscopy peak with wavenumber of from 2000 cm$^{-1}$ to 2300 cm$^{-1}$ and which does not prevent the rNPP analog from being incorporated into a polynucleotide, such as RNA, by formation of a phosphodiester bond. A ribonucleotide analog residue is ribonucleotide analog which has been incorporated into a polynucleotide and which still comprises its chemical group having a Raman spectroscopy peak with wavenumber of from 2000 cm$^{-1}$ to 2300 cm$^{-1}$. In an embodiment the chemical group has a Raman spectroscopy peak with wavenumber of from 2000 cm$^{-1}$ to 2300 cm$^{-1}$.

A Raman spectroscopy system, as can be used in the methods described herein, typically comprises an excitation source (such as a laser, including a laser diode in appropriate configuration, or two or more lasers), a sample illumination system and light collection optics, a wavelength selector (such as a filter or spectrophotometer), and a detection apparatus (such as a CCD, a photodiode array, or a photomultiplier). Interference (notch) filters with cut-off spectral range of ±80-120 cm$^{-1}$ from the laser line can be used for stray light elimination. Holographic gratings can be used. Double and triple spectrometers allow taking Raman spectra without use of notch filters. Photodiode Arrays (PDA) or a Charge-Coupled Devices (CCD) can be used to detect Raman scattered light.

In an embodiment, surface enhanced Raman spectroscopy (SERS) is used which employs a surface treated with one or more of certain metals known in the art to cause SERS effects. In an embodiment the surface is a surface to which the polymerase, polynucleotide, single-stranded DNA, single-stranded RNA, primer, DNA extension strand, or oligonucleotide probe of the methods described herein is attached. Many suitable metals are known in the art. In an embodiment the surface is electrochemically etched silver or treated with/comprises silver and/or gold colloids with average particle size below 20 nm. The wavenumber of the Raman spectroscopy peak of an entity is identified by irradiating the entity with the excitation source, such as a laser, and collecting the resulting Raman spectrum using a detection apparatus. The wavenumber of the Raman spectroscopy peak is determined from the Raman spectrum. In an embodiment, the spectrum measured is from 2000 cm$^{-1}$ to 2300 cm$^{-1}$ and the wavenumber of the Raman spectroscopy peak is the peak wavenumber within that spectrum. In an embodiment the spectrum measured is a sub-range of 2000 cm$^{-1}$ to 2300 cm$^{-1}$ and the Raman spectroscopy peak wavenumber is the peak wavenumber within that spectrum sub-range.

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention.

As used herein, "alkyl" includes both branched and straight-chain saturated aliphatic hydrocarbon groups having the specified number of carbon atoms and may be unsubstituted or substituted. Thus, C1-Cn as in "C1-Cn alkyl" includes groups having 1, 2, . . . , n–1 or n carbons in a linear or branched arrangement. For example, a "C1-C5 alkyl" includes groups having 1, 2, 3, 4, or 5 carbons in a linear or branched arrangement, and specifically includes methyl, ethyl, n-propyl, isopropyl, n-butyl, t-butyl, and pentyl.

As used herein, "alkenyl" refers to a non-aromatic hydrocarbon group, straight or branched, containing at least 1 carbon to carbon double bond, and up to the maximum possible number of non-aromatic carbon-carbon double bonds may be present, and may be unsubstituted or substituted. For example, "C2-C5 alkenyl" means an alkenyl group having 2, 3, 4, or 5, carbon atoms, and up to 1, 2, 3, or 4, carbon-carbon double bonds respectively. Alkenyl groups include ethenyl, propenyl, and butenyl.

The term "alkynyl" refers to a hydrocarbon group straight or branched, containing at least 1 carbon to carbon triple bond, and up to the maximum possible number of non-aromatic carbon-carbon triple bonds may be present, and may be unsubstituted or substituted. Thus, "C2-C5 alkynyl" means an alkynyl group having 2 or 3 carbon atoms and 1 carbon-carbon triple bond, or having 4 or 5 carbon atoms and up to 2 carbon-carbon triple bonds. Alkynyl groups include ethynyl, propynyl and butynyl.

The term "substituted" refers to a functional group as described above such as an alkyl, or a hydrocarbyl, in which at least one bond to a hydrogen atom contained therein is replaced by a bond to non-hydrogen or non-carbon atom, provided that normal valencies are maintained and that the substitution(s) result(s) in a stable compound. Substituted groups also include groups in which one or more bonds to a carbon(s) or hydrogen(s) atom are replaced by one or more bonds, including double or triple bonds, to a heteroatom. Non-limiting examples of substituents include the functional groups described above, and for example, N, e.g. so as to form —CN.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

In the compound structures depicted herein, hydrogen atoms, except on ribose and deoxyribose sugars, are generally not shown. However, it is understood that sufficient hydrogen atoms exist on the represented carbon atoms to satisfy the octet rule.

All combinations of the various elements described herein are within the scope of the invention. All sub-combinations of the various elements described herein are also within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

Disclosed herein is synthesis of new molecules for a novel approach involving the well-established sequencing by synthesis (SBS) protocol, and taking advantage of the high sensitivity of surface enhanced Raman spectroscopy (SERS) [Nie at al. 1997, Hsiao et al. 2011, Kleinman at al. 2011, and Li at al. 2011]. The ability to conduct such a SERS-SBS procedure with a single chemically cleavable Raman tag on all four bases has been demonstrated. By labeling nucleotides with clusters of Raman tags, the approach could achieve sequencing of single DNA molecules.

The overall approach is illustrated in FIG. 1. After nucleotide incorporation by DNA polymerase, the released by-product of this reaction, Raman tag-polyphosphates are obtained and the extended DNA strand is free of any modifications. This is advantageous because such remnants on growing DNA chains can affect their ability to be recognized by polymerase with increasing nucleotide additions, eventually terminating further DNA synthesis. The released Raman tag-attached polyphosphate are assayed to evaluate sequencing sensitivity and accuracy. In initial experiments, Raman tags are tested for their sensitivity before running SBS reactions. Using different Raman tags for the four nucleotides to generate four different tagged-polyphosphates allows the DNA sequence to be determined. As an example, 5'-polyphosphate-tagged deoxynucleosides with templates that permit addition of one or a few nucleotides at a time is used.

Figure 2:
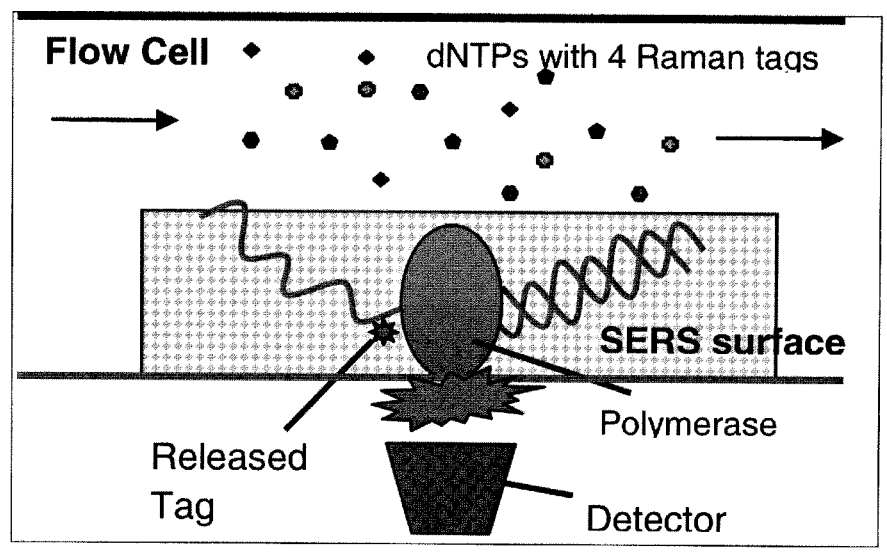
FIG. 2. Scheme of a SERS-SBS platform. A single polymerase is immobilized on a surface-enhanced Raman spectroscopy (SERS) hot spot. Only the perfect matched labeled nucleotide complexes with polymerase and the released tag yields a SERS signal.

Real-time single-molecule detection using the SERS-SBS method is shown in FIG. 2. A polymerase is covalently attached to the SERS substratum at the position of the detector. DNA is threaded through the polymerase and with addition of each nucleotide only the perfectly matched labeled nucleotide complexes with the polymerase. The released tag from the appropriate complementary nucleotide is within range for SERS detection, with unreacted tagged nucleotides at a much greater average distance, thus do not yield a SERS signal. This resembles the approach with the use of zero-mode waveguides; in which case only reacting 5'-phospho linked fluorescent molecules are within the range of the detector [Korlach et al. 2010]. In this case, one could take advantage of the nano-gap hot spots between gold particles that produce SERS, with the SERS substrate acts as a simple "waveguide".

I. SERS-SBS with Nucleotides Bearing Single Raman Tag

The ability to generate single Raman moiety-bearing nucleotide reversible terminators and their use for continuous DNA SBS reactions has been demonstrated. SERS with four different tags, and the ability of DNA polymerase to accept nucleotides with extensive modifications at their 5'-phosphate terminus, also have been shown.

I.A Incorporation of Long PEGylated 5'-Modified Nucleotides

Figure 3:
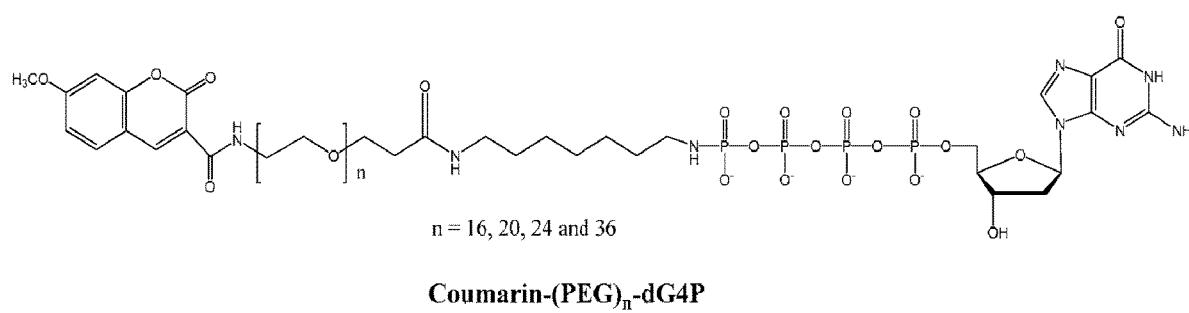
FIG. 3. Coumarin-PEG-dG4P compounds. General structure of the coumarin-PEG-dG4P compounds is shown at top. MALDI-TOF mass spectra are shown for the DNA extension products with coumarin-(PEG)$_{24}$-dG4P (left) or coumarin-(PEG)$_{36}$-dG4P nucleotides (right). Both are incorporated at ~100% efficiency, and yield identical DNA extension products after release of the P3-(PEG)$_n$-coumarin tags. The same results are obtained for coumarin-(PEG)$_{16}$-dG4P and coumarin-(PEG)$_{20}$-dG4P.
Figure 3:
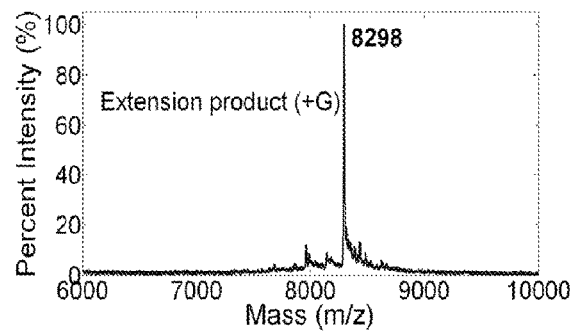
Figure 3:
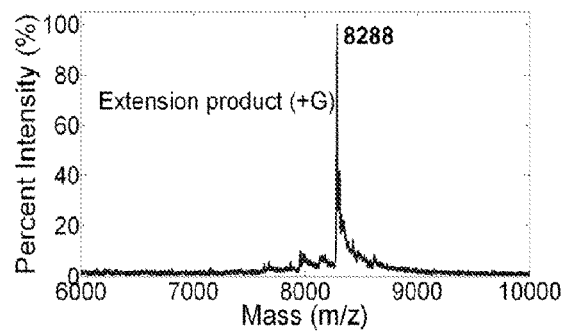

The ability of DNA polymerase to accurately and efficiently incorporate dGTP with long coumarin labeled polyethylene glycol chains (16, 20, 24 and 36 PEG units) attached to the terminal phosphate of 5'-tetraphosphates has been shown. During the polymerase reaction, after cleavage of the α-β phosphate bond, close to 100% incorporation of the natural dGTP was obtained for all four coumarin PEG-modified dG4Ps as monitored by near absence of primer peaks (~7950 d) in MALDI-TOF mass spectra (FIG. 3). This shows that polymerase is forgiving of extensive modifications, as has been reported previously [Kumar et al. 2005, Sood et al. 2005, and Korlach et al. 2008]. This also addresses the concern whether one will be able to incorporate nucleotides possessing the tagged dendrons on the 5'-terminal phosphates, especially larger ones with 9 or even 27 tags.

I.B SERS-SBS with Single Tags

Figure 4:
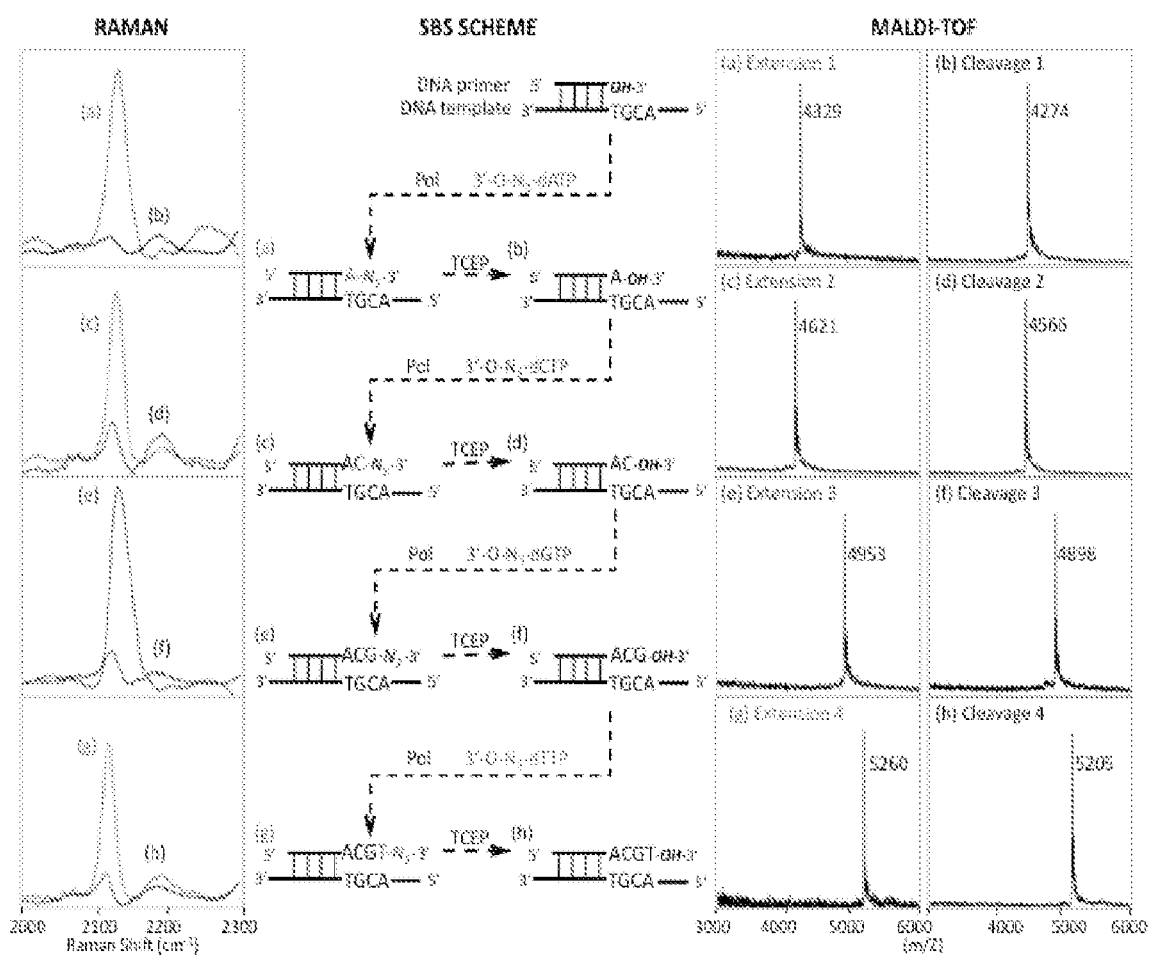
FIG. 4. Scheme for continuous DNA Sequencing By Synthesis (middle) using reversible terminators, 3'-O-azidomethyl-dNTPs, with the expected Raman (left) and MALDI-TOF MS spectra (right) obtained at each step. Only the 1950-2300 cm$^{-1}$ Raman interval is shown, the azide peak appearing at Raman shift ~2125 cm$^{-4}$. Pol=DNA polymerase.

As shown in FIG. 4, 4 rounds of SERS SBS with 3'-O-azidomethyl dATP, 3'-O-azidomethyl dCTP, 3'-O-azidomethyl dGTP, and 3'-O-azidomethyl dTTP are conducted in turn, with intermediate cleavage of the 3'-blocking groups to restore the free hydroxyl moiety on the base to allow the next cycle of synthesis. A 3'-O-azidomethyl modified complementary nucleotide is incorporated into the growing strand of the DNA in a polymerase reaction. After removing unreacted nucleotides, the DNA extension products were spotted on a Klarite SERS substrate for Raman detection. The appearance of strong specific Raman peaks for the azido group at ~2125 $cm^{-4}$ indicated incorporation of 3'-azidomethyl-dNTPs into the DNA strand (FIG. 4 left). Treatment with 50 mM TCEP [Tris(2-carboxyethyl)phosphine] solution cleaved the azidomethyl group, with the disappearance of its characteristic Raman peak. This regenerated the 3'-OH on the DNA, allowing initiation of the next cycle. In this manner, all 4 $N_3$-dNTPs (A, C, G, T) are continuously incorporated into the growing strand of the DNA with high efficiency. The cleavage reaction completely removed and destroyed the $N_3$ blocking group, which does not interfere with subsequent detection. The newly produced DNA contains only natural, unmodified bases, which yield high quality SBS data. The DNA extension and cleavage products were also characterized by MALDI-TOF-mass spectroscopy as shown in FIG. 4 right.

I.C SERS with Different Raman Tags

Figure 5:
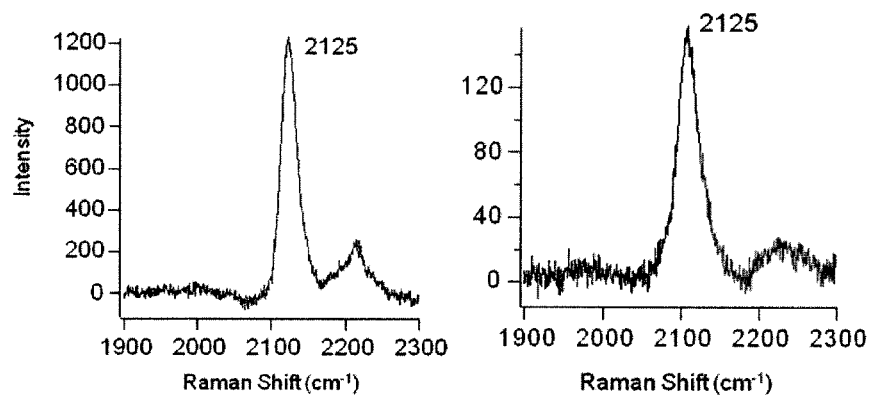
FIG. 5. Surface-enhanced Raman spectroscopy for azido group in compound 2-azido-3-(benzyloxy)propanoic acid. Typical experimental Raman spectrum of 1 µM solution on Klarite substrate (left) and corresponding reference spectrum of 100 mM solution dried on aluminum coated slide (right). An enhancement factor of ~10$^6$ was obtained.

An example of SERS using commercial SERS substrates (Klarite chips) is shown in FIG. 5 for the azido moiety where ~$10^6$-fold enhancement was obtained. SERS was also demonstrated with cyano and methyl-substituted alkyne containing compounds.

II. Design and Synthesis of Terminal Phosphate-Tagged Nucleoside-5'-tetraphosphates with 3 Raman Signal Moieties A set of four nucleotides (A, C, G, and T), each with a unique cluster of 3 identical Raman-scattering moieties (—C≡N, —N=N=N, —C≡CH, or —C≡C—CH$_3$) are attached as dendrons to the 5'-terminal phosphate of the nucleotides. These nucleotide analogs are not expected to present difficulties in polymerase reactions, based on experience with other very extensive modifications at this site, and should provide enhanced Raman signals relative to singly tagged nucleotides.

Figure 6:
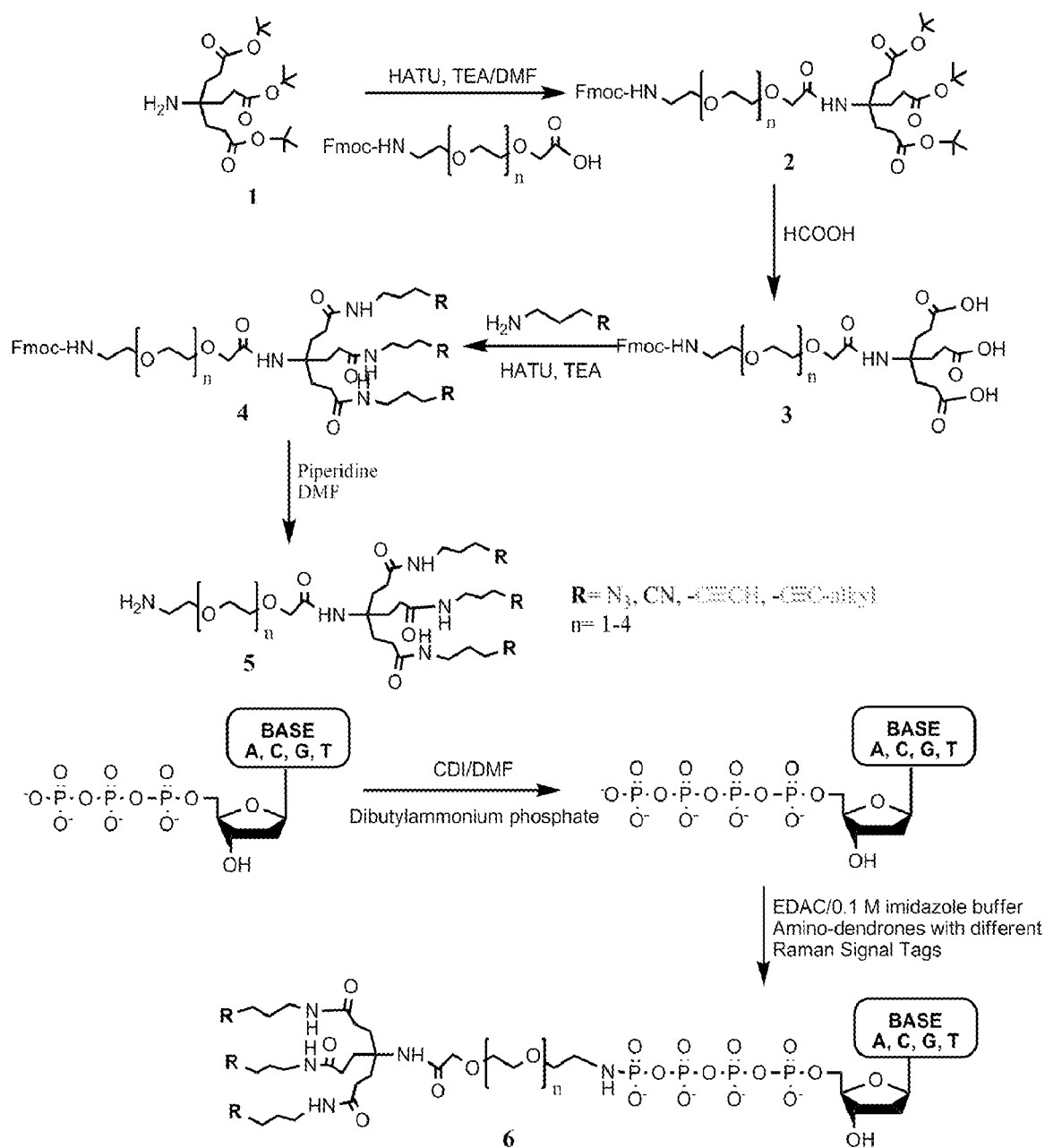
FIG. 6. Synthesis of phosphate-labeled-nucleoside-5'-tetraphosphates with 3 Raman-scattering moieties.

Synthesis of dendrons with 3 Raman signal moieties can be carried out as shown in FIG. 6. First, the commercially available amino-triester (1) is reacted with Fmoc-protected amino-PEG-NHS ester followed by hydrolysis with formic acid to provide Fmoc-protected amino-PEG-triacid (3) [Ornelas et al. 2009]. The acid groups in compound (3) are converted with HATU/DMF to active esters and then reacted with the desired Raman signal carrying molecules, such as aminopropyl azide, 3-amino-propylnitrile, propargyl amine, or pent-3-yn-1-amine to furnish compound (4) which is then deprotected with piperidine/DMF to give the desired amino terminated 3-Raman tag attached dendron (5), ready to react with a nucleoside-5'-tetraphosphate.

For synthesis of Raman substrates tagged at the terminal phosphate of the nucleoside-5'-tetraphosphates, for instance, the corresponding triphosphate is first reacted with CDI in DMF to activate the terminal phosphate group which is then reacted with phosphoric acid to give the tetraphosphate (FIG. 6). The terminal phosphate on the tetraphosphate is further activated with EDAC in 0.1M imidazole buffer followed by reaction with an appropriate Raman group tagged dendron to provide the desired Raman tagged nucleoside-5'-tetraphosphate.

III. Design and Synthesis of Terminal Phosphate-Tagged Nucleoside-5'-tetraphosphates with 9 Raman Signal Moieties Similarly, based on the strategies established in section (II), four nucleotides are tagged with dendrons containing 9 identical Raman-scattering groups. These nucleotide analogs are expected to provide very strong Raman signals.

Figure 7:
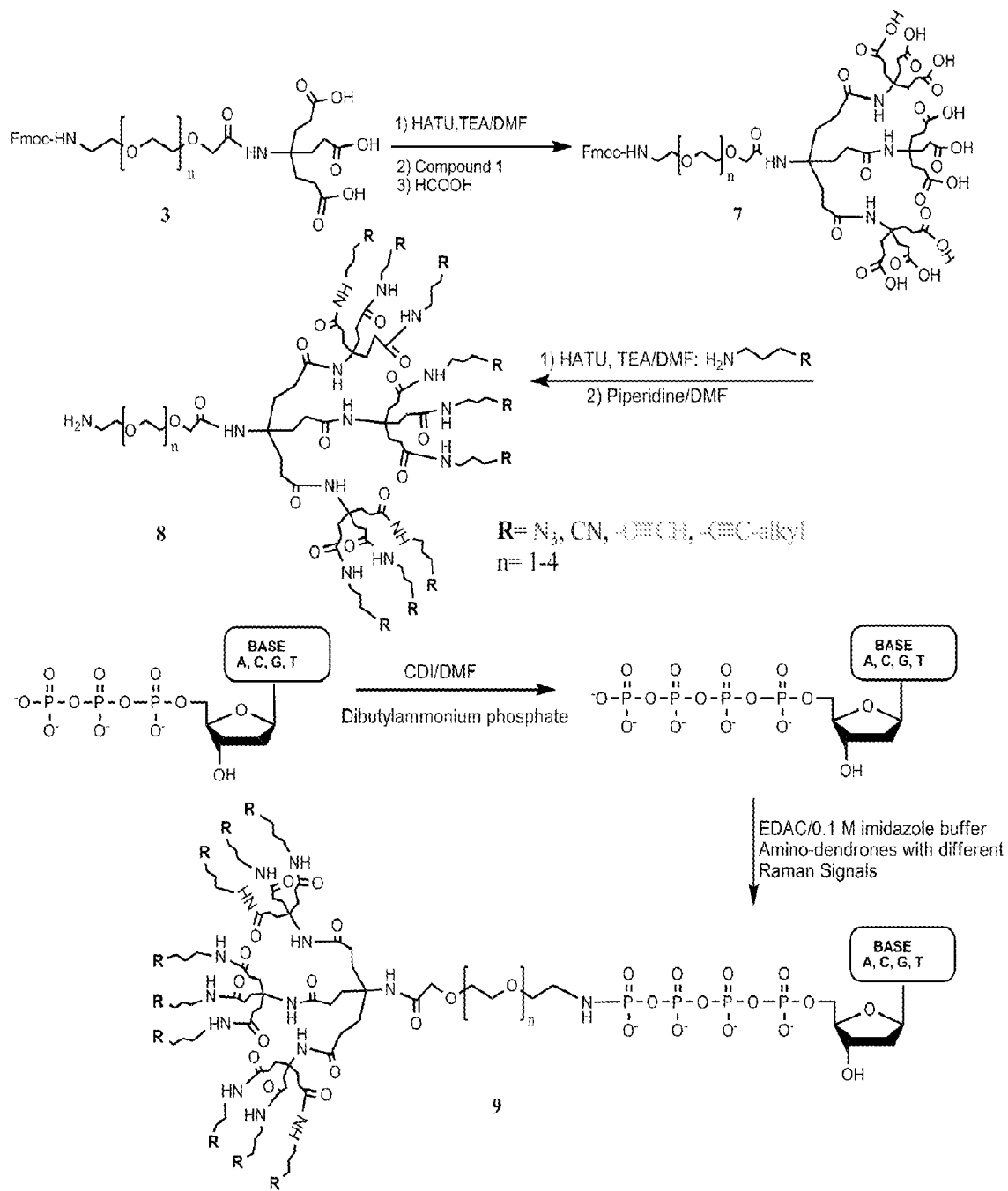
FIG. 7. Synthesis of phosphate-labeled-nucleoside-5'-tetraphosphates with 9 Raman-scattering moieties.

Synthesis of 9 Raman signal moiety carrying dendrons is carried out as shown in FIG. 7. Compound (3) is first activated with HATU/DMF followed by reaction with amino-triester to provide compound (7) with nine acid groups. The acid groups are further activated and reacted with appropriate Raman tagged molecules, such as aminopropyl azide, 3-aminopropyl nitrile, propargyl amine, or pent-3-yn-1-amine to furnish compounds which are then deprotected with piperidine/DMF to give the desired amino-terminated 9-Raman-tag-attached dendron (8), ready to react with the nucleoside-5'-tetraphosphates.

The activation of triphosphate and reaction with dendron (8) follows the same reaction sequence as shown in FIG. 6. Synthesis of Raman-tagged-nucleoside-5'-tetraphosphates are shown since tetraphosphates are better substrates for DNA polymerases than the corresponding triphosphates [Kumar at al. 2005, Rood et al. 2005, and Korlach et al. 2008].

IV. Polymerase Incorporation of Synthesized Nucleotides

Nucleotides generated in sections (II) and (III) are tested in DNA polymerase reactions. Incorporation of nucleotides are tracked using MALDI-TOF MS, a procedure for analysis of incorporation of a wide variety of nucleotide analogs. Templates are designed to allow addition of one or more nucleotides at a time.

During the polymerase reaction, the tag-containing dendrons are released due to cleavage of the bond between the α and β phosphates. This leave the primer chain extended by dAMP, dCMP, dGMP or dTMP, whichever is complementary to the template strand. Using short primers of less than 20 bases hybridized to linear templates, successful extension reactions are identified using MALDI-TOF MS as the disappearance of a primer peak and the appearance of a peak representing a primer extended by a single base. The mass of the extension peak thus indicates which base was added. By designing templates with 1, 2, or more consecutive As, Cs, Gs, or Ts, one could demonstrate the accuracy and processivity of the polymerase reactions. As an alternative, primer-loop-templates may be used to increase the efficiency of the reactions.

Nucleotides with 3 Raman signaling moieties are incorporated with high efficiency and accuracy. There is no difficulty with incorporation of nucleotides with 9 Raman signal moieties, though incorporation reaction parameters need to be further optimized for high efficiency. Alternatively, instead of dendron disposed tags, linear tags such as those for the coumarin-PEG-nucleotides may be used.

V. Raman Enhancement by 3- and 9-Member Cluster Tags

The nucleotides are tested for their ability to generate Raman signals on commercial SERS substrates, such as Klarite SERS surfaces produced by Renishaw Diagnostics (Glasgow, UK). The 3-tag and 9-tag nucleotides are compared with 1-tag nucleotides for increased SERS signal.

Surface enhanced Raman signals obtained using nucleotides containing single Raman tag and the necessary methodology for testing SERS have been demonstrated in (I) above. Results obtained with these compounds are compared with the 3- and 9-member Raman cluster tags described in (II) and (III). Glass or aluminum coated slides are used to obtain baseline Raman measurements and measure the level of enhancement on Klarite slides. Different Raman tags with distinct wavenumbers (e.g., azido at 2125 cm$^{-1}$, alkyne at 2139 cm$^{-1}$, methyl-substituted alkyne at 2250 cm$^{-1}$, and cyano at 2260 cm$^{-1}$) are tested for their relative enhancement on this substrate. Increasing numbers of tags leads to a higher likelihood of obtaining productive SERS, and thus higher sensitivity and signals. Depending on the results, the test may even extend to higher numbers of Raman tags since simply extending the synthesis method (reacting compounds (7) and (1) and proceeding as in FIG. 7) yields 27 tags.

Discussion

While approaches developed and commercialized in the last half decade, methods which usually referred to as next generation sequencing are still too costly and time-consuming for routine use. Many of these rely on real-time sequencing, especially sequencing by synthesis (SBS), and typically require fluorescently labeled nucleotides. Single molecule SBS is a particular need, as it can avoid amplification biases in expression and epigenetic analyses, and overcome potential errors and read length limitations introduced by asynchronous extension of multiple strands.

Although detection of fluorescently labeled molecules offers higher sensitivity than standard Raman spectroscopy, application of nanophotonic theory and use of metal colloids and microfabricated surfaces have dramatically increased Raman sensitivity by many orders of magnitude, with single molecule measurements having been described [Nie et al. 1997, Hsiao et al. 2011, and Kleinman et al. 2011]. Nonetheless, the consistency of measurements with surface-enhanced Raman scattering (SERS) is limited by the requirement for appropriate disposition of the molecule to be measured relative to the surface.

Likelihood of SERS is increased by taking advantage of nucleotide analogs with multiple identical Raman tags (for example, cluster tags of 3 or 9 units) displayed on dendrons linked to the 5'-terminal phosphate group of the nucleotides, hence displaying various angular vectors relative to the backbone. With a different Raman scattering entity on each of the 4 nucleotides, they can be added at the same time and correct extension can be monitored by the resulting Raman signature. Data demonstrated (1) SERS with tags (—N=N=N; —C≡N; —C≡CH, —C≡C—CH$_3$) displaying Raman shifts (2000-2300 cm$^{-1}$) [Socrates 2001] that are distinct from those of all the other reaction components including DNA and proteins; (2) multi-step polymerase reactions with all four nucleotides containing a single chemically cleavable Raman tag (azidomethyl groups attached to the 3'-OH group of all four nucleotides); and (3) the ability of polymerase to accept nucleotides with extensive modifications at the 5' phosphate (for example, up to 49 unit PEG molecules).

Disclosed herein is design and synthesize of a novel set of nucleotide analogs which enables a new sequencing approach with the potential to lower costs and increase accuracy. Nucleotides are modified at the 5'-terminal phosphate with clusters of small chemical groups with unique Raman signatures. Incorporation of a complementary nucleotide leads to the release of these base-specific Raman tags which can be detected using surface-enhanced Raman scattering (SERS). The presence of multiple Raman scattering groups contribute to high sensitivity, and the nucleotides regenerated at each step bears no traces of modification, enabling long reads. This cluster Raman tagging approach is superior to fluorescent labeling, because multiple fluorophores on a single nucleotide will lead to fluorescence quenching.

Synthesis of sets of nucleotides with 3- and 9-Raman-tag nucleotides, test of their incorporation efficiency, and the ability of the tags to produce strong and specific Raman signals using commercial SERS templates are demonstrated above. Consecutive addition of four nucleotides with single chemically cleavable Raman tags in polymerase reactions and their detection by SERS have been shown as well. Therefore, these nucleotides may be incorporate into a platform allowing continuous "4-Raman signature" extension and detection with immobilized polymerases on SERS substrates to accomplish real-time single-molecule sequencing.

In developing a full SERS-SBS real-time single-molecule sequencing platform, it is essential to measure the Raman signatures of the released tags while avoiding measurement of the tagged nucleotides that are far away from the SERS hot spot. By adopting the system to a solid-state platform in which the DNA polymerase molecules are covalently attached to the SERS substrate; analogous to the existing system using waveguides. In such a system, only released tags and the perfect match nucleotides bearing the Raman cluster tags complexed with the immobilized polymerase are close enough to the surface to generate SERS and be measured.

In summary, new substrates for conducting SERS-SBS are generated that bear several advantageous features. Conditions are established for these new molecules to be incorporated into the growing strand of DNA in the polymerase reaction with high fidelity and efficiency and to provide high signals with fairly standard SERS surfaces, providing for a single molecule sequencing strategy using a broad array of newer SERS designs.

VI. Detection of Protein-Protein Interactions

Also disclosed herein is an approach to obtain consistently enhanced Raman signals, by tagging proteins with clusters of chemical groups that display Raman scattering at a particular wavenumber that is distinct from other molecules in the assay. This approach uses clusters of the Raman tag rather than a single instance of the moiety.

Despite its impressive potential for signal enhancement, a major problem with surface-enhanced Raman Spectroscopy (SERS) is its consistency, which is related in part to the disposition of the Raman scattering group relative to the gold particles or nanocrystals.

To solve this problem, clusters containing several copies of the Raman scattering chemical group placed in a geometry that increases the likelihood that at least one and perhaps a few of the tags in each cluster will have an appropriate orientation to best take advantage of SERS (e.g., will fit in the gap between two gold particles or into the confines of a nanocrystal) are developed. While the many orders of magnitude enhancement is still due to the SERS, this approach provides a higher likelihood that this enhancement will occur for any individual molecule due to the presence of an array of 10-20 tags with various orientations.

In the range of 2000-2200 cm$^{-1}$, a region of the Raman spectrum where proteins and most other biological molecules do not display peaks, one can utilize tags that do have discrete peaks in this window, including azido (2125 cm$^{-1}$), cyano (2259 cm$^{-1}$), alkyne (2138 cm$^{-1}$), and methylalkyne (2249 cm$^{-1}$). To get more than four signatures, mixtures of cyano, alkyne, azido, etc., on the same dendrimer may also be used.

Proteins are readily labeled covalently with tags by taking advantage of exposed reactive groups (e.g., amino of lysine or arginine; sulfhydryl of cysteine; hydroxyl of serine or threonine; carboxyl of aspartic acid or glutamic acid). Traditionally, these tags may be radioisotopes, fluorophores, colorimetric groups, etc. In this approach, small Raman tags arranged in series (polymers), cycles (multi-ring or similar structures), or parallel (branched dendrimers) are used. Tags may be attached via chemically cleavable or photocleavable linkers, though this is not necessary for most of the uses described below.

Figure 8:
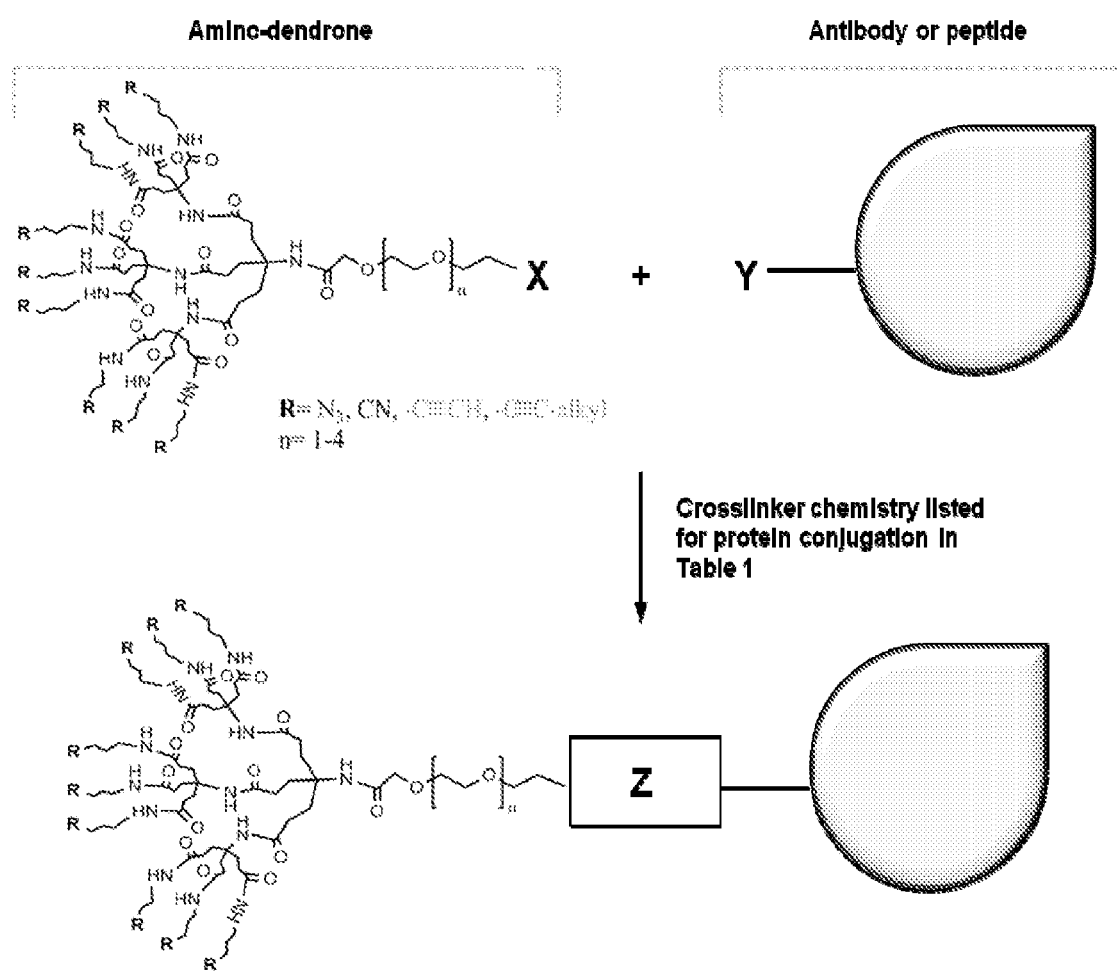
FIG. 8. Various crosslinking strategies to conjugate a 9-Raman-scattering moieties tag with proteins, such as antibodies or peptides. A small number of protein functional groups (Y) comprise selectable targets for practical conjugation methods. A number of chemical reactive groups (X) have been characterized and used to target the protein functional groups for crosslinking.
Figure 9:
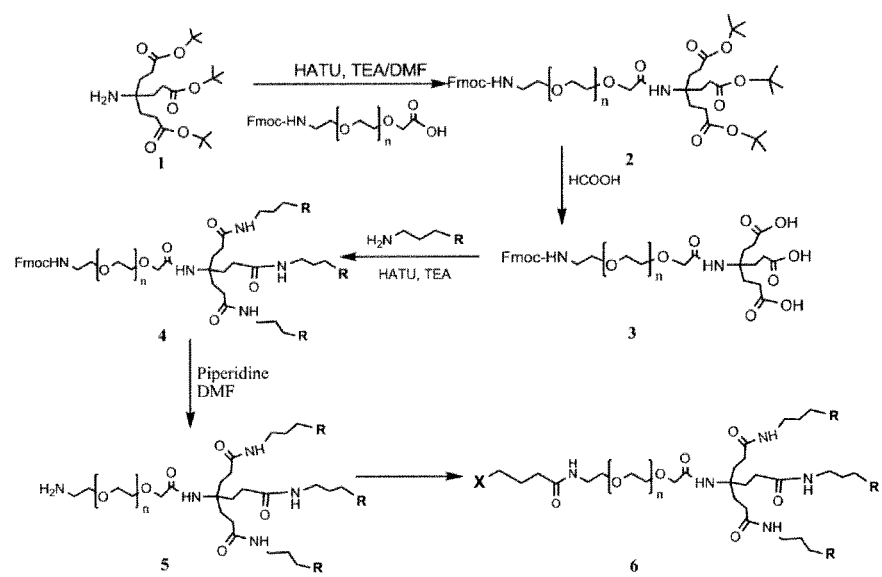
FIG. 9. Scheme for synthesis of arbitrary proteins conjugated with a dendrimer tag comprising 3 Raman-scattering moieties.
Figure 10:
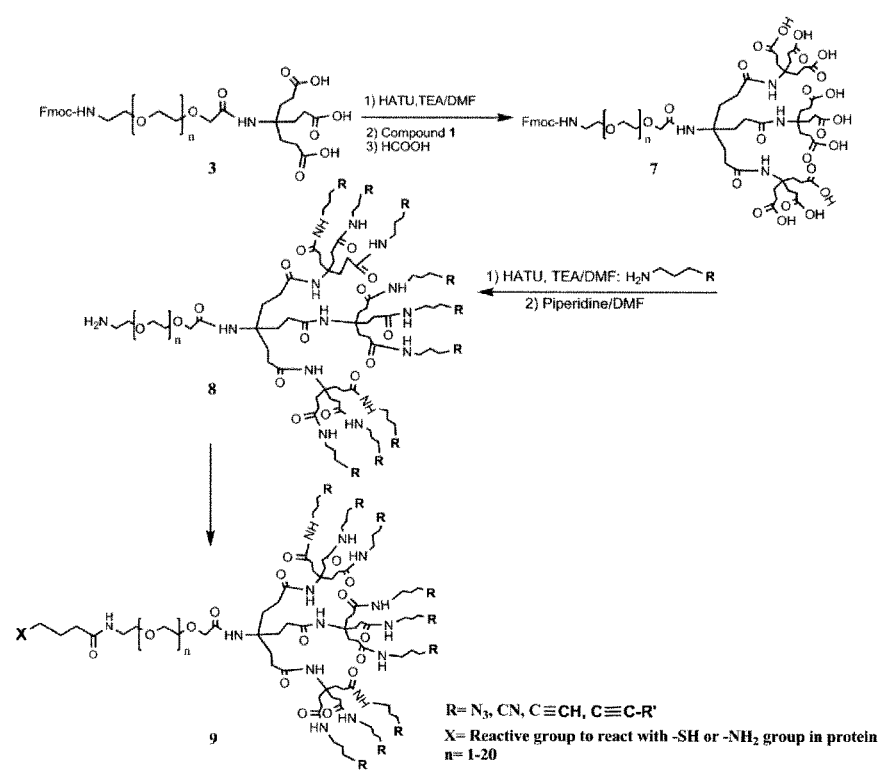
FIG. 10. Scheme for synthesis of arbitrary proteins conjugated with a dendrimer tag comprising 9 Raman-scattering moieties.

Various crosslinking strategies to conjugate the 9 Raman-scattering moiety with proteins (antibodies, peptides) is shown in FIG. 8. FIGS. 9 and 10 each shows a synthesis scheme of an arbitrary protein conjugated with a dendrimer tag comprising 3 or 9 Raman-scattering moieties, respectively. A small number of protein functional groups (Y) comprise selectable targets for practical conjugation methods, such as: primary amines (—$NH_2$), carboxyls (—COOH), sulfhydryls (—SH) and carbonyls (—CHO). A number of chemical reactive groups (X) have been characterized and used to target the protein functional groups for crosslinking. A list of exemplary reactive groups are listed below on Table I.

TABLE I

Possible crosslinker reactive groups for protein to amino-dendrone conjugation.

| Reactivity Class (Y) | Chemical Group (X) | Activated Crosslink (Z) |
| --- | --- | --- |
| Carboxyl-to-amine reactive groups | Carbodiimide (e.g., EDC) | Amide bond |
| Amine-reactive groups | NHS ester | Amide bond |
| | Imidoester | Amidine bond |
| Sulfhydryl-reactive groups | Maleimide | Thioether bond |
| | Haloacetyl (Bromo- or Iodo-) | Thioether bond |
| | Pyridyldisulfide | Disulfide bond |
| Aldehyde-reactive groups i.e., oxidized sugars (carbonyls) | Hydrazide | Hydrazone bond |
| | Alkoxyamine | Oxime bond |

In this approach, one of the proteins, generally an untagged protein, is attached via covalent or ionic bonds (e.g. azido-alkyne, amino-NHS ester, amino-carboxyl, or biotin-avidin) to a SERS surface. (Covalent bond induced by reacting an alkyne and azido moiety results in a ring structure that may have a Raman signal of its own in the part of the spectrum of interest. Therefore, such bonds are generally avoided, except in cases when one wants to use such signal as background or for localization.)

Figure 11:
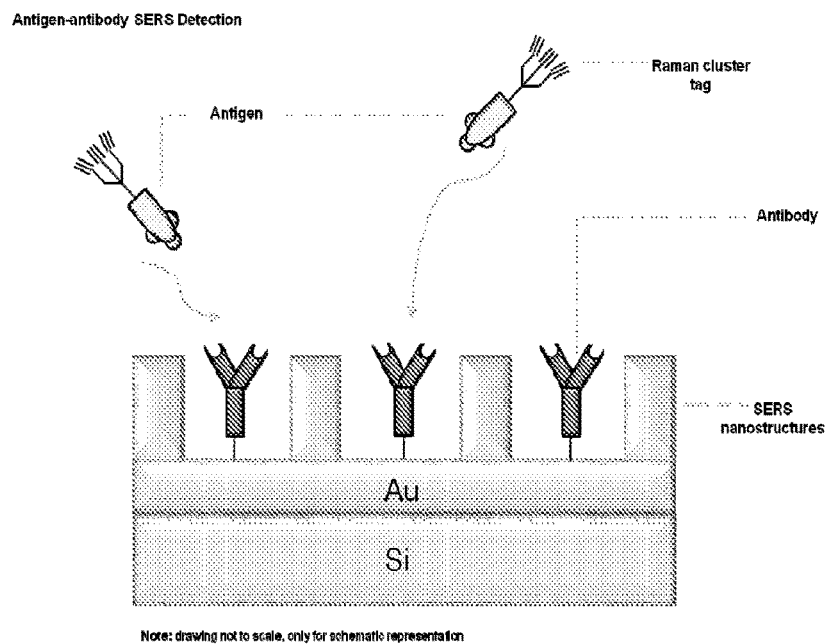
FIG. 11. Scheme of antigen-antibody SERS detection. (A) Antibodies are immobilized on the gold-coated SERS nanostructures using conventional attachment chemistries and the antigen is introduced, which is labeled with a Raman cluster tag. (B) The antibody uniquely recognizes the antigen, allowing the two structures to bind together with precision. The bound antigen is positioned such that the Raman cluster tag is located close to the SERS hotspots upon laser irradiation. Large SERS enhancement is observed due to the mutual interplay between the localized surface plasmonic field and the strong vibration modes of the Raman cluster tag.
Figure 11:
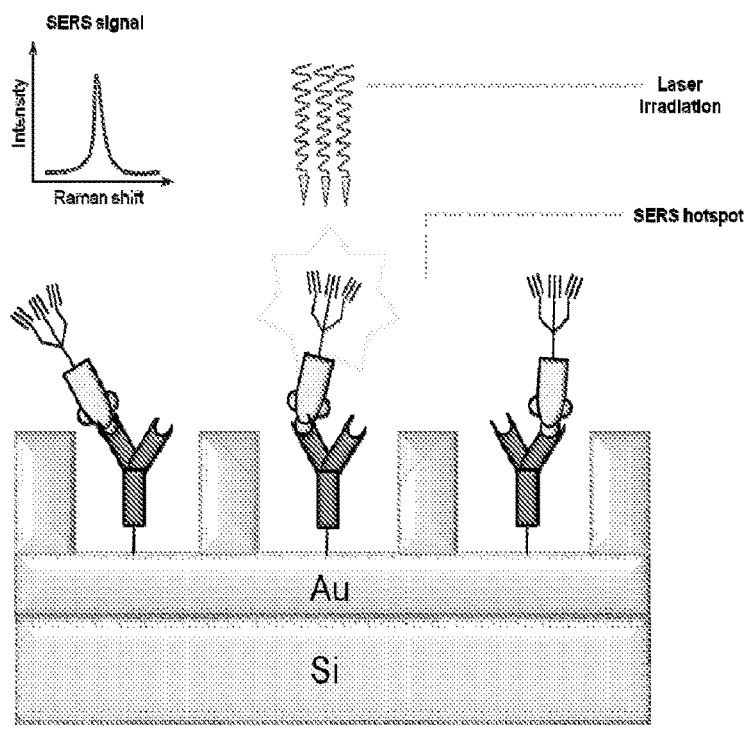

These untagged proteins are generally the baits or the targets in assays; the partner protein would be tagged with Raman detectable clusters as shown in FIGS. 8, 9, and 10. A number of examples of detection of protein-protein interactions are provided below, although there are many others not enumerated herein are also contemplated:
1. Unlabeled bait protein is covalently or ionically attached to a SERS surface, e.g., via thiol-gold interactions. A second protein is derivatized via lysine residues with dendrimer of azido or other (cyano, alkyne, methyl alkyne, etc.) tags. After binding, SERS is carried out to determine affinity, avidity, etc., for the bait protein. Placement and order of addition of the target and bait proteins can be reversed such that the former is attached to the surface and the latter is tagged as the probe.
2. A modification would feature proteins (receptors) on surfaces of cells which may be lysed and disposed on the SERS surface. Various concentrations of Raman cluster tag-labeled ligands in solution are added to (a) discover if the receptor is present on the cells; (b) the density of the receptors on the cell surface; or (c) the binding affinity, etc. This is of particular interest for studies in tumor development where receptors or their ligands are gained/lost (oncogenes/tumor suppressors).
3. Where multiple different receptors may be present, or where receptors have low specificity for binding of ligands, one can take advantage of distinct tag clusters with different signatures (Raman groups) on each ligand to determine each ligand's relative affinity for the receptor.
4. Similarly, the method may be used to study multi-protein assemblies, and to determine the order of protein addition. One can attach one of the proteins to the surface, and have each of the other proteins labeled with a different tag cluster (i.e., azido for one, alkyne for a second, cyano for the third, etc). SERS detection combined with statistical analysis of the signatures obtained indicate which order of addition of the different proteins produces the final assembly.
5. Another use of the approach would be for protein arrays, wherein peptide antigens modified with the Raman cluster tags are used to probe the arrays of antibodies displayed on the surface. As shown in FIG. 11(A), antibodies are immobilized on the gold-coated SERS nanostructures using conventional attachment chemistries [Shipway et al, 2000] and the antigen is introduced, which is labeled with a Raman cluster tag. As shown in FIG. 11(B), the antibody uniquely recognizes the antigen, allowing the two structures to bind together with precision. The bound antigen is positioned such that the Raman cluster tag is located close to the SERS hotspots upon laser irradiation. Large SERS enhancement is observed due to the mutual interplay between the localized surface plasmonic field and the strong vibration modes of the Raman cluster tag.

In each scenario, with chemically cleavable or photocleavable linkers, alternative options exist such as the ability to add interacting molecules one-by-one. This is particularly useful for measuring the order of addition of subunits of a multi-subunit protein or protein complex.

A major goal of this approach is to identify very low levels of a protein in a cell or tissue, approaching or surpassing the sensitivity of fluorescent techniques, and approaching single molecule sensitivity.

VII. Detection of DNA-Protein Interactions

In order to understand gene regulation at the transcriptional level, it is critical to know the binding efficiency of transcription factors ("TFs") to their binding motifs (promoter or enhancer elements). To detect such DNA-protein interactions, one attaches the transcription factor to SERS surface and label the promoter or enhancer element (usually 4-10 bases) with the Raman cluster tags.

Productive binding usually involves high affinity interactions, and may require binding of multiple transcription factors to nearby motifs and to each other. Therefore, a promoter or enhancer stretch of DNA containing 2 or more motifs may be attached to SERS surface, and two or more transcription factors added, each with a different signature Raman tag cluster (one with azido tag cluster and one with cyano tag cluster, for instance). This approach may be adapted to detect 3, 4, or more TFs or associated factors, using multiple tag clusters each containing a unique or combinations of Raman scattering chemical groups. Using the above approach, one could obtain information such as co-operativity among TFs for enhancement or silencing, and competition for the same binding motifs or regions.

To bind DNA to the surface, one may use a variety of established methods, including interaction of biotinylated DNA to streptavidin-coated SERS surfaces, attachment of NHS-ester end-modified DNA to an amino-decorated surface, or generation of amide bonds to carboxy-coated surfaces.

It is also possible to use a reverse approach, i.e., bind one or more of the transcription factors to the surface, and label one or more DNA molecules with Raman tag clusters.

Finally, using either cleavable or non-cleavable tag clusters allows one to add a multiplicity of proteins to the DNA in specific order.

Figure 12:
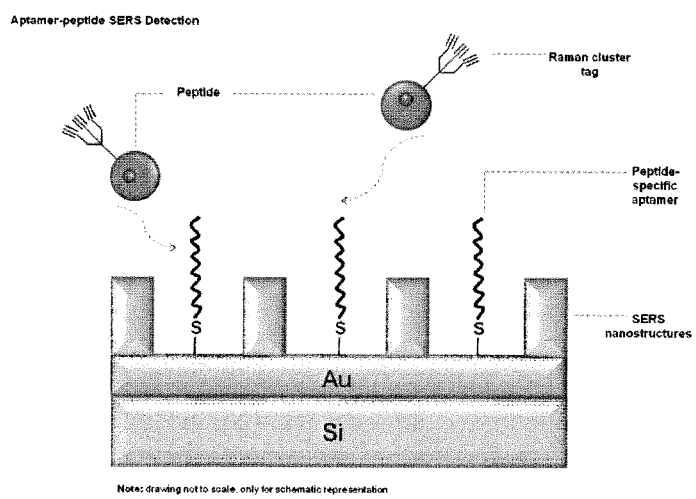
FIG. 12. Scheme of aptamer-peptide SERS detection. (A) Aptamers are immobilized on the gold-coated SERS nanostructures via thiol-gold bonding and peptides labeled with Raman cluster tags are introduced. (B) Peptides bind to aptamer counterparts with high affinity and specificity. When peptides trapped by the aptamer are close enough to a SERS hotspot, a strong Raman signal emanates from at least one of the cluster tags upon laser irradiation.
Figure 12:
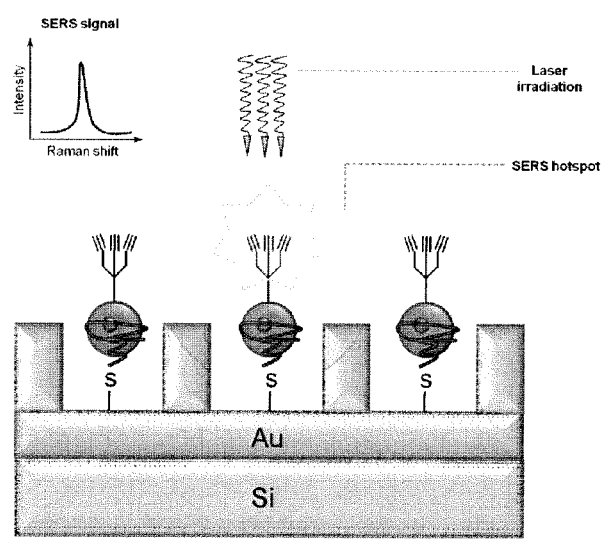

Another application deals with aptasensors. In aptasensors, aptamers (short single-stranded oligonucleotides) bind to targets with high affinity and selectivity. Their use as molecular recognition elements has emerged as a viable approach for biosensing, diagnostics, and therapeutics. A molecular recognition platform using Raman cluster tag labeled peptides and SERS substrate bound aptamers is shown in FIG. 12. Specifically, FIG. 12(A) shows aptamers immobilized on the gold-coated SERS nanostructures via thiol-gold bonding and introduction of peptides labeled with Raman cluster tags; FIG. 12(B) shows the peptides bind to aptamer counterparts with high affinity and specificity. When peptides trapped by the aptamer are close enough to a SERS hotspot, a strong Raman signal emanates from at least one of the cluster tags upon laser irradiation.

VIII. Detection of RNA-Protein Interaction

RNA binding proteins are involved in important aspects of RNA maturation and regulation, including regulation of splicing, and potential translation enhancement. They are part of ribonucleoprotein complexes and bind to specific single-stranded or double-stranded RNA recognition motifs. Applying the methodology for detection of DNA-protein interactions, one can attach the RNA motif to a SERS surface, and probe with RNA-binding proteins tagged with Raman tag clusters. Alternately, one can label the RNA with the clustered tags and react with unlabeled RNA-binding proteins attached to the SERS surface. Binding of RNA to a surface is similar to that for DNA discussed above.

IX. Detection of RNA-RNA Interaction

MicroRNAs (miRNAs) are known to bind to messenger RNA (mRNA) molecules, usually to motifs found in the 3'-UTRs of the latter, whereby miRNAs cause mRNA degradation or inhibition of translation. Such interactions can be detected using the approach described herein by label either the RNA motifs or the miRNAs with the Raman tag clusters, with the respective unlabeled partner molecule attached to a SERS surface.

X. Detection of Other Interactions

DNA-RNA or DNA-DNA hybridization on solid supports (microarray assays), DNA-DNA or RNA-RNA ligation reactions, protein-metabolite interactions, receptor-non ligand interactions, and study of members of interaction pathways could all benefit from the placement of clustered tags on one of the interacting partners.

REFERENCES

1, Fuller, C. W., Middendorf, L. R., Benner, S. A., Church, G. M. Harris, T., Huang, X. Jovanovich, S. B., Nelson, J. R., Schloss, J. A., Schwartz, D. C. & Vezenov, D. V. The challenges of sequencing by synthesis. *Nat Biotechnol* 27, 1013-23 (2009).
2. Guo, J. Yu, L. Turro, N. J. & Ju, J. An integrated system for DNA sequencing by synthesis using novel nucleotide analogs. *Acc Chem Res* 43, 551-63 (2010).
3. Hawkins, R. D., Hon, G. C. & Ren, B. Next-generation genomics: an integrative approach. *Nat Rev Genet* 11, 476-86 (2010).
4. Hsiao, W. H., Chen, H. Y., Yang, Y. C., Chen, Y. L., Lee, C. Y. & Chiu, H. T. Surface-Enhanced Raman Scattering Imaging of a Single Molecule on Urchin-like Silver Nanowires. *ACS Appl Mater Interfaces* 3, 3280-3284 (2011).
5. Ju, J., Kim, D. H., Bi, L., Meng, Q., Bai, X., Li, Z., Li, X., Marma, M. S., Shi, S., Wu, J., Edwards, J. R., Romu, A. & Turro, N. J. Four-color DNA sequencing by synthesis using cleavable fluorescent nucleotide reversible terminators. *Proc Natl Acad Sci USA* 103, 19635-40 (2006)
6. Kleinman, S. L., Ringe, E., Valley, N., Wustholz, K. L., Philllips, E., Scheidt, K. A., Schatz, G. C., & Van Duyne, R. P. Single-molecule surface-enhanced Raman spectroscopy of crystal violet isotopologues: theory and experiment. *J Am Chem Soc* 133, 4115-22 (2011).
7. Kneipp, K., Kneipp, H., Kartha B., Manoharan, R., Deinum, G., Itzkan, I., Dasari, R. R. & Feld, M. S. Detection and identification of a single DNA base molecule using surface-enhanced Raman scattering". *Phys Rev E* 57, R6281-R6284 (1998).
8. Korlach, J., Bibillo, A., Wegener, J., Peluso, P., Pham, T. T., Park, I., Clark, S., Otto, G. A. & Turner, S. W. Long, processive enzymatic DNA synthesis using 100% dye-labeled terminal phosphate-linked nucleotides. *Nucleosides Nucleotides Nucleic Acids* 27, 1072-83 (2008).
9, Korlach, J., Bjornson, K. P., Cheudhuri, B. P., Cicero, R. L., Flusberg, B. A., Gray, J. J. Holden, D., Saxena, R., Wegener, J. & Turner, S. W. Real-time DNA sequencing from single polymerase molecules. *Methods Enzymol* 472, 431-55 (2010).
10. Kumar, S., Sood, A., Wegener, S. Finn, P. J., Nampalli, S., Nelson, J. R. Sekher, A., Mitsis, P., Macklin, J. & Fuller, C. W. Terminal phosphate labeled nucleotides: synthesis, applications, and linker effect on incorporation by DNA polymerases. *Nucleosides Nucleotides Nucleic Acids* 24, 401-8 (2005).
11. Li, W. D., Ding, F., Hu, J., & Chou, S. Y. Three-dimensional cavity nanoantenna coupled plasmonic nanodots for ultrahigh and uniform surface-enhanced Raman scattering over large area. *Opt Express* 19, 3925-36 (2011).
12, Metzker, M. Sequencing technologies—the next generation. *Nat. Rev. Genet.* 11, 31-46 (2010).
13. Morozova, O., Hirst, M. & Marra, M. A. Applications of new sequencing technologies for transcriptome analysis. *Annu Rev Genomics Hum Genet* 10, 135-51 (2009).
14. Nie, S. & Emory, S. R. Probing Single Molecules and Single Nanoparticles by Surface-Enhanced Raman Scattering. *Science* 275, 1102-6 (1997).
15. Ornelas, C. & Neck, M. Construction of well-defined multifunctional dendrimers using a trifunctional core. *Chem Comm* 5710-5712 (2009).
16. Ozsolak, F. & Milos, P. M. RNA sequencing: advances, challenges and opportunities. *Nat Rev Genet* 12, 87-98 (2011).
17. Park, P. J. ChIP-seq: advantages and challenges of a maturing technology. *Nat Rev Genet* 10, 669-80 (2009).
18. Shipway, A. N., Katz, E., & Willner, I. *ChemPhysChem* 1, 18-52 (2000).
19. Socrates, G. *Infrared and Raman Characteristic Group Frequencies: Tables and Charts*. $3^{rd}$ ed. John Wiley & Sons (2001).
20. Sood, A., Kumar, S., Nampalli, S., Nelson, J. R., Macklin, J. & Fuller, C. W. Terminal phosphate-labeled nucleotides with improved substrate properties for homogeneous nucleic acid assays. *J Am Chem Soc* 127, 2394-5 (2005).
21. Varley, K. E. & Mitra, R. D. Bisulfite patch PCR enables multiplexed sequencing of promoter methylation across cancer samples. *Genome Res.* 20, 1279-87 (2010).

22. Wu, J., Zhang, S., Meng, Q., Cao, H., Li, Z., Li, X., Shi, S., Kim, D. H., Bi, L., Turro, N. J. & Ju, J. 3'-O-modified nucleotides as reversible terminators for pyrosequencing. *Proc Natl. Acad Sci USA* 104, 16462-7 (2007).

What is claimed is:

1. A nucleoside polyphosphate analog having the structure:

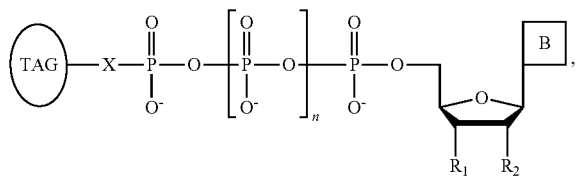

wherein B is a base and is adenine, guanine, cytosine, uracil, thymine, or a derivative thereof, wherein $R_1$ is OH, wherein $R_2$ is OH or H, wherein n is 1, 2, 3, or 4, wherein X is a linker, and wherein the tag comprises a plurality of identical Raman-scattering moieties.

2. The nucleoside polyphosphate analog of claim 1, wherein each of the plurality of Raman-scattering moieties has a Raman spectroscopy peak with wavenumber from 2000 cm$^{-1}$ to 2300 cm$^{-1}$.

3. The nucleoside polyphosphate analog of claim 1, wherein each of the plurality of Raman-scattering moieties is selected from the group consisting of —N=N=N, —C≡N, —C≡CH, and —C≡C—CH$_3$.

4. The nucleoside polyphosphate analog of claim 1, wherein the tag further comprises at least one Raman-scattering moiety that is different from the identical Raman-scattering moieties of the plurality of identical Raman-scattering moieties.

5. The nucleoside polyphosphate analog of claim 1, wherein the tag comprises 3 identical Raman-scattering moieties.

6. The nucleoside polyphosphate analog of claim 1, wherein the plurality of Raman-scattering moieties forms a linear tag.

7. The nucleoside polyphosphate analog of claim 1, wherein the plurality of Raman-scattering moieties forms a non-linear tag.

8. The nucleoside polyphosphate analog of claim 7, wherein the non-linear tag is a dendrimer tag.

9. The nucleoside polyphosphate analog of claim 2, wherein the tag has a Raman spectroscopy peak with wavenumber from 2125 cm$^{-1}$ to 2260 cm$^{-1}$.

10. The nucleoside polyphosphate analog of claim 1, wherein the linker is selected from the group consisting of O, NH, S, CH$_2$, amino acids, peptides, proteins, carbohydrates, polyethylene glycols of different length and molecular weights, aliphatic acids, aromatic acids, alcohols or thiol groups (substituted or unsubstituted), cyano groups, nitro groups, alkyl groups, alkenyl groups, alkynyl groups, and azido groups.

11. A composition comprising four deoxyribonucleoside polyphosphate (dNPP) analogs, each dNPP analog having the structure:

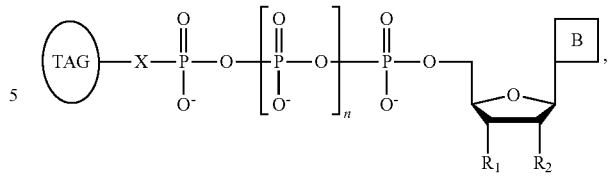

wherein B is a base and is adenine, guanine, cytosine, thymine, or a derivative thereof, wherein $R_1$ is OH, wherein $R_2$ is H, wherein n is 1, 2, 3, or 4, wherein X is a linker, wherein the tag comprises a plurality of identical Raman-scattering moieties, wherein (i) the Raman spectroscopy peak of the tag on each dNPP analog is distinguishable from the Raman spectroscopy peak of the tag on each of the remaining three dNPP analogs, and (ii) each dNPP analog comprises a base which is different from the base of each of the remaining three dNPP analogs.

12. A composition comprising four ribonucleoside polyphosphate (rNPP) analogs, each rNPP analog having the structure:

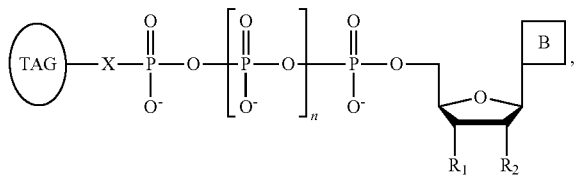

wherein B is a base and is adenine, guanine, cytosine, uracil, or a derivative thereof, wherein $R_1$ is OH, wherein $R_2$ is OH, wherein n is 1, 2, 3, or 4, wherein X is a linker, wherein the tag comprises a plurality of identical Raman-scattering moieties, wherein (i) the Raman spectroscopy peak of the tag on each rNPP analog is distinguishable from the Raman spectroscopy peak of the tag on each of the remaining three rNPP analogs, and (ii) each rNPP analog comprises a base which is different from the base of each of the remaining three rNPP analogs.

13. A method for determining the sequence of a single-stranded DNA comprising:

(a) contacting the single-stranded DNA having a primer hybridized to a portion thereof with a DNA polymerase and four deoxyribonucleoside polyphosphate (dNPP) analogs under conditions permitting the DNA polymerase to catalyze incorporation onto the primer of a dNPP analog complementary to a nucleotide residue of the single-stranded DNA which is immediately 5' to a nucleotide residue of the single-stranded DNA hybridized to the 3' terminal nucleotide residue of the primer, so as to form a DNA extension product, wherein each dNPP analog has the structure:

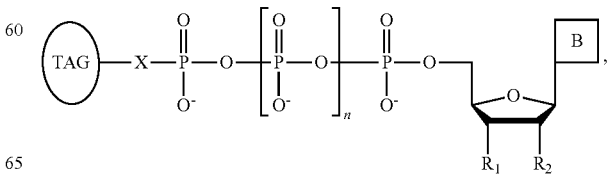

wherein B is a base and is adenine, guanine, cytosine, thymine, or a derivative thereof, wherein $R_1$ is OH, wherein $R_2$ is H, wherein n is 1, 2, 3, or 4, wherein X is a linker, wherein the tag comprises a plurality of identical Raman-scattering moieties, wherein (i) the Raman spectroscopy peak of the tag on each dNPP analog is distinguishable from the Raman spectroscopy peak of the tag on each of the remaining three dNPP analogs, and (ii) each dNPP analog comprises a base which is different from the base of each of the remaining three dNPP analogs, and wherein the incorporation of the dNPP analog releases a tagged polyphosphate;

(b) determining the wavenumber of the Raman spectroscopy peak of the tagged polyphosphate released in step (a), so as to thereby determine the identity of the incorporated dNPP analog and the identity of the complementary nucleotide residue in the single-stranded DNA; and (c) iteratively performing steps (a) and (b) for each nucleotide residue of the single-stranded DNA to be sequenced so as to thereby determine the sequence of the single-stranded DNA.

14. A method for determining the sequence of a single-stranded RNA comprising:

(a) contacting the single-stranded RNA having a primer hybridized to a portion thereof with an RNA polymerase and four ribonucleoside polyphosphate (rNPP) analogs under conditions permitting the RNA polymerase to catalyze incorporation onto the primer of an rNPP analog complementary to a nucleotide residue of the single-stranded RNA which is immediately 5' to a nucleotide residue of the single-stranded RNA hybridized to the 3' terminal nucleotide residue of the primer, so as to form an RNA extension product, wherein each rNPP analog has the structure:

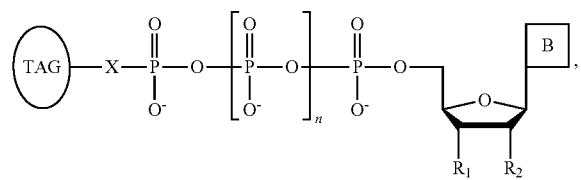

wherein B is a base and is adenine, guanine, cytosine, uracil, or a derivative thereof, wherein $R_1$ is OH, wherein $R_2$ is OH, wherein n is 1, 2, 3, or 4, wherein X is a linker, wherein the tag comprises a plurality of identical Raman-scattering moieties, wherein (i) the Raman spectroscopy peak of the tag on each rNPP analog is distinguishable from the Raman spectroscopy peak of the tag on each of the remaining three rNPP analogs, and (ii) each rNPP analog comprises a base which is different from the base of each of the remaining three rNPP analogs, and wherein the incorporation of the rNPP analog releases a tagged polyphosphate;

(b) determining the wavenumber of the Raman spectroscopy peak of the tagged polyphosphate released in step (a), so as to thereby determine the identity of the incorporated rNPP analog and the identity of the complementary nucleotide residue in the single-stranded RNA; and (c) iteratively performing steps (a) and (b) for each nucleotide residue of the single-stranded RNA to be sequenced so as to thereby determine the sequence of the single-stranded RNA.

15. The method of claim 13, wherein the polymerase is immobilized on a solid surface.

16. The method of claim 13, wherein the Raman spectroscopy peak is determined using surface-enhanced Raman spectroscopy (SERS).

17. The method of claim 16, wherein the polymerase is immobilized on a SERS substrate.

18. The method of claim 17, wherein the polymerase is immobilized such that only the tagged polyphosphate released in step (a) is within the detection range of the SERS detector.

19. The method of claim 18, wherein the polymerase is immobilized such that the tagged polyphosphate released in step (a) is within a cavity on the SERS substrate.

20. The method of claim 13, wherein the linker is selected from the group consisting of O, NH, S, $CH_2$, amino acids, peptides, proteins, carbohydrates, polyethylene glycols of different length and molecular weights, aliphatic acids, aromatic acids, alcohols or thiol groups (substituted or unsubstituted), cyano groups, nitro groups, alkyl groups, alkenyl groups, alkynyl groups, and azido groups.

* * * * *